US012691174B2

(12) United States Patent
Wu et al.

(10) Patent No.: US 12,691,174 B2
(45) Date of Patent: *Jul. 28, 2026

(54) PHARMACEUTICAL COMPOSITION CONTAINING ANTI-IL-4R ANTIBODY AND USE THEREOF

(71) Applicants: JIANGSU HENGRUI PHARMACEUTICALS CO., LTD., Lianyungang (CN); SHANGHAI HENGRUI PHARMACEUTICAL CO., LTD., Shanghai (CN)

(72) Inventors: Tingting Wu, Shanghai (CN); Zhen Yan, Shanghai (CN); Xun Liu, Shanghai (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 885 days.

This patent is subject to a terminal disclaimer.

(21) Appl. No.: 17/800,868

(22) PCT Filed: Feb. 19, 2021

(86) PCT No.: PCT/CN2021/076854
§ 371 (c)(1),
(2) Date: Aug. 18, 2022

(87) PCT Pub. No.: WO2021/164728
PCT Pub. Date: Aug. 26, 2021

(65) Prior Publication Data
US 2023/0088052 A1     Mar. 23, 2023

(30) Foreign Application Priority Data

Feb. 21, 2020   (CN) ......................... 202010107765.0
Feb. 2, 2021    (CN) ......................... 202110145455.2

(51) Int. Cl.
| | | |
|---|---|---|
| *A61K 39/395* | (2006.01) | |
| *A61K 47/12* | (2006.01) | |
| *A61K 47/22* | (2006.01) | |
| *C07K 16/28* | (2006.01) | |

(52) U.S. Cl.
CPC ........ *A61K 39/39591* (2013.01); *A61K 47/12* (2013.01); *A61K 47/22* (2013.01); *C07K 16/2866* (2013.01); *C07K 2317/94* (2013.01)

(58) Field of Classification Search
CPC .. A61K 39/39591; A61K 47/12; A61K 47/22; A61K 2039/505; A61K 9/0019; A61K 9/19; A61K 47/02; A61K 47/183; A61K 47/26; C07K 16/2866; C07K 2317/94; C07K 2317/24; C07K 2317/73; C07K 2317/76; C07K 2317/92
See application file for complete search history.

(56) References Cited

U.S. PATENT DOCUMENTS

2009/0306348 A1 * 12/2009 Goldstein ................ A61K 9/19
530/389.2

FOREIGN PATENT DOCUMENTS

| CN | 103501814 A | 1/2014 | |
| CN | 106267189 * | 1/2017 | .......... A61K 39/395 |
| CN | 106267189 A | 1/2017 | |
| CN | 106604744 A | 4/2017 | |
| CN | 111686247 A | 9/2020 | |

* cited by examiner

*Primary Examiner* — Nelson B Moseley, II
(74) *Attorney, Agent, or Firm* — Morgan, Lewis & Bockius LLP

(57) ABSTRACT

Provided are a pharmaceutical composition containing an anti-IL-4R antibody and the use thereof. The pharmaceutical composition contains an anti-IL-4R antibody or an antigen-binding fragment thereof in a histidine-acetic acid buffer agent, a viscosity modifier, a surfactant, and a stabilizer.

22 Claims, 2 Drawing Sheets
Specification includes a Sequence Listing.

SEQUENCE LISTING

```
<160> NUMBER OF SEQ ID NOS: 48

<210> SEQ ID NO 1
<211> LENGTH: 118
<212> TYPE: PRT
<213> ORGANISM: Artificial Sequence
<220> FEATURE:
<223> OTHER INFORMATION: Synthetic Sequence_Heavy chain variable region
      of murine monoclonal antibody 25G7

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Thr Arg Gly Asn Lys Arg Gly Phe Phe Asp Tyr Trp Gly Gln Gly Thr
            100                 105                 110

Ile Leu Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: Synthetic Sequence_Light chain variable region
      of murine monoclonal antibody 25G7

<400> SEQUENCE: 2

Gln Ile Val Leu Thr Gln Ser Pro Ala Leu Met Ser Ala Ser Pro Gly
1               5                   10                  15
```

```
Glu Lys Val Thr Met Thr Cys Asn Ala Ser Ser Ser Val Ser Tyr Met
        20                  25                  30

Tyr Trp Tyr Gln Arg Lys Pro Arg Ser Ser Pro Lys Pro Trp Ile Tyr
        35                  40                  45

Leu Thr Ser Asn Leu Ala Ser Gly Val Pro Val Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Arg Ser Asn Pro Pro Met
                85                  90                  95

Leu Thr Phe Gly Ser Gly Thr Lys Leu Glu Val Lys
            100                 105
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic Sequence_HCDR1 of murine monoclonal
      antibody 25G7

<400> SEQUENCE: 3

Gly Phe Thr Phe Ser Asp Tyr Gly Met His
1               5                   10
```

```
<210> SEQ ID NO 4
<211> LENGTH: 17
<212> TYPE: PRT
<213> ORGANISM: Artificial Sequence
<220> FEATURE:
<223> OTHER INFORMATION: Synthetic Sequence_HCDR2 of murine monoclonal
      antibody 25G7

<400> SEQUENCE: 4

Phe Ile Ser Ser Gly Ser Ser Ile Ile Tyr Tyr Ala Asp Ile Val Lys
1               5                   10                  15

Gly
```

```
<210> SEQ ID NO 5
<211> LENGTH: 9
<212> TYPE: PRT
<213> ORGANISM: Artificial Sequence
<220> FEATURE:
<223> OTHER INFORMATION: Synthetic Sequence_HCDR3 of murine monoclonal
      antibody 25G7

<400> SEQUENCE: 5

Gly Asn Lys Arg Gly Phe Phe Asp Tyr
1               5
```

```
<210> SEQ ID NO 6
<211> LENGTH: 10
<212> TYPE: PRT
<213> ORGANISM: Artificial Sequence
<220> FEATURE:
<223> OTHER INFORMATION: Synthetic Sequence_LCDR1 of murine monoclonal
      antibody 25G7

<400> SEQUENCE: 6

Asn Ala Ser Ser Ser Val Ser Tyr Met Tyr
1               5                   10
```

```
<210> SEQ ID NO 7
```

```
<211> LENGTH: 7
<212> TYPE: PRT
<213> ORGANISM: Artificial Sequence
<220> FEATURE:
<223> OTHER INFORMATION: Synthetic Sequence_LCDR2 of murine monoclonal
      antibody 25G7

<400> SEQUENCE: 7

Leu Thr Ser Asn Leu Ala Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Sequence_LCDR3 of murine monoclonal
      antibody 25G7

<400> SEQUENCE: 8

Gln Gln Trp Arg Ser Asn Pro Pro Met Leu Thr
1               5                   10

<210> SEQ ID NO 9
<211> LENGTH: 125
<212> TYPE: PRT
<213> ORGANISM: Artificial Sequence
<220> FEATURE:
<223> OTHER INFORMATION: Synthetic Sequence_Heavy chain variable region
      of murine monoclonal antibody 7B10

<400> SEQUENCE: 9

Gln Val Gln Leu Gln Gln Pro Gly Thr Glu Leu Leu Lys Pro Gly Ala
1               5                   10                  15

Ser Val Ser Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile His Pro Asn Ser Asp Thr Thr Lys Phe Ser Glu Asn Phe
    50                  55                  60

Lys Thr Arg Ala Thr Leu Thr Ile Asp Lys Ser Ser Ser Thr Ala Tyr
65                  70                  75                  80

Met Lys Leu Ser Ser Leu Thr Ser Glu Asp Ser Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Thr Gly Thr Thr Val Thr Val Ser Ser
        115                 120                 125

<210> SEQ ID NO 10
<211> LENGTH: 111
<212> TYPE: PRT
<213> ORGANISM: Artificial Sequence
<220> FEATURE:
<223> OTHER INFORMATION: Synthetic Sequence_Light chain variable region
      of murine monoclonal antibody 7B10

<400> SEQUENCE: 10

Asp Ile Val Leu Thr Gln Ser Pro Pro Ser Leu Ala Val Ser Leu Gly
1               5                   10                  15

Gln Arg Ala Thr Ile Ser Cys Lys Ala Ser Gln Ser Val Asp Tyr Gly
            20                  25                  30

Gly Asp Ser Tyr Met Asn Trp Tyr Gln Gln Lys Leu Gly Gln Pro Pro
```

-continued

```
              35                 40                 45

Lys Val Leu Ile Tyr Ala Ala Ser Asn Leu Glu Ser Gly Ile Pro Ala
   50                 55                 60

Arg Phe Ser Gly Ser Gly Ser Gly Thr Asp Phe Thr Leu Asn Ile His
65                 70                 75                 80

Pro Val Glu Glu Glu Asp Val Ala Thr Tyr Tyr Cys Gln His Ser Asn
                  85                 90                 95

Glu Asn Pro Pro Thr Phe Gly Gly Gly Thr Lys Leu Glu Ile Lys
              100                105                110

<210> SEQ ID NO 11
<211> LENGTH: 10
<212> TYPE: PRT
<213> ORGANISM: Artificial Sequence
<220> FEATURE:
<223> OTHER INFORMATION: Synthetic Sequence_HCDR1 of murine monoclonal
      antibody 7B10

<400> SEQUENCE: 11

Gly Tyr Thr Phe Thr Ser Tyr Trp Met His
1               5                 10

<210> SEQ ID NO 12
<211> LENGTH: 17
<212> TYPE: PRT
<213> ORGANISM: Artificial Sequence
<220> FEATURE:
<223> OTHER INFORMATION: Synthetic Sequence_HCDR2 of murine monoclonal
      antibody 7B10

<400> SEQUENCE: 12

Leu Ile His Pro Asn Ser Asp Thr Thr Lys Phe Ser Glu Asn Phe Lys
1               5                 10                15

Thr

<210> SEQ ID NO 13
<211> LENGTH: 16
<212> TYPE: PRT
<213> ORGANISM: Artificial Sequence
<220> FEATURE:
<223> OTHER INFORMATION: Synthetic Sequence_HCDR3 of murine monoclonal
      antibody 7B10

<400> SEQUENCE: 13

Ser Lys Ile Ile Thr Thr Ile Val Ala Arg His Trp Tyr Phe Asp Val
1               5                 10                15

<210> SEQ ID NO 14
<211> LENGTH: 15
<212> TYPE: PRT
<213> ORGANISM: Artificial Sequence
<220> FEATURE:
<223> OTHER INFORMATION: Synthetic Sequence_LCDR1 of murine monoclonal
      antibody 7B10

<400> SEQUENCE: 14

Lys Ala Ser Gln Ser Val Asp Tyr Gly Gly Asp Ser Tyr Met Asn
1               5                 10                15

<210> SEQ ID NO 15
<211> LENGTH: 7
<212> TYPE: PRT
<213> ORGANISM: Artificial Sequence
<220> FEATURE:
<223> OTHER INFORMATION: Synthetic Sequence_LCDR2 of murine monoclonal
```

```
             antibody 7B10
<220> FEATURE:
<221> NAME/KEY: DOMAIN
<222> LOCATION: (1)..(7)

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Sequence_LCDR3 of murine monoclonal
             antibody 7B10
<220> FEATURE:
<221> NAME/KEY: DOMAIN
<222> LOCATION: (1)..(9)

<400> SEQUENCE: 16

Gln His Ser Asn Glu Asn Pro Pro Thr
1               5

<210> SEQ ID NO 17
<211> LENGTH: 445
<212> TYPE: PRT
<213> ORGANISM: Artificial Sequence
<220> FEATURE:
<223> OTHER INFORMATION: Synthetic Sequence_Heavy chain of humanized
             antibody hu25G7
<220> FEATURE:
<221> NAME/KEY: CHAIN
<222> LOCATION: (1)..(445)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205
```

```
Asn Thr Lys Val Asp Lys Arg Val Glu Ser Lys Tyr Gly Pro Pro Cys
    210             215             220

Pro Pro Cys Pro Ala Pro Glu Phe Leu Gly Gly Pro Ser Val Phe Leu
225             230             235             240

Phe Pro Pro Lys Pro Lys Asp Thr Leu Met Ile Ser Arg Thr Pro Glu
            245             250             255

Val Thr Cys Val Val Val Asp Val Ser Gln Glu Asp Pro Glu Val Gln
            260             265             270

Phe Asn Trp Tyr Val Asp Gly Val Glu Val His Asn Ala Lys Thr Lys
        275             280             285

Pro Arg Glu Glu Gln Phe Asn Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Gly Leu Pro Ser Ser Ile Glu Lys Thr Ile Ser Lys
            325             330             335

Ala Lys Gly Gln Pro Arg Glu Pro Gln Val Tyr Thr Leu Pro Pro Ser
            340             345             350

Gln Glu Glu Met Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Arg Leu Thr Val Asp Lys Ser Arg Trp Gln
            405             410             415

Glu Gly Asn Val Phe Ser Cys Ser Val Met His Glu Ala Leu His Asn
            420             425             430

His Tyr Thr Gln Lys Ser Leu Ser Leu Ser Leu Gly Lys
        435             440             445
```

```
<210> SEQ ID NO 18
<211> LENGTH: 215
<212> TYPE: PRT
<213> ORGANISM: Artificial Sequence
<220> FEATURE:
<223> OTHER INFORMATION: Synthetic Sequence_Light chain of humanized
      antibody hu25G7
<220> FEATURE:
<221> NAME/KEY: CHAIN
<222> LOCATION: (1)..(215)

<400> SEQUENCE: 18
```

```
Glu Ile Val Leu Thr Gln Ser Pro Ala Thr Leu Ser Leu Ser Pro Gly
1               5               10              15

Glu Arg Ala Thr Leu Ser Cys Asn Ala Ser Ser Ser Val Ser Tyr Met
            20              25              30

Tyr Trp Tyr Gln Gln Lys Pro Gly Gln Ala Pro Arg Leu Leu Ile Tyr
        35              40              45

Leu Thr Ser Asn Leu Ala Ser Gly Ile Pro Ala Arg Phe Ser Gly Ser
    50              55              60

Gly Ser Gly Thr Asp Phe Thr Leu Thr Ile Ser Ser Leu Glu Pro Glu
65              70              75              80

Asp Phe Ala Val Tyr Tyr Cys Gln Gln Trp Arg Ser Asn Pro Pro Met
            85              90              95

Leu Thr Phe Gly Gly Gly Thr Lys Val Glu Ile Lys Arg Thr Val Ala
```

-continued

```
              100              105              110

Ala Pro Ser Val Phe Ile Phe Pro Pro Ser Asp Glu Gln Leu Lys Ser
        115              120              125

Gly Thr Ala Ser Val Val Cys Leu Leu Asn Asn Phe Tyr Pro Arg Glu
    130              135              140

Ala Lys Val Gln Trp Lys Val Asp Asn Ala Leu Gln Ser Gly Asn Ser
145              150              155              160

Gln Glu Ser Val Thr Glu Gln Asp Ser Lys Asp Ser Thr Tyr Ser Leu
            165              170              175

Ser Ser Thr Leu Thr Leu Ser Lys Ala Asp Tyr Glu Lys His Lys Val
            180              185              190

Tyr Ala Cys Glu Val Thr His Gln Gly Leu Ser Ser Pro Val Thr Lys
        195              200              205

Ser Phe Asn Arg Gly Glu Cys
    210              215

<210> SEQ ID NO 19
<211> LENGTH: 455
<212> TYPE: PRT
<213> ORGANISM: Artificial Sequence
<220> FEATURE:
<223> OTHER INFORMATION: Synthetic Sequence_Heavy chain of humanized
      antibody hu7B10

<400> SEQUENCE: 19

Glu Val Gln Leu Val Gln Ser Gly Ala Glu Val Lys Lys Pro Gly Ala
1                 5                 10               15

Ser Val Lys Val Ser Cys Lys Ala Ser Gly Tyr Thr Phe Thr Ser Tyr
            20               25               30

Trp Met His Trp Val Arg Gln Ala Pro Gly Gln Gly Leu Glu Trp Met
        35               40               45

Gly Leu Ile His Pro Asn Ser Asp Thr Thr Lys Phe Ser Glu Asn Phe
    50               55               60

Lys Thr Arg Val Thr Met Thr Ile Asp Thr Ser Ile Ser Thr Ala Tyr
65               70               75               80

Met Glu Leu Ser Arg Leu Arg Ser Asp Asp Thr Ala Val Tyr Tyr Cys
            85               90               95

Ala Lys Ser Lys Ile Ile Thr Thr Ile Val Ala Arg His Trp Tyr Phe
        100              105              110

Asp Val Trp Gly Gln Gly Thr Thr Val Thr Val Ser Ser Ala Ser Thr
        115              120              125

Lys Gly Pro Ser Val Phe Pro Leu Ala Pro Ser Ser Lys Ser Thr Ser
    130              135              140

Gly Gly Thr Ala Ala Leu Gly Cys Leu Val Lys Asp Tyr Phe Pro Glu
145              150              155              160

Pro Val Thr Val Ser Trp Asn Ser Gly Ala Leu Thr Ser Gly Val His
            165              170              175

Thr Phe Pro Ala Val Leu Gln Ser Ser Gly Leu Tyr Ser Leu Ser Ser
            180              185              190

Val Val Thr Val Pro Ser Ser Ser Leu Gly Thr Gln Thr Tyr Ile Cys
        195              200              205

Asn Val Asn His Lys Pro Ser Asn Thr Lys Val Asp Lys Lys Val Glu
    210              215              220

Pro Lys Ser Cys Asp Lys Thr His Thr Cys Pro Pro Cys Pro Ala Pro
225              230              235              240
```

```
Glu Leu Leu Gly Gly Pro Ser Val Phe Leu Phe Pro Pro Lys Pro Lys
                    245             250             255

Asp Thr Leu Met Ile Ser Arg Thr Pro Glu Val Thr Cys Val Val Val
            260             265             270

Asp Val Ser His Glu Asp Pro Glu Val Lys Phe Asn Trp Tyr Val Asp
        275             280             285

Gly Val Glu Val His Asn Ala Lys Thr Lys Pro Arg Glu Glu Gln Tyr
    290             295             300

Asn Ser Thr Tyr Arg Val Val Ser Val Leu Thr Val Leu His Gln Asp
305             310             315             320

Trp Leu Asn Gly Lys Glu Tyr Lys Cys Lys Val Ser Asn Lys Ala Leu
            325             330             335

Pro Ala Pro Ile Glu Lys Thr Ile Ser Lys Ala Lys Gly Gln Pro Arg
            340             345             350

Glu Pro Gln Val Tyr Thr Leu Pro Pro Ser Arg Glu Glu Met Thr Lys
        355             360             365

Asn Gln Val Ser Leu Thr Cys Leu Val Lys Gly Phe Tyr Pro Ser Asp
    370             375             380

Ile Ala Val Glu Trp Glu Ser Asn Gly Gln Pro Glu Asn Asn Tyr Lys
385             390             395             400

Thr Thr Pro Pro Val Leu Asp Ser Asp Gly Ser Phe Phe Leu Tyr Ser
            405             410             415

Lys Leu Thr Val Asp Lys Ser Arg Trp Gln Gln Gly Asn Val Phe Ser
            420             425             430

Cys Ser Val Met His Glu Ala Leu His Asn His Tyr Thr Gln Lys Ser
            435             440             445

Leu Ser Leu Ser Pro Gly Lys
    450             455
```

```
<210> SEQ ID NO 20
<211> LENGTH: 218
<212> TYPE: PRT
<213> ORGANISM: Artificial Sequence
<220> FEATURE:
<223> OTHER INFORMATION: Synthetic Sequence_Light chain of humanized
      antibody hu7B10
<220> FEATURE:
<221> NAME/KEY: CHAIN
<222> LOCATION: (1)..(218)

<400> SEQUENCE: 20
```

```
Asp Ile Val Leu Thr Gln Thr Pro Leu Ser Leu Ser Val Thr Pro Gly
1               5               10              15

Gln Pro Ala Ser Ile Ser Cys Lys Ala Ser Gln Ser Val Asp Tyr Gly
            20              25              30

Gly Asp Ser Tyr Met Asn Trp Tyr Leu Gln Lys Pro Gly Gln Pro Pro
        35              40              45

Gln Leu Leu Ile Tyr Ala Ala Ser Asn Leu Glu Ser Gly Val Pro Asp
    50              55              60

Arg Phe Ser Gly Ser Gly Ser Gly Thr Asp Phe Thr Leu Lys Ile Ser
65              70              75              80

Arg Val Glu Ala Glu Asp Val Gly Val Tyr Tyr Cys Gln His Ser Asn
            85              90              95

Glu Asn Pro Pro Thr Phe Gly Gly Gly Thr Lys Val Glu Ile Lys Arg
            100             105             110

Thr Val Ala Ala Pro Ser Val Phe Ile Phe Pro Pro Ser Asp Glu Gln
            115             120             125
```

```
Leu Lys Ser Gly Thr Ala Ser Val Val Cys Leu Leu Asn Asn Phe Tyr
    130             135             140
```

```
Pro Arg Glu Ala Lys Val Gln Trp Lys Val Asp Asn Ala Leu Gln Ser
145             150             155             160
```

```
Gly Asn Ser Gln Glu Ser Val Thr Glu Gln Asp Ser Lys Asp Ser Thr
            165             170             175
```

```
Tyr Ser Leu Ser Ser Thr Leu Thr Leu Ser Lys Ala Asp Tyr Glu Lys
            180             185             190
```

```
His Lys Val Tyr Ala Cys Glu Val Thr His Gln Gly Leu Ser Ser Pro
            195             200             205
```

```
Val Thr Lys Ser Phe Asn Arg Gly Glu Cys
    210             215
```

<210> SEQ ID NO 21
<211> LENGTH: 98
<212> TYPE: PRT
<213> ORGANISM: Artificial Sequence
<220> FEATURE:
<223> OTHER INFORMATION: Synthetic Sequence_Human germline heavy chain
      template IGHV3-48*01
<220> FEATURE:
<221> NAME/KEY: DOMAIN
<222> LOCATION: (1)..(98)

<400> SEQUENCE: 21

```
Glu Val Gln Leu Val Glu Ser Gly Gly Gly Leu Val Gln Pro Gly Gly
1               5               10              15
```

```
Ser Leu Arg Leu Ser Cys Ala Ala Ser Gly Phe Thr Phe Ser Ser Tyr
            20              25              30
```

```
Ser Met Asn Trp Val Arg Gln Ala Pro Gly Lys Gly Leu Glu Trp Val
        35              40              45
```

```
Ser Tyr Ile Ser Ser Ser Ser Ser Thr Ile Tyr Tyr Ala Asp Ser Val
    50              55              60
```

```
Lys Gly Arg Phe Thr Ile Ser Arg Asp Asn Ala Lys Asn Ser Leu Tyr
65              70              75              80
```

```
Leu Gln Met Asn Ser Leu Arg Ala Glu Asp Thr Ala Val Tyr Tyr Cys
                85              90              95
```

```
Ala Arg
```

<210> SEQ ID NO 22
<211> LENGTH: 95
<212> TYPE: PRT
<213> ORGANISM: Artificial Sequence
<220> FEATURE:
<223> OTHER INFORMATION: Synthetic Sequence_Human germline light chain
      template IGKV3-11*01
<220> FEATURE:
<221> NAME/KEY: DOMAIN
<222> LOCATION: (1)..(95)

<400> SEQUENCE: 22

```
Glu Ile Val Leu Thr Gln Ser Pro Ala Thr Leu Ser Leu Ser Pro Gly
1               5               10              15
```

```
Glu Arg Ala Thr Leu Ser Cys Arg Ala Ser Gln Ser Val Ser Ser Tyr
            20              25              30
```

```
Leu Ala Trp Tyr Gln Gln Lys Pro Gly Gln Ala Pro Arg Leu Leu Ile
        35              40              45
```

```
Tyr Asp Ala Ser Asn Arg Ala Thr Gly Ile Pro Ala Arg Phe Ser Gly
    50              55              60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 23
<211> LENGTH: 98
<212> TYPE: PRT
<213> ORGANISM: Artificial Sequence
<220> FEATURE:
<223> OTHER INFORMATION: Synthetic Sequence_Human germline heavy chain
      template IGHV1-2*02
<220> FEATURE:
<221> NAME/KEY: DOMAIN
<222> LOCATION: (1)..(98)

<400> SEQUENCE: 23

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 24
<211> LENGTH: 100
<212> TYPE: PRT
<213> ORGANISM: Artificial Sequence
<220> FEATURE:
<223> OTHER INFORMATION: Synthetic Sequence_Human germline light chain
      template IGKV2D-29*01
<220> FEATURE:
<221> NAME/KEY: DOMAIN
<222> LOCATION: (1)..(100)

<400> SEQUENCE: 24

Asp Ile Val Met Thr Gln Thr Pro Leu Ser Leu Ser Val Thr Pro Gly
1                   5                   10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 25
<211> LENGTH: 118
<212> TYPE: PRT

-continued

<213> ORGANISM: Artificial Sequence
<220> FEATURE:
<223> OTHER INFORMATION: Synthetic Sequence_hu25G7-VH-a
<220> FEATURE:
<221> NAME/KEY: DOMAIN
<222> LOCATION: (1)..(118)

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Lys Arg Gly Phe Phe Asp Tyr Trp Gly Gln Gly Thr
            100                 105                 110

Leu Val Thr Val Ser Ser
        115
```

<210> SEQ ID NO 26
<211> LENGTH: 118
<212> TYPE: PRT
<213> ORGANISM: Artificial Sequence
<220> FEATURE:
<223> OTHER INFORMATION: Synthetic Sequence_hu25G7-VH-b
<220> FEATURE:
<221> NAME/KEY: DOMAIN
<222> LOCATION: (1)..(118)

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<223> OTHER INFORMATION: Synthetic Sequence_hu25G7-VH-c
<220> FEATURE:
<221> NAME/KEY: DOMAIN

```
<222> LOCATION: (1)..(118)

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115

<210> SEQ ID NO 28
<211> LENGTH: 108
<212> TYPE: PRT
<213> ORGANISM: Artificial Sequence
<220> FEATURE:
<223> OTHER INFORMATION: Synthetic Sequence_hu25G7-VL-a
<220> FEATURE:
<221> NAME/KEY: DOMAIN
<222> LOCATION: (1)..(108)

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 29
<211> LENGTH: 108
<212> TYPE: PRT
<213> ORGANISM: Artificial Sequence
<220> FEATURE:
<223> OTHER INFORMATION: Synthetic Sequence_hu25G7-VL-b
<220> FEATURE:
<221> NAME/KEY: DOMAIN
<222> LOCATION: (1)..(108)

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
```

-continued

```
                20              25              30

Tyr Trp Tyr Gln Gln Lys Pro Gly Gln Ala Pro Arg Leu Leu Ile Tyr
        35              40              45

Leu Thr Ser Asn Leu Ala Ser Gly Ile Pro Ala Arg Phe Ser Gly Ser
    50              55              60

Gly Ser Gly Thr Asp Tyr Thr Leu Thr Ile Ser Ser Leu Glu Pro Glu
65              70              75              80

Asp Phe Ala Val Tyr Tyr Cys Gln Gln Trp Arg Ser Asn Pro Pro Met
            85              90              95

Leu Thr Phe Gly Gly Gly Thr Lys Val Glu Ile Lys
            100             105

<210> SEQ ID NO 30
<211> LENGTH: 108
<212> TYPE: PRT
<213> ORGANISM: Artificial Sequence
<220> FEATURE:
<223> OTHER INFORMATION: Synthetic Sequence_hu25G7-VL-c
<220> FEATURE:
<221> NAME/KEY: DOMAIN
<222> LOCATION: (1)..(108)

<400> SEQUENCE: 30

Glu Ile Val Leu Thr Gln Ser Pro Ala Thr Leu Ser Leu Ser Pro Gly
1               5               10              15

Glu Arg Ala Thr Leu Ser Cys Asn Ala Ser Ser Ser Val Ser Tyr Met
                20              25              30

Tyr Trp Tyr Gln Gln Lys Pro Gly Gln Ala Pro Arg Pro Trp Ile Tyr
        35              40              45

Leu Thr Ser Asn Leu Ala Ser Gly Ile Pro Ala Arg Phe Ser Gly Ser
    50              55              60

Gly Ser Gly Thr Asp Tyr Thr Leu Thr Ile Ser Ser Leu Glu Pro Glu
65              70              75              80

Asp Phe Ala Val Tyr Tyr Cys Gln Gln Trp Arg Ser Asn Pro Pro Met
            85              90              95

Leu Thr Phe Gly Gly Gly Thr Lys Val Glu Ile Lys
            100             105

<210> SEQ ID NO 31
<211> LENGTH: 125
<212> TYPE: PRT
<213> ORGANISM: Artificial Sequence
<220> FEATURE:
<223> OTHER INFORMATION: Synthetic Sequence_hu7B10-VH-a
<220> FEATURE:
<221> NAME/KEY: DOMAIN
<222> LOCATION: (1)..(125)

<400> SEQUENCE: 31

Glu Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
                20              25              30

Trp Met His Trp Val Arg Gln Ala Pro Gly Gln Gly Leu Glu Trp Met
        35              40              45

Gly Leu Ile His Pro Asn Ser Asp Thr Thr Lys Phe Ser Glu Asn Phe
    50              55              60

Lys Thr Arg Val Thr Met Thr Arg Asp Thr Ser Ile Ser Thr Ala Tyr
65              70              75              80
```

-continued

```
Met Glu Leu Ser Arg Leu Arg Ser Asp Asp Thr Ala Val Tyr Tyr Cys
                85                  90                  95

Ala Arg Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125
```

<210> SEQ ID NO 32
<211> LENGTH: 125
<212> TYPE: PRT
<213> ORGANISM: Artificial Sequence
<220> FEATURE:
<223> OTHER INFORMATION: Synthetic Sequence_hu7B10-VH-b
<220> FEATURE:
<221> NAME/KEY: DOMAIN
<222> LOCATION: (1)..(125)

<400> SEQUENCE: 32

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Leu Ile His Pro Asn Ser Asp Thr Thr Lys Phe Ser Glu Asn Phe
        50                  55                  60

Lys Thr Arg Val Thr Met Thr Ile Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125
```

<210> SEQ ID NO 33
<211> LENGTH: 125
<212> TYPE: PRT
<213> ORGANISM: Artificial Sequence
<220> FEATURE:
<223> OTHER INFORMATION: Synthetic Sequence_hu7B10-VH-c

<400> SEQUENCE: 33

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Leu Ile His Pro Asn Ser Asp Thr Thr Lys Phe Ser Glu Asn Phe
        50                  55                  60

Lys Thr Arg Val Thr Leu Thr Ile Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125
```

```
<210> SEQ ID NO 34
<211> LENGTH: 111
<212> TYPE: PRT
<213> ORGANISM: Artificial Sequence
<220> FEATURE:
<223> OTHER INFORMATION: Synthetic Sequence_hu7B10-VL-a
<220> FEATURE:
<221> NAME/KEY: DOMAIN
<222> LOCATION: (1)..(111)

<400> SEQUENCE: 34

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
        35                  40                  45

Gln Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Synthetic Sequence_hu7B10-VL-b
<220> FEATURE:
<221> NAME/KEY: DOMAIN
<222> LOCATION: (1)..(111)

<400> SEQUENCE: 35

Asp Ile Val Leu Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
        35                  40                  45

Gln Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Synthetic Sequence_hu7B10-VL-c
<220> FEATURE:
<221> NAME/KEY: DOMAIN
<222> LOCATION: (1)..(111)
```

```
<400> SEQUENCE: 36

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
            35                  40                  45

Gln Leu Leu Ile Tyr Ala Ala Ser Asn Leu Glu Ser Gly Ile Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

<210> SEQ ID NO 37
<211> LENGTH: 108
<212> TYPE: PRT
<213> ORGANISM: Artificial Sequence
<220> FEATURE:
<223> OTHER INFORMATION: Synthetic Sequence_Light chain variable region
      of hu25G7-A
<220> FEATURE:
<221> NAME/KEY: DOMAIN
<222> LOCATION: (1)..(108)

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Pro Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ala Tyr Pro Pro Met
                85                  90                  95

Leu Thr Phe Gly Gly Gly Thr Lys Val Glu Ile Lys
            100                 105

<210> SEQ ID NO 38
<211> LENGTH: 10
<212> TYPE: PRT
<213> ORGANISM: Artificial Sequence
<220> FEATURE:
<223> OTHER INFORMATION: Synthetic Sequence_LCDR1 of hu25G7-A
<220> FEATURE:
<221> NAME/KEY: DOMAIN
<222> LOCATION: (1)..(10)

<400> SEQUENCE: 38

Arg Ala Ser Ser Ser Val Pro Tyr Met Tyr
1               5                   10

<210> SEQ ID NO 39
<211> LENGTH: 7
<212> TYPE: PRT
```

```
<213> ORGANISM: Artificial Sequence
<220> FEATURE:
<223> OTHER INFORMATION: Synthetic Sequence_LCDR2 of hu25G7-B
<220> FEATURE:
<221> NAME/KEY: DOMAIN
<222> LOCATION: (1)..(7)

<400> SEQUENCE: 39

Leu Ala Ser Ser Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic Sequence_LCDR3 of hu25G7-A
<220> FEATURE:
<221> NAME/KEY: DOMAIN
<222> LOCATION: (1)..(11)

<400> SEQUENCE: 40

Gln Gln Trp Arg Ala Tyr Pro Pro Met Leu Thr
1               5                   10

<210> SEQ ID NO 41
<211> LENGTH: 108
<212> TYPE: PRT
<213> ORGANISM: Artificial Sequence
<220> FEATURE:
<223> OTHER INFORMATION: Synthetic Sequence_Light chain variable region
      of hu25G7-B
<220> FEATURE:
<221> NAME/KEY: DOMAIN
<222> LOCATION: (1)..(108)

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Pro Gly Val Pro Pro Leu
            20                  25                  30

Ala Trp Tyr Gln Gln Lys Pro Gly Gln Ala Pro Arg Leu Leu Ile Tyr
        35                  40                  45

Leu Ala Ser Ser Arg Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 42
<211> LENGTH: 10
<212> TYPE: PRT
<213> ORGANISM: Artificial Sequence
<220> FEATURE:
<223> OTHER INFORMATION: Synthetic Sequence_LCDR1 of hu25G7-B

<400> SEQUENCE: 42

Arg Ala Ser Pro Gly Val Pro Pro Leu Ala
1               5                   10

<210> SEQ ID NO 43
<211> LENGTH: 118
```

```
<212> TYPE: PRT
<213> ORGANISM: Artificial Sequence
<220> FEATURE:
<223> OTHER INFORMATION: Synthetic Sequence_Heavy chain variable region
      after hu25G7-A/B VH optimization
<220> FEATURE:
<221> NAME/KEY: DOMAIN
<222> LOCATION: (1)..(118)

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115

<210> SEQ ID NO 44
<211> LENGTH: 445
<212> TYPE: PRT
<213> ORGANISM: Artificial Sequence
<220> FEATURE:
<223> OTHER INFORMATION: Synthetic Sequence_Heavy chain of hu25G7-A and
      hu25G7-B
<220> FEATURE:
<221> NAME/KEY: CHAIN
<222> LOCATION: (1)..(445)

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 45
<211> LENGTH: 215
<212> TYPE: PRT
<213> ORGANISM: Artificial Sequence
<220> FEATURE:
<223> OTHER INFORMATION: Synthetic Sequence_Light chain of hu25G7-A

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Pro Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80
```

```
Asp Phe Ala Val Tyr Tyr Cys Gln Gln Trp Arg Ala Tyr Pro Pro Met
            85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 46
<211> LENGTH: 215
<212> TYPE: PRT
<213> ORGANISM: Artificial Sequence
<220> FEATURE:
<223> OTHER INFORMATION: Synthetic Sequence_Light chain of hu25G7-B

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Pro Gly Val Pro Pro Leu
            20                  25                  30

Ala Trp Tyr Gln Gln Lys Pro Gly Gln Ala Pro Arg Leu Leu Ile Tyr
            35                  40                  45

Leu Ala Ser Ser Arg Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
            85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```

<210> SEQ ID NO 47
<211> LENGTH: 118
<212> TYPE: PRT
<213> ORGANISM: Artificial Sequence
<220> FEATURE:
<223> OTHER INFORMATION: Synthetic Sequence_hu25G7-C VH

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115

<210> SEQ ID NO 48
<211> LENGTH: 445
<212> TYPE: PRT
<213> ORGANISM: Artificial Sequence
<220> FEATURE:
<223> OTHER INFORMATION: Synthetic Sequence_Heavy chain of hu25G7-C
    antibody

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser

-continued

```
              180                  185                  190
Ser Leu Gly Thr Lys Thr Tyr Thr Cys Asn Val Asp His Lys Pro Ser
          195                  200                  205

Asn Thr Lys Val Asp Lys Arg Val Glu Ser Lys Tyr Gly Pro Pro Cys
          210                  215                  220

Pro Pro Cys Pro Ala Pro Glu Phe Leu Gly Gly Pro Ser Val Phe Leu
225                  230                  235                  240

Phe Pro Pro Lys Pro Lys Asp Thr Leu Met Ile Ser Arg Thr Pro Glu
                  245                  250                  255

Val Thr Cys Val Val Val Asp Val Ser Gln Glu Asp Pro Glu Val Gln
                  260                  265                  270

Phe Asn Trp Tyr Val Asp Gly Val Glu Val His Asn Ala Lys Thr Lys
          275                  280                  285

Pro Arg Glu Glu Gln Phe Asn Ser Thr Tyr Arg Val Val Ser Val Leu
          290                  295                  300

Thr Val Leu His Gln Asp Trp Leu Asn Gly Lys Glu Tyr Lys Cys Lys
305                  310                  315                  320

Val Ser Asn Lys Gly Leu Pro Ser Ser Ile Glu Lys Thr Ile Ser Lys
                  325                  330                  335

Ala Lys Gly Gln Pro Arg Glu Pro Gln Val Tyr Thr Leu Pro Pro Ser
                  340                  345                  350

Gln Glu Glu Met Thr Lys Asn Gln Val Ser Leu Thr Cys Leu Val Lys
          355                  360                  365

Gly Phe Tyr Pro Ser Asp Ile Ala Val Glu Trp Glu Ser Asn Gly Gln
          370                  375                  380

Pro Glu Asn Asn Tyr Lys Thr Thr Pro Pro Val Leu Asp Ser Asp Gly
385                  390                  395                  400

Ser Phe Phe Leu Tyr Ser Arg Leu Thr Val Asp Lys Ser Arg Trp Gln
                  405                  410                  415

Glu Gly Asn Val Phe Ser Cys Ser Val Met His Glu Ala Leu His Asn
                  420                  425                  430

His Tyr Thr Gln Lys Ser Leu Ser Leu Ser Leu Gly Lys
          435                  440                  445
```

PHARMACEUTICAL COMPOSITION CONTAINING ANTI-IL-4R ANTIBODY AND USE THEREOF

CROSS-REFERENCE TO RELATED APPLICATIONS

The present application is the national stage of International Patent Application No. PCT/CN2021/076854, filed on Feb. 19, 2021, which claims the benefit of and priority to the Chinese Patent Application No. 202010107765.0, filed Feb. 21, 2020, and Chinese Patent Application No. 202110145455.2, filed on Feb. 2, 2021, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 20, 2022, is named "721013CPUS_126268-5040-US_ST25_Sequence_Listing.TXT" and is approximately 56 kilobytes in size.

TECHNICAL FIELD

The present disclosure relates to the field of pharmaceutical formulations, and in particular to a pharmaceutical composition comprising an anti-IL-4R antibody or an antigen-binding fragment thereof, and use thereof as a medicament for treating immune diseases.

BACKGROUND

The statements herein merely provide background information related to the present disclosure and may not necessarily constitute the prior art.

Allergic diseases are serious medical disorders, including non-life threatening allergic reactions and life threatening allergic diseases. Current methods for treating allergy include allergen avoidance, pharmacological treatment against symptoms, and prophylaxis with allergen-specific immunotherapy.

Interleukin-4 (IL-4, also known as B cell stimulating factor or BSF-1) has been characterized for its ability to stimulate B cell proliferation in response to low concentration of anti-surface immunoglobulin antibodies. IL-4 has been proven to have a wide range of biological activity, including stimulating the growth of T cells, mast cells, granulocytes, megakaryocytes, erythrocytes, etc. IL-4 induces MHC-II expression in resting B cells and enhances secretion of immunoglobulins IgE and IgG1 by activated B cells.

The biological activity of IL-4 is mediated by specific cell surface IL-4 receptors (IL-4Rs). An IL-4 receptor (IL-4R) consists of 802 amino acid residues, and IL-4R is expressed on the surface of T cells, B cells, thymocytes, bone marrow cells, macrophages and mast cells. The $\alpha$ chain of IL-4R is also a part of the IL-13 receptor (IL-13R), and therefore IL-4R may also mediate the biological activity of IL-13. As a novel therapy, a medicament containing an IL-4R antagonist and a composition thereof may be administered to a subject before, during or after exposure to an allergen or development of allergic symptoms.

Formulations with high protein concentration present challenges to the physical and chemical stability of the protein and pose difficulties in the preparation, storage and delivery of the protein formulations. One problem is that the tendency of the protein to form particles during handling and/or storage makes operations during further processing difficult.

Currently, existing patent applications related to anti-IL-4R antibodies and formulations thereof include WO2010053751, WO2001092340, WO2008054606, WO2014031610, CN106604744A, etc.

SUMMARY

Given that the increase in viscosity of a protein formulation has a negative effect from the preparation of the formulation to the delivery of the drug to a patient, there is a need to develop a protein formulation having a relatively high concentration and a suitably low viscosity, wherein the low viscosity is suitable for the preparation, storage and administration of the protein formulation.

The present disclosure provides a pharmaceutical composition comprising an anti-IL-4R antibody or an antigen-binding fragment thereof and a buffer, wherein the buffer is selected from a histidine-acetic acid buffer, and the pharmaceutical composition has a pH of 4.5-6.0, preferably about 4.5-5.5, most preferably about 5.0.

In some embodiments, in the pharmaceutical composition described above, the buffer has a pH of 4.8-5.5, preferably about 5.0.

In some embodiments, the buffer in the pharmaceutical composition has a pH of about 4.5-6.0, preferably 4.5-5.5, preferably about 4.6-5.5, preferably about 4.7-5.5, preferably about 4.8-5.5, 4.9-5.5, preferably about 5.0-5.5, preferably about 5.2-5.5, or preferably about 5.3-5.5, most preferably 5.0, and non-limiting examples include about 4.5, about 4.6, about 4.7, about 4.8, about 4.0, about 5.0, about 5.1, about 5.2, about 5.3, about 5.4 and about 5.5.

In some embodiments, the histidine-acetic acid buffer in the pharmaceutical composition has a concentration of 10 mM to 60 mM, and non-limiting examples include 10 mM to 30 mM, 10 mM to 40 mM, and 20 mM to 50 mM.

In some embodiments, the buffer in the pharmaceutical composition has a concentration of about 10 mM to 50 mM, preferably about 10 mM to 30 mM, and non-limiting examples include 10 mM, 12 mM, 14 mM, 16 mM, 18 mM, 20 mM, 30 mM, 32 mM, 34 mM, 36 mM, 38 mM, 40 mM, 42 mM, 44 mM, 46 mM, 48 mM and 50 mM, and most preferably, the buffer has a concentration of about 20 mM or 50 mM.

In some embodiments, the anti-IL-4R antibody or the antigen-binding fragment thereof in the pharmaceutical composition has a concentration of 100 mg/mL to 200 mg/mL, and non-limiting examples include: 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, and any range therebetween.

In some embodiments, the anti-IL-4R antibody or the antigen-binding fragment thereof in the pharmaceutical composition has a concentration of 100 mg/mL to 180 mg/mL.

In some embodiments, the anti-IL-4R antibody or the antigen-binding fragment thereof in the pharmaceutical composition has a concentration of about 150 mg/mL.

In some embodiments, the anti-IL-4R antibody or the antigen-binding fragment thereof in the pharmaceutical composition has a concentration of 100 mg/mL or greater, preferably 100 mg/mL to 150 mg/mL, and most preferably 120 mg/mL.

In some embodiments, the anti-IL-4R antibody or the antigen-binding fragment thereof in the pharmaceutical composition has a concentration of 100 mg/mL to 140 mg/mL.

In some embodiments, the anti-IL-4R antibody or the antigen-binding fragment thereof in the pharmaceutical composition has a concentration of 100 mg/mL to 120 mg/mL, and non-limiting examples include: 102 mg/mL, 104 mg/mL, 106 mg/mL, 108 mg/mL, 110 mg/mL, 112 mg/mL, 114 mg/mL, 116 mg/mL, 118 mg/mL and 120 mg/mL.

In some embodiments, the pharmaceutical composition further comprises a viscosity modifier, wherein the viscosity modifier is selected from the group consisting of $MgCl_2$, $CaCl_2$, NaF, NaSCN, KCl, $CH_3COONa$, $Na_2SO_4$, NaI, Arg-HCl, arginine, histidine and lysine, preferably selected from the group consisting of $MgCl_2$, histidine and arginine hydrochloride (Arg-HCl).

In some embodiments, the pharmaceutical composition comprises a viscosity modifier. In some cases, the antibody preparation has a high viscosity due to the high concentration of the antibody. In some embodiments, the viscosity modifier is lysine, arginine or histidine. In some embodiments, the viscosity modifier is arginine. In some embodiments, the viscosity modifier comprises a salt form, such as a salt of arginine, lysine or histidine. In some embodiments, the viscosity modifier is an amino acid, such as an L-form amino acid, such as L-arginine, L-lysine or L-histidine. In some embodiments, the viscosity modifier is selected from the group consisting of $MgCl_2$, $CaCl_2$, NaF, NaSCN, KCl, $CH_3COONa$, $Na_2SO_4$, NaI, Arg-HCl, histidine and lysine. In some embodiments, the viscosity modifier is selected from the group consisting of $MgCl_2$, histidine and Arg-HCl.

In some embodiments, the viscosity modifier has a concentration of about 5 mM to about 220 mM. Non-limiting examples include, but are not limited to: 5 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, or 220 mM, and any range therebetween.

In some embodiments, the viscosity modifier has a concentration of about 10 mM to about 220 mM. In some embodiments, the viscosity modifier has a concentration of about 50 mM to about 180 mM.

In some embodiments, the viscosity modifier has a concentration of about 5 mM to about 148 mM.

In some embodiments, the viscosity modifier has a concentration of about 50 mM to about 120 mM.

In some embodiments, the viscosity modifier has a concentration of about 5 mM to about 50 mM. In some embodiments, the viscosity modifier has a concentration of about 10 mM to about 40 mM.

In some embodiments, the pharmaceutical composition has a viscosity of less than 40 mPa·s or less than 30 mPa·s.

In some embodiments, the pharmaceutical composition has a viscosity of less than 20 mPa·s.

In some embodiments, the viscosity modifier in the pharmaceutical composition has a concentration of 50 mM to 148 mM, preferably 85 mM to 120 mM.

In some embodiments, the viscosity modifier is:
i) 5 mM to 220 mM arginine hydrochloride;
ii) 5 mM to 100 mM histidine; or
iii) 5 mM to 90 mM $MgCl_2$.
In some embodiments, the viscosity modifier is:
i) 10 mM to 220 mM arginine hydrochloride;
ii) 10 mM to 100 mM histidine; or
iii) 10 mM to 90 mM $MgCl_2$.

In some embodiments, the viscosity modifier is 5 mM to 220 mM arginine hydrochloride, and non-limiting examples include, but are not limited to: 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, or 220 mM, and any range therebetween.

In some embodiments, the viscosity modifier is 5 mM to 100 mM histidine, and non-limiting examples include 10 mM, 20 mM, 30 mM, 40 mM, 50 mM, 60 mM, 70 mM, 80 mM, 90 mM or 100 mM, and any range therebetween.

In some embodiments, the viscosity modifier is 10 mM to 90 mM $MgCl_2$, and non-limiting examples include 10 mM, 20 mM, 30 mM, 40 mM, 50 mM, 60 mM, 70 mM, 80 mM or 90 mM, and any range therebetween.

In some embodiments, the anti-IL-4R antibody or the antigen-binding fragment thereof in the pharmaceutical composition has a concentration of 100 mg/mL to 200 mg/mL, and the viscosity modifier is selected from the group consisting of $MgCl_2$, histidine and arginine hydrochloride.

In some embodiments, when the anti-IL-4R antibody or the antigen-binding fragment thereof in the pharmaceutical composition has a concentration of 100 mg/mL to 200 mg/mL, the viscosity modifier is selected from the group consisting of 50 mM to 200 mM $MgCl_2$, histidine and arginine hydrochloride.

In some embodiments, when the anti-IL-4R antibody or the antigen-binding fragment thereof in the pharmaceutical composition has a concentration of 100 mg/mL to 200 mg/mL, the viscosity modifier is selected from the group consisting of 50 mM to 90 mM $MgCl_2$, 50 mM to 100 mM histidine and 10 mM to 200 mM, preferably 50 mM to 180 mM, arginine hydrochloride.

In some embodiments, the anti-IL-4R antibody or the antigen-binding fragment thereof in the pharmaceutical composition has a concentration of 120 mg/mL to 150 mg/mL, and the viscosity modifier is selected from the group consisting of 50 mM to 90 mM $MgCl_2$, 50 mM to 100 mM histidine and 50 mM to 120 mM arginine hydrochloride.

In some embodiments, the anti-IL-4R antibody or the antigen-binding fragment thereof in the pharmaceutical composition has a concentration of 100 mg/mL to 140 mg/mL, and the viscosity modifier is selected from the group consisting of 5 mM to 50 mM histidine, arginine hydrochloride and $MgCl_2$, and is preferably 10 mM to 40 mM histidine, arginine hydrochloride or $MgCl_2$.

In some embodiments, the anti-IL-4R antibody or the antigen-binding fragment thereof in the pharmaceutical composition has a concentration of 100 mg/mL to 140 mg/mL, and the viscosity modifier is 30 mM histidine, arginine hydrochloride or $MgCl_2$.

In some embodiments, the anti-IL-4R antibody or the antigen-binding fragment thereof in the pharmaceutical composition has a concentration of 100 mg/mL to 120 mg/mL, and the viscosity modifier is selected from the group consisting of 5 mM to 50 mM histidine, arginine hydrochloride and $MgCl_2$, and is preferably 10 mM to 40 mM histidine, arginine hydrochloride or $MgCl_2$.

In some embodiments, the viscosity modifier in the pharmaceutical composition is selected from the group consisting of 50 mM to 90 mM $MgCl_2$, 85 mM to 100 mM histidine and 90 mM to 120 mM arginine hydrochloride.

In some embodiments, the viscosity modifier in the pharmaceutical composition is selected from the group consisting of 5 mM to 50 mM histidine, arginine hydrochloric acid and $MgCl_2$, and is preferably 10 mM to 40 mM histidine, arginine hydrochloric acid or $MgCl_2$.

In some embodiments, the pharmaceutical composition further comprises a surfactant, preferably polysorbate 80.

In some embodiments, the surfactant in the pharmaceutical composition has a concentration of 0.1 mg/mL to 1.2 mg/mL, preferably 0.8 mg/mL.

In some embodiments, the surfactant in the pharmaceutical composition has a concentration of about 0.1 mg/mL to 1.0 mg/mL, preferably 0.2 mg/mL to 0.8 mg/mL, more preferably 0.4 mg/mL to 0.8 mg/mL, and non-limiting examples include, but are not limited to, 0.2 mg/mL, 0.3 mg/mL, 0.4 mg/mL, 0.45 mg/mL, 0.5 mg/mL, 0.55 mg/mL, 0.6 mg/mL, 0.7 mg/mL, 0.8 mg/mL, 0.9 mg/mL, 1.0 mg/mL and any range therebetween, and most preferably the surfactant has a concentration of 0.8 mg/mL.

In some embodiments, the pharmaceutical composition described above comprises:
  (a) 100 mg/mL to 200 mg/mL anti-IL-4R antibody or antigen-binding fragment thereof; (b) 10 mM to 30 mM histidine-acetic acid buffer, pH 4.5-6.0; (c) 50 mM to 220 mM viscosity modifier; and (d) 0.4 mg/mL to 1.2 mg/mL polysorbate 80, wherein the viscosity modifier is selected from the group consisting of: $MgCl_2$, $CaCl_2$, NaF, NaSCN, KCl, $CH_3COONa$, $Na_2SO_4$, NaI, arginine, arginine hydrochloride, histidine and lysine; preferably the viscosity modifier is selected from the group consisting of $MgCl_2$, histidine and arginine hydrochloride.

In some embodiments, the pharmaceutical composition further comprises a stabilizer, wherein the stabilizer is preferably selected from the group consisting of trehalose and sucrose, and is preferably sucrose.

In some embodiments, the stabilizer in the pharmaceutical composition has a concentration of 20 mg/mL to 70 mg/mL, preferably 40 mg/mL to 60 mg/mL, and most preferably 58 mg/mL.

In some embodiments, the stabilizer in the pharmaceutical composition has a concentration of 40 mg/mL to 70 mg/mL.

In some embodiments, sugar in the pharmaceutical composition described above is about 50 mg/mL to about 60 mg/mL, preferably 55 mg/mL to 60 mg/mL, and non-limiting examples include 50 mg/mL, 51 mg/mL, 52 mg/mL, 53 mg/mL, 54 mg/mL, 55 mg/mL, 56 mg/mL, 57 mg/m, 58/mL, 59 mg/mL and 60 mg/mL.

In some embodiments, the pharmaceutical composition comprises:
  (a) 100 mg/mL to 150 mg/mL anti-IL-4R antibody or antigen-binding fragment thereof; (b) 10 mM to 30 mM histidine-acetic acid buffer, pH 4.5-5.5; (c) 80 mM to 148 mM, or 5 mM to 50 mM viscosity modifier; (d) 0.4 mg/mL to 1.2 mg/mL polysorbate 80; and (e) 40 mg/mL to 60 mg/mL sucrose, wherein the pharmaceutical composition has a viscosity of less than 20 mPa·s.

In some embodiments, the pharmaceutical composition comprises:
  (a) 100 mg/mL to 150 mg/mL anti-IL-4R antibody or antigen-binding fragment thereof; (b) 10 mM to 30 mM histidine-acetic acid buffer, pH 4.5-5.5; (c) 80 mM to 148 mM viscosity modifier; and (d) 0.4 mg/mL to 1.2 mg/mL polysorbate 80.

In some embodiments, the pharmaceutical composition comprises:
  (a) 100 mg/mL to 120 mg/mL anti-IL-4R antibody or antigen-binding fragment thereof; (b) 10 mM to 20 mM histidine-acetic acid buffer, pH 4.5-5.5; (c) 10 mM to 40 mM histidine; (d) 0.4 mg/mL to 1.0 mg/mL polysorbate 80; and (e) 50 mg/mL to 60 mg/mL sucrose.

In some embodiments, the pharmaceutical composition comprises:
  (a) 100 mg/mL to 140 mg/mL anti-IL-4R antibody or antigen-binding fragment thereof; (b) 10 mM to 30 mM histidine-acetic acid buffer, pH 4.5-5.5; (c) 10 mM to 40 mM viscosity modifier; (d) 0.4 mg/mL to 1.2 mg/mL polysorbate 80; and (e) 40 mg/mL to 70 mg/mL sucrose; or,
  (a) 100 mg/mL to 200 mg/mL anti-IL-4R antibody or antigen-binding fragment thereof; (b) 10 mM to 30 mM histidine-acetic acid buffer, pH 4.5-5.5; (c) 40 mM to 220 mM viscosity modifier; and (d) 0.4 mg/mL to 1.2 mg/mL polysorbate 80;
  wherein the viscosity modifier is selected from the group consisting of: $MgCl_2$, $CaCl_2$, NaF, NaSCN, KCl, $CH_3COONa$, $Na_2SO_4$, NaI, arginine, arginine hydrochloride, histidine and lysine.

In some embodiments, the pharmaceutical composition comprises:
  (a) 100 mg/mL to 140 mg/mL anti-IL-4R antibody or antigen-binding fragment thereof; (b) 10 mM to 30 mM histidine-acetic acid buffer, pH 4.5-5.5; (c) 10 mM to 40 mM viscosity modifier; (d) 0.4 mg/mL to 1.2 mg/mL polysorbate 80; and (e) 40 mg/mL to 70 mg/mL sucrose, wherein the viscosity modifier is histidine, arginine hydrochloride or $MgCl_2$; or
  (a) 100 mg/mL to 180 mg/mL anti-IL-4R antibody or antigen-binding fragment thereof; (b) 10 mM to 30 mM histidine-acetic acid buffer, pH 4.5-5.5; (c) 40 mM to 90 mM $MgCl_2$; and (d) 0.4 mg/mL to 1.2 mg/mL polysorbate 80; or
  (a) 100 mg/mL to 180 mg/mL anti-IL-4R antibody or antigen-binding fragment thereof; (b) 10 mM to 30 mM histidine-acetic acid buffer, pH 4.5-5.5; (c) 50 mM to 100 mM histidine; and (d) 0.4 mg/mL to 1.2 mg/mL polysorbate 80; or
  (a) 100 mg/mL to 180 mg/mL anti-IL-4R antibody or antigen-binding fragment thereof; (b) 10 mM to 30 mM histidine-acetic acid buffer, pH 4.5-5.5; (c) 50 mM to 200 mM arginine hydrochloride; and (d) 0.4 mg/mL to 1.2 mg/mL polysorbate 80.

In some embodiments, the pharmaceutical composition comprises:
  (a) 100 mg/mL to 140 mg/mL anti-IL-4R antibody or antigen-binding fragment thereof; (b) 10 mM to 30 mM histidine-acetic acid buffer, pH 4.5-5.5; (c) 10 mM to 40 mM histidine; (d) 0.4 mg/mL to 1.2 mg/mL polysorbate 80; and (e) 40 mg/mL to 70 mg/mL sucrose.

In some embodiments, the pharmaceutical composition comprises:
  (a) 120 mg/mL anti-IL-4R antibody or antigen-binding fragment thereof; (b) 20 mM histidine-acetic acid buffer, pH 4.5-5.5; (c) 30 mM histidine; (d) 0.8 mg/mL polysorbate 80; and (e) 58 mg/mL sucrose.

In some embodiments, the pharmaceutical composition comprises:
  (a) 120 mg/mL anti-IL-4R antibody or antigen-binding fragment thereof; (b) 20 mM histidine-acetic acid buffer, pH about 5.0; (c) 30 mM histidine; (d) 0.8 mg/mL polysorbate 80; and (e) 58 mg/mL sucrose.

In some embodiments, the pharmaceutical composition comprises:
  (a) 120 mg/mL anti-IL-4R antibody or antigen-binding fragment thereof; (b) 50 mM histidine-acetic acid buffer, pH about 5.0; (c) 0.8 mg/mL polysorbate 80; and (d) 58 mg/mL sucrose.

In some embodiments, the pharmaceutical composition comprises:

(a) about 100 mg/mL to 180 mg/mL anti-IL-4R antibody or antigen-binding fragment thereof; (b) about 10 mM to 30 mM histidine-acetic acid buffer, pH about 4.5-5.5; (c) about 0.4 mg/mL to 1.2 mg/mL polysorbate 80; and (d) about 90 mM to 200 mM arginine hydrochloride.

In some embodiments, the pharmaceutical composition comprises:

(a) about 150 mg/mL anti-IL-4R antibody or antigen-binding fragment thereof; (b) about 20 mM histidine-acetic acid buffer, pH about 5.0; (c) about 0.8 mg/mL polysorbate 80; and (d) about 120 mM arginine hydrochloride.

In some embodiments, the pharmaceutical composition comprises:

(a) 100 mg/mL to 140 mg/mL anti-IL-4R antibody or antigen-binding fragment thereof; (b) 20 mM to 60 mM histidine-acetic acid buffer, pH 4.5-5.5; (c) 0.4 mg/mL to 1.2 mg/mL polysorbate 80; and (d) 40 mg/mL to 70 mg/mL sucrose.

In some embodiments, the pharmaceutical composition comprises:

(a) 100 mg/mL to 140 mg/mL anti-IL-4R antibody or antigen-binding fragment thereof; (b) 50 mM histidine-acetic acid buffer, pH 4.5-5.5; (c) 0.4 mg/mL to 1.2 mg/mL polysorbate 80; and (d) 40 mg/mL to 70 mg/mL sucrose.

In some embodiments, the pharmaceutical composition comprises:

(a) 100 mg/mL to 120 mg/mL anti-IL-4R antibody or antigen-binding fragment thereof; (b) 20 mM to 60 mM histidine-acetic acid buffer, pH 5.0-5.5; (c) 0.4 mg/mL to 1.2 mg/mL polysorbate 80; and (d) 50 mg/mL to 60 mg/mL sucrose; wherein preferably, the pharmaceutical composition comprises:

(a) 120 mg/mL anti-IL-4R antibody or antigen-binding fragment thereof; (b) 50 mM histidine-acetic acid buffer, pH 5.0-5.5; (c) 0.8 mg/mL polysorbate 80; and (d) 58 mg/mL sucrose.

In some embodiments, the pharmaceutical composition comprises:

(a) 120 mg/mL anti-IL-4R antibody or antigen-binding fragment thereof; (b) 50 mM histidine-acetic acid buffer, pH about 5.0; (c) 0.8 mg/mL polysorbate 80; and (d) 58 mg/mL sucrose.

In some embodiments, the anti-IL-4R antibody or the antigen-binding fragment thereof in the pharmaceutical composition comprises a heavy chain variable region and a light chain variable region shown below:

(i) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 6, SEQ ID NO: 7 and SEQ ID NO: 8, respectively;

(ii) a heavy chain variable region comprising an HCDR1, an HCDR2 and an HCDR3 set forth in SEQ ID NO: 11, SEQ ID NO: 12 and SEQ ID NO: 13, respectively; and a light chain variable region comprising an LCDR1, an LCDR2 and an LCDR3 set forth in SEQ ID NO: 14, SEQ ID NO: 15 and SEQ ID NO: 16, respectively;

(iii) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 38, SEQ ID NO: 7 and SEQ ID NO: 40, respectively; or (iv) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 42, SEQ ID NO: 39 and SEQ ID NO: 8, respectively.

In some embodiments, the anti-IL-4R antibody or the antigen-binding fragment thereof in the pharmaceutical composition comprises:

a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 38, SEQ ID NO: 7 and SEQ ID NO: 40, respectively.

In some embodiments, the anti-IL-4R antibody or the antigen-binding fragment thereof in the pharmaceutical composition comprises a heavy chain variable region and a light chain variable region shown below:

(v) the heavy chain variable region has a sequence set forth in SEQ ID NO: 1 or having at least 90% identity to SEQ ID NO: 1, and the light chain variable region has a sequence set forth in SEQ ID NO: 2 or having at least 90% identity to SEQ ID NO: 2;

(vi) the heavy chain variable region has a sequence set forth in SEQ ID NO: 9 or having at least 90% identity to SEQ ID NO: 9, and the light chain variable region has a sequence set forth in SEQ ID NO: 10 or having at least 90% identity to SEQ ID NO: 10;

(vii) the heavy chain variable region has a sequence set forth in SEQ ID NO: 25, 26, 27, 43 or 47 or having at least 90% identity to SEQ ID NO: 25, 26, 27, 43 or 47, and the light chain variable region has a sequence set forth in SEQ ID NO: 28, 29, 30, 37 or 41 or having at least 90% identity to SEQ ID NO: 28, 29, 30, 37 or 41; or (viii) the heavy chain variable region has a sequence set forth in SEQ ID NO: 31, 32 or 33 or having at least 90% identity to SEQ ID NO: 31, 32 or 33, and the light chain variable region has a sequence set forth in SEQ ID NO: 34, 35 or 36 or having at least 90% identity to SEQ ID NO: 34, 35 or 36;

Preferably, the anti-IL-4R antibody or the antigen-binding fragment thereof comprises a heavy chain variable region and a light chain variable region shown below:

(IX) the heavy chain variable region has a sequence set forth in SEQ ID NO: 43 or having at least 90% identity to SEQ ID NO: 43, and the light chain variable region has a sequence set forth in SEQ ID NO: 37 or having at least 90% identity to SEQ ID NO: 37; or (X) the heavy chain variable region has a sequence set forth in SEQ ID NO: 43 or having at least 90% identity to SEQ ID NO: 43, and the light chain variable region has a sequence set forth in SEQ ID NO: 41 or having at least 90% identity to SEQ ID NO: 41; or (XI) the heavy chain variable region has a sequence set forth in SEQ ID NO: 47 or having at least 90% identity to SEQ ID NO: 47, and the light chain variable region has a sequence set forth in SEQ ID NO: 41 or having at least 90% identity to SEQ ID NO: 41.

In some embodiments, the heavy chain variable region of the anti-IL-4R antibody or the antigen-binding fragment thereof in the pharmaceutical composition has a sequence set forth in SEQ ID NO: 43, and the light chain variable region thereof has a sequence set forth in SEQ ID NO: 37.

In some embodiments, the anti-IL-4R antibody or the antigen-binding fragment thereof in the pharmaceutical composition comprises a constant region. In some embodiments, the anti-IL-4R antibody or the antigen-binding fragment thereof comprises a constant region of human κ and λ chains or variants thereof, and further comprises a heavy chain constant region of human IgG1, IgG2, IgG3 or IgG4 or variants thereof, such as IgG4-S228P or IgG4-234A/235A mutant.

In some embodiments, the anti-IL-4R antibody or the antigen-binding fragment thereof in the pharmaceutical composition comprises a heavy chain and a light chain shown below:

a heavy chain set forth in SEQ ID NO: 17 and a light chain set forth in SEQ ID NO: 18; or a heavy chain set forth in SEQ ID NO: 19 and a light chain set forth in SEQ ID NO: 20; or a heavy chain set forth in SEQ ID NO: 44 and a light chain set forth in SEQ ID NO: 45; or a heavy chain set forth in SEQ ID NO: 44 and a light chain set forth in SEQ ID NO: 46; or a heavy chain set forth in SEQ ID NO: 48 and a light chain set forth in SEQ ID NO: 46.

In some embodiments, the anti-IL-4R antibody or the antigen-binding fragment thereof in the pharmaceutical composition comprises a heavy chain set forth in SEQ ID NO: 44 and a light chain set forth in SEQ ID NO: 45.

The present application also relates to an anti-IL-4R antibody, wherein a heavy chain variable region thereof has a sequence set forth in SEQ ID NO: 47 or having at least 90% identity to SEQ ID NO: 47, and a light chain variable region thereof has a sequence set forth in SEQ ID NO: 41 or having at least 90% identity to SEQ ID NO: 41.

The present application also relates to an anti-IL-4R antibody comprising a heavy chain set forth in SEQ ID NO: 48 and a light chain set forth in SEQ ID NO: 46.

In one embodiment, the pharmaceutical composition comprises: (a) 100 mg/mL hu25G7-A antibody; (b) 20 mM histidine-acetic acid buffer, pH 4.5-6.0; and (c) 0.1 mg/mL polysorbate 80.

In one embodiment, the pharmaceutical composition comprises: (a) 100 mg/mL hu25G7-A antibody; and (b) 20 mM histidine-acetic acid buffer, pH 4.5.

In one embodiment, the pharmaceutical composition comprises: (a) 100 mg/mL hu25G7-A antibody; (b) 20 mM histidine-acetic acid buffer, pH 4.5; and (c) 0.1 mg/mL polysorbate 80.

In one embodiment, the pharmaceutical composition comprises: (a) 100 mg/mL hu25G7-A antibody; and (b) 20 mM histidine-acetic acid buffer, pH 5.0.

In one embodiment, the pharmaceutical composition comprises: (a) 100 mg/mL hu25G7-A antibody; (b) 20 mM histidine-acetic acid buffer, pH 5.0; and (c) 0.1 mg/mL polysorbate 80.

In one embodiment, the pharmaceutical composition comprises: (a) 100 mg/mL hu25G7-A antibody; (b) 20 mM histidine-acetic acid buffer, pH 6.0; and (c) 0.1 mg/mL polysorbate 80.

In one embodiment, the pharmaceutical composition comprises: (a) 100 mg/mL hu25G7-A antibody; and (b) 20 mM histidine-acetic acid buffer, pH 5.5.

In one embodiment, the pharmaceutical composition comprises: (a) 100 mg/mL hu25G7-A antibody; (b) 20 mM histidine-acetic acid buffer, pH 5.5; and (c) 0.1 mg/mL polysorbate 80.

In one embodiment, the pharmaceutical composition comprises: (a) 100-150 mg/mL hu25G7-A antibody; and (b) 20 mM histidine-acetic acid buffer, pH 5.0-5.5.

In one embodiment, the pharmaceutical composition comprises: (a) 120 mg/mL hu25G7-A antibody; (b) 20 mM histidine-acetic acid buffer, pH 5.0; and (c) 122 mM NaCl.

In one embodiment, the pharmaceutical composition comprises: (a) 120 mg/mL hu25G7-A antibody; (b) 20 mM histidine-acetic acid buffer, pH 5.0; and (c) 85 mM $MgCl_2$.

In one embodiment, the pharmaceutical composition comprises: (a) 120 mg/mL hu25G7-A antibody; (b) 20 mM histidine-acetic acid buffer, pH 5.0; and (c) 148 mM $CaCl_2$).

In one embodiment, the pharmaceutical composition comprises: (a) 120 mg/mL hu25G7-A antibody; (b) 20 mM histidine-acetic acid buffer, pH 5.0; and (c) 124 mM KCl.

In one embodiment, the pharmaceutical composition comprises: (a) 120 mg/mL hu25G7-A antibody; (b) 20 mM histidine-acetic acid buffer, pH 5.0; and (c) 86 mM $CH_3COONa$.

In one embodiment, the pharmaceutical composition comprises: (a) 120 mg/mL hu25G7-A antibody; (b) 20 mM histidine-acetic acid buffer, pH 5.0; and (c) 96 mM $Na_2SO_4$.

In one embodiment, the pharmaceutical composition comprises: (a) 120 mg/mL hu25G7-A antibody; (b) 20 mM histidine-acetic acid buffer, pH 5.0; and (c) 113 mM NaI.

In one embodiment, the pharmaceutical composition comprises: (a) 120 mg/mL hu25G7-A antibody; (b) 20 mM histidine-acetic acid buffer, pH 5.0; and (c) 74 mM NaF.

In one embodiment, the pharmaceutical composition comprises: (a) 120 mg/mL hu25G7-A antibody; (b) 20 mM histidine-acetic acid buffer, pH 5.0; and (c) 112 mM NaSCN.

In one embodiment, the pharmaceutical composition comprises: (a) 120 mg/mL hu25G7-A antibody; (b) 20 mM histidine-acetic acid buffer, pH 5.0; and (c) 120 mM Arg-HCl.

In one embodiment, the pharmaceutical composition comprises: (a) 120 mg/mL hu25G7-A antibody; (b) 20 mM histidine-acetic acid buffer, pH 5.0; and (c) 118 mM lysine.

In one embodiment, the pharmaceutical composition comprises: (a) 120 mg/mL hu25G7-A antibody; (b) 20 mM histidine-acetic acid buffer, pH 5.0; and (c) 93 mM histidine.

In one embodiment, the pharmaceutical composition comprises: (a) 120 mg/mL hu25G7-A antibody; (b) 20 mM histidine-acetic acid buffer, pH 5.0; and (c) 207 mM proline.

In one embodiment, the pharmaceutical composition comprises: (a) 150 mg/mL hu25G7-A antibody; (b) 20 mM histidine-acetic acid buffer, pH 5.0; and (c) 85 mM $MgCl_2$.

In one embodiment, the pharmaceutical composition comprises: (a) 150 mg/mL hu25G7-A antibody; (b) 20 mM histidine-acetic acid buffer, pH 5.0; and (c) 148 mM $CaCl_2$).

In one embodiment, the pharmaceutical composition comprises: (a) 150 mg/mL hu25G7-A antibody; (b) 20 mM histidine-acetic acid buffer, pH 5.0; and (c) 93 mM histidine.

In one embodiment, the pharmaceutical composition comprises: (a) 150 mg/mL hu25G7-A antibody; (b) 20 mM histidine-acetic acid buffer, pH 5.0; and (c) 50 mM $MgCl_2$.

In one embodiment, the pharmaceutical composition comprises: (a) 150 mg/mL hu25G7-A antibody; (b) 20 mM histidine-acetic acid buffer, pH 5.0; and (c) 90 mM $MgCl_2$.

In one embodiment, the pharmaceutical composition comprises: (a) 150 mg/mL hu25G7-A antibody; (b) 20 mM histidine-acetic acid buffer, pH 5.0; and (c) 90 mM $CaCl_2$.

In one embodiment, the pharmaceutical composition comprises: (a) 150 mg/mL hu25G7-A antibody; (b) 20 mM histidine-acetic acid buffer, pH 5.0; and (c) 148 mM $CaCl_2$.

In one embodiment, the pharmaceutical composition comprises: (a) 150 mg/mL hu25G7-A antibody; (b) 20 mM histidine-acetic acid buffer, pH 5.0; and (c) 90 mM histidine.

In one embodiment, the pharmaceutical composition comprises: (a) 150 mg/mL hu25G7-A antibody; (b) 20 mM histidine-acetic acid buffer, pH 5.0; and (c) 120 mM Arg-HCl.

In one embodiment, the pharmaceutical composition comprises: (a) 150 mg/mL hu25G7-A antibody; (b) 20 mM histidine-acetic acid buffer, pH 5.0; (c) 90 mM $MgCl_2$; and (d) 0.1 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 90 mM $MgCl_2$; and (d) 1 mg/mL polysorbate 80.

In one embodiment, the pharmaceutical composition comprises: (a) 120 mg/mL hu25G7-A antibody; (b) 20 mM histidine-acetic acid buffer, pH 5.0; (c) 122 mM NaCl; and (d) 0.1 mg/mL polysorbate 80.

In one embodiment, the pharmaceutical composition comprises: (a) 120 mg/mL hu25G7-A antibody; (b) 20 mM histidine-acetic acid buffer, pH 5.0; (c) 122 mM NaCl; and (d) 1 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 90 mM histidine; and (d) 0.1 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 90 mM histidine; and (d) 1 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 120 mM Arg-HCl; and (d) 0.1 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 120 mM Arg-HCl; and (d) 1 mg/mL polysorbate 80.

In one embodiment, the pharmaceutical composition comprises: (a) about 165 mg/mL hu25G7-A antibody; (b) about 20 mM histidine-acetic acid buffer, pH 5.0; and (c) about 50 mM to 90 mM $MgCl_2$.

In one embodiment, the pharmaceutical composition comprises: (a) about 165 mg/mL hu25G7-A antibody; (b) about 20 mM histidine-acetic acid buffer, pH 5.0; and (c) about 50 mM to 90 mM histidine.

In one embodiment, the pharmaceutical composition comprises: (a) about 165 mg/mL hu25G7-A antibody; (b) about 20 mM histidine-acetic acid buffer, pH 5.0; and (c) about 90 mM to 200 mM Arg-HCl.

In one embodiment, the pharmaceutical composition comprises: (a) 150 mg/mL hu25G7-A antibody; (b) 20 mM histidine-acetic acid buffer, pH 5.0; (c) 120 mM Arg-HCl; and (d) 0.8 mg/mL polysorbate 80.

In one embodiment, the pharmaceutical composition comprises: (a) 150 mg/mL hu25G7-A antibody; (b) 20 mM histidine-acetic acid buffer, pH 4.8; (c) 87 mM histidine; and (d) 0.8 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 100 mM histidine; and (d) 0.8 mg/mL polysorbate 80.

In one embodiment, the pharmaceutical composition comprises: (a) 150 mg/mL hu25G7-A antibody; (b) 20 mM histidine-acetic acid buffer, pH 5.0; (c) 30 mM histidine; (d) 0.8 mg/mL polysorbate 80; and (e) 41.8 mg/mL sucrose.

In one embodiment, the pharmaceutical composition comprises: (a) 120 mg/mL hu25G7-A antibody; (b) 20 mM histidine-acetic acid buffer, pH 5.0; (c) 30 mM histidine; (d) 0.8 mg/mL polysorbate 80; and (e) 58 mg/mL sucrose.

In one embodiment, the pharmaceutical composition comprises: (a) 120 mg/mL hu25G7-A antibody; (b) 20 mM histidine-acetic acid buffer, pH 5.2; (c) 30 mM histidine; (d) 0.4 mg/mL polysorbate 80; and (e) 50 mg/mL sucrose.

In one embodiment, the pharmaceutical composition comprises: (a) 120 mg/mL hu25G7-A antibody; (b) 50 mM histidine-acetic acid buffer, pH about 5.0; (c) 0.8 mg/mL polysorbate 80; and (d) 58 mg/mL sucrose.

In one embodiment, the pharmaceutical composition comprises: (a) 120 mg/mL to 150 mg/mL hu25G7-A antibody; (b) 20 mM histidine-acetic acid buffer, pH 5.0; (c) 30 mM to 100 mM histidine; (d) 0.8 mg/mL polysorbate 80; and (e) 41.8 mg/mL to 58 m/mL sucrose.

In one embodiment, the pharmaceutical composition comprises: (a) 150 mg/mL hu25G7-A antibody; (b) 20 mM histidine-acetic acid buffer, pH 5.0; (c) 120 mM arginine hydrochloride; and (d) 0.8 mg/mL polysorbate 80.

In one embodiment, the pharmaceutical composition comprises: (a) 100 mg/mL to 140 mg/mL hu25G7-A antibody; (b) 50 mM histidine-acetic acid buffer, pH 4.5-5.5; (c) 0.4 mg/mL to 1.2 mg/mL polysorbate 80; and (d) about 58 mg/mL sucrose.

In one embodiment, the pharmaceutical composition comprises: (a) 100 mg/mL to 140 mg/mL hu25G7-A antibody; (b) 50 mM histidine-acetic acid buffer, pH 4.8-5.5; (c) 0.4 mg/mL to 1.2 mg/mL polysorbate 80; and (d) about 58 mg/mL sucrose.

In one embodiment, the pharmaceutical composition comprises: (a) 100 mg/mL to 120 mg/mL hu25G7-A antibody; (b) 50 mM histidine-acetic acid buffer, pH 4.5-5.5; (c) 0.4 mg/mL to 0.8 mg/mL polysorbate 80; and (d) about 58 mg/mL sucrose.

In one embodiment, the pharmaceutical composition comprises: (a) about 132 mg/mL hu25G7-A antibody; (b) 50 mM histidine-acetic acid buffer, pH about 5.5; (c) about 0.4 mg/mL polysorbate 80; and (d) about 58 mg/mL sucrose.

In one embodiment, the pharmaceutical composition comprises: (a) about 100 mg/mL hu25G7-A antibody; (b) 50 mM histidine-acetic acid buffer, pH about 5.0; (c) about 0.8 mg/mL polysorbate 80; and (d) about 58 mg/mL sucrose.

In one embodiment, the pharmaceutical composition comprises: (a) about 100 mg/mL hu25G7-A antibody; (b) 50 mM histidine-acetic acid buffer, pH about 4.5; (c) about 0.4 mg/mL polysorbate 80; and (d) about 58 mg/mL sucrose.

In one embodiment, the pharmaceutical composition comprises: (a) about 140 mg/mL hu25G7-A antibody; (b) 50 mM histidine-acetic acid buffer, pH about 4.5; (c) about 0.8 mg/mL polysorbate 80; and (d) about 58 mg/mL sucrose.

In one embodiment, the pharmaceutical composition comprises: (a) about 120 mg/mL hu25G7-A antibody; (b) 50 mM histidine-acetic acid buffer, pH about 4.5; (c) about 1.2 mg/mL polysorbate 80; and (d) about 58 mg/mL sucrose.

In one embodiment, the pharmaceutical composition comprises: (a) about 100 mg/mL hu25G7-A antibody; (b) 50 mM histidine-acetic acid buffer, pH about 5; (c) about 1.2 mg/mL polysorbate 80; and (d) about 58 mg/mL sucrose.

In one embodiment, the pharmaceutical composition comprises: (a) about 100 mg/mL hu25G7-A antibody; (b) 50 mM histidine-acetic acid buffer, pH about 5.5; (c) about 0.4 mg/mL polysorbate 80; and (d) about 58 mg/mL sucrose.

In one embodiment, the pharmaceutical composition comprises: (a) about 120 mg/mL hu25G7-A antibody; (b) 50 mM histidine-acetic acid buffer, pH about 5.5; (c) about 1.2 mg/mL polysorbate 80; and (d) about 58 mg/mL sucrose.

In one embodiment, the pharmaceutical composition comprises: (a) about 120 mg/mL hu25G7-A antibody; (b) 50 mM histidine-acetic acid buffer, pH about 5; (c) about 0.8 mg/mL polysorbate 80; and (d) about 58 mg/mL sucrose.

The present disclosure also provides a method for preparing the pharmaceutical composition, which comprises a step of buffer-exchanging a stock solution of the anti-IL-4R antibody or the antigen-binding fragment thereof.

The present disclosure also provides a lyophilized formulation comprising an anti-IL-4R antibody or an antigen-binding fragment thereof, wherein the lyophilized formulation is obtained by lyophilizing the pharmaceutical composition described above.

The present disclosure also provides a lyophilized formulation comprising an anti-IL-4R antibody or an antigen-binding fragment thereof, wherein the lyophilized formulation is obtained by diluting the pharmaceutical composition described above and then lyophilizing.

The present disclosure also provides a lyophilized formulation comprising an anti-IL-4R antibody or an antigen-binding fragment thereof, wherein the lyophilized formulation is obtained by subjecting the pharmaceutical composition described above to 1-fold, 2-fold or 3-fold dilution and then lyophilizing.

The present disclosure also provides a reconstituted solution comprising an anti-IL-4R antibody or an antigen-binding fragment thereof, wherein the reconstituted solution is obtained by reconstituting the lyophilized formulation described above.

In some embodiments, the reconstituted solution comprises the following ingredients:

(a) 120 mg/mL anti-IL-4R antibody or antigen-binding fragment thereof (b) 50 mM histidine-acetic acid buffer, pH about 5.0; (c) 0.4 mg/mL polysorbate 80; and (e) 50 mg/mL sucrose.

In one embodiment, the reconstituted solution comprises: (a) about 120 mg/mL hu25G7-A antibody; (b) about 50 mM histidine-acetic acid buffer; (c) about 0.8 mg/mL polysorbate 80; and (d) about 58 mg/mL sucrose, and the pH of the pharmaceutical composition is about 5.3.

In one embodiment, the reconstituted solution comprises: (a) about 150 mg/mL hu25G7-A antibody; (b) about 20 mM histidine-acetic acid buffer; (c) about 0.8 mg/mL polysorbate 80; and (d) about 120 mM arginine hydrochloride, and the pH of the pharmaceutical composition is about 5.3.

The present disclosure also provides an article of manufacture comprising a container containing the pharmaceutical composition or lyophilized formulation or reconstituted solution described above.

The present disclosure also provides a method for treating or preventing an immune disease or disorder, which comprises administering to a subject a therapeutically effective amount of the pharmaceutical composition, the lyophilized formulation or the reconstituted solution described above, wherein preferably, the immune disease is an IL-4R-mediated disease or disorder.

In some embodiments, the immune disease or disorder is selected from the group consisting of: asthma, nasal polyps, chronic sinusitis, allergic skin disorder, eosinophilic esophagitis, chronic obstructive pulmonary disease, allergic rhinitis, arthritis, inflammatory diseases, allergic reaction, autoimmune lymphoproliferative syndrome, autoimmune hemolytic anemia, Barrett's esophagus, autoimmune uveitis, tuberculosis, and renal disease; preferably, the disease or disorder is asthma or allergic skin disorder.

In some embodiments, the immune disease or disorder is asthma.

In other embodiments, the immune disease or disorder is allergic skin disorder.

The present disclosure also provides use of the pharmaceutical composition, the lyophilized formulation, the reconstituted solution of the lyophilized formulation, or the article of manufacture described above in preparing a medicament for treating or preventing an immune disease or disorder, wherein preferably, the immune disease or disorder is an IL-4R-mediated disease or disorder.

The pharmaceutical composition, the lyophilized formulation, the reconstituted solution of the lyophilized formulation, or the article of manufacture of the present disclosure can be used as a medicament, preferably as a medicament for treating or preventing an immune disease or disorder, more preferably as a medicament for treating an IL-4R-mediated disease or disorder.

The pharmaceutical composition, the lyophilized formulation, the reconstituted solution of the lyophilized formulation, or the article of manufacture in the present disclosure can be used as a medicament, preferably as a medicament for treating or preventing an immune disease or disorder, wherein more preferably, the immune disease or disorder is selected from the group consisting of: asthma, nasal polyps, chronic sinusitis, allergic skin disorder, eosinophilic esophagitis, chronic obstructive pulmonary disease, allergic rhinitis, arthritis, inflammatory diseases, allergic reaction, autoimmune lymphoproliferative syndrome, autoimmune hemolytic anemia, Barrett's esophagus, autoimmune uveitis, tuberculosis, and renal disease; preferably, the disease or disorder is asthma or allergic skin disorder.

In the present application, histidine can act both as a buffer and as a viscosity modifier, and therefore, the final content of histidine in the pharmaceutical composition is the sum of the content of histidine in the buffer and the content of histidine that is further added to reduce the viscosity. For example, if 90 mM histidine is further added to a 20 mM histidine-acetic acid buffer pH 5.0 to increase its viscosity-lowering effect, the final concentration of histidine in the pharmaceutical composition is 110 mM, and the pH of the pharmaceutical composition is about 5.0.

DETAILED DESCRIPTION

Terms

Figure 1:
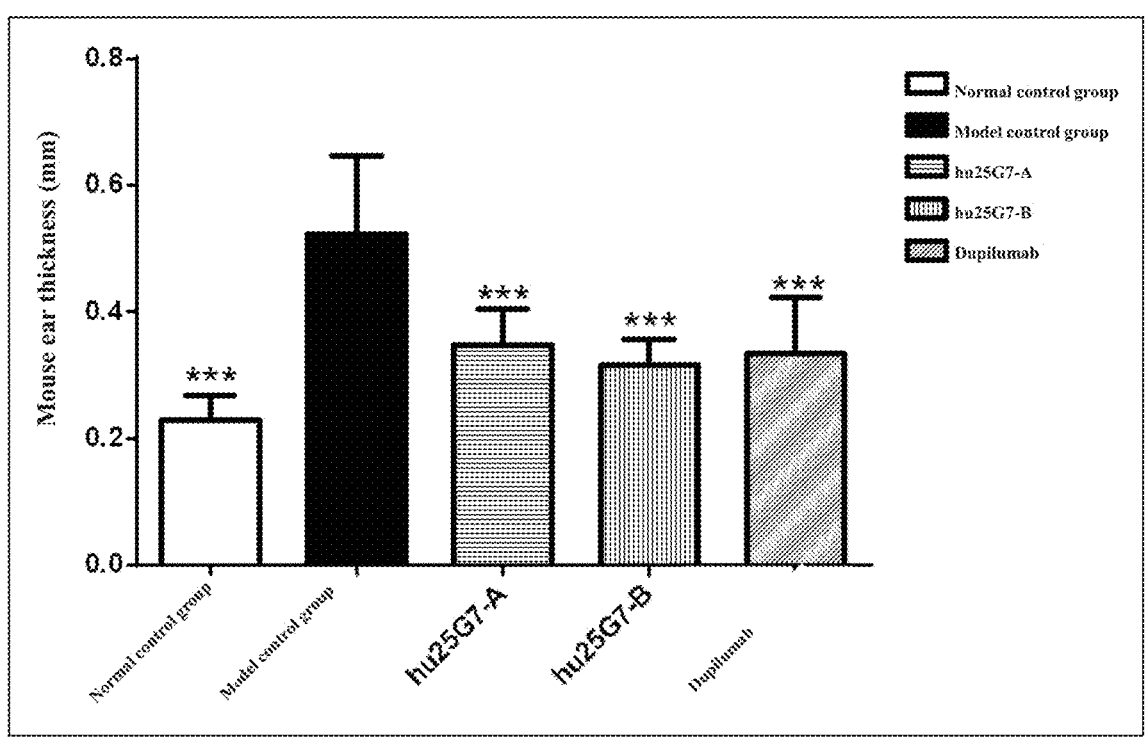
FIG. 1 shows the results of the experiment on the effect of anti-IL-4R antibody on dermatitis in mice. In mouse dermatitis models, after sensitization with acetone, humanized antibodies hu25G7-A and hu25G7-B and a positive reference antibody dupilumab were administered subcutaneously: the administration was performed twice a week, and the ear thickness of the mice was measured on day 27. The results show that compared with the control group, hu25G7-A, hu25G7-B and dupilumab were all effective in reducing the ear thickness of the mice, and hu25G7-B showed a better effect than dupilumab.

In order to facilitate the understanding of the present disclosure, some technical and scientific terms are specifically defined below. Unless otherwise specifically defined elsewhere herein, all other technical and scientific terms used herein have the meanings generally understood by those of ordinary skill in the art to which the present disclosure belongs.

The application PCT/CN2019/102169 is incorporated herein by reference in its entirety.

"Buffer" refers to a buffer that resists changes in pH by the action of its acid-base conjugate components. Examples of buffers that control the pH in an appropriate range include acetate, succinate, gluconate, histidine salt, oxalate, lactate, phosphate, citrate, tartrate, fumarate, glycylglycine and other organic acid buffers.

A "histidine salt buffer" is a buffer comprising histidine ions. Examples of histidine salt buffers include histidine-hydrochloride buffer, histidine-acetate buffer, histidine-phosphate buffer, histidine-sulfate buffer, and the like, and the histidine-acetate buffer is preferred. The histidine-acetate buffer is prepared with histidine and acetic acid, and is also known as histidine-acetic acid (His-AA) buffer.

A "citrate buffer" is a buffer comprising citrate ions. Examples of citrate buffers include citric acid-sodium citrate buffer, citric acid-potassium citrate buffer, citric acid-calcium citrate buffer, citric acid-magnesium citrate buffer, and the like. The preferred citrate buffer is the citric acid-sodium citrate buffer.

A "succinate buffer" is a buffer comprising succinate ions. Examples of succinate buffers include succinic acid-sodium succinate buffer, succinic acid-potassium succinate buffer, succinic acid-calcium succinate buffer, and the like. The preferred succinate buffer is the succinic acid-sodium succinate buffer.

A "phosphate buffer" is a buffer comprising phosphate ions. Examples of phosphate buffers include disodium hydrogen phosphate-sodium dihydrogen phosphate buffer, disodium hydrogen phosphate-potassium dihydrogen phosphate buffer, disodium hydrogen phosphate-citric acid buffer, and the like. The preferred phosphate buffer is the disodium hydrogen phosphate-sodium dihydrogen phosphate buffer.

An "acetate buffer" is a buffer comprising acetate ions. Examples of acetate buffers include acetic acid-sodium acetate buffer, acetic acid histidine salt buffer, acetic acid-potassium acetate buffer, acetic acid-calcium acetate buffer, acetic acid-magnesium acetate buffer, and the like. The preferred acetate buffer is the acetic acid-sodium acetate buffer.

"Pharmaceutical composition" refers to a mixture comprising one or more antibodies or antigen-binding fragments thereof described herein and other chemical components, for example, physiological/pharmaceutically acceptable carriers and excipients. The purpose of the pharmaceutical composition is to maintain the stability of the active ingredient of the antibody and promote the administration to an organism, which facilitates the absorption of the active ingredient, thereby exerting biological activity.

As used herein, a "pharmaceutical composition" and a "formulation" are not mutually exclusive.

Unless otherwise specified, the solvent of the solution form of the pharmaceutical composition described herein is aqueous solution.

"Exchange" refers to the exchange of a solvent system that solubilizes an antibody protein. For example, a high-salt or hypertonic solvent system comprising the antibody protein is exchanged, by physical operations, with a buffer system of a stable formulation, such that the antibody protein is present in the stable formulation. The physical operations include, but are not limited to, ultrafiltration, dialysis or reconstitution following centrifugation.

"Lyophilized formulation" refers to a formulation or a pharmaceutical composition obtained by vacuum lyophilization of a pharmaceutical composition or a formulation in liquid or solution form.

"Saccharide" of the present disclosure comprises the general composition $(CH_2O)_n$ and derivatives thereof, including monosaccharides, disaccharides, trisaccharides, polysaccharides, sugar alcohols, reducing sugars, non-reducing sugars, etc. It may be selected from the group consisting of glucose, sucrose, trehalose, lactose, fructose, maltose, dextran, glycerin, erythritol, glycerol, arabitol, xylitol, sorbitol, mannitol, mellibiose, melezitose, raffinose, mannotriose, stachyose, maltose, lactulose, maltulose, glucitol, maltitol, lactitol, iso-maltulose, etc. The preferred saccharide is non-reducing disaccharide, the more preferred saccharide is trehalose or sucrose, and the most preferred saccharide is sucrose.

The surfactant of the present disclosure may be selected from the group consisting of polysorbate 20, polysorbate 80, poloxamer, Triton, sodium dodecyl sulfonate, sodium lauryl sulfonate, sodium octyl glycoside, lauryl-/myristyl-/linoleyl-/stearyl-sulfobetaine, lauryl-/myristyl-/linoleyl-/stearyl-sarcosine, linoleyl-/myristyl-/cetyl-betaine, lauramido propyl-/cocaramide propyl-/linoleinamide propyl-/myristylamide propyl-/palmitamide propyl-/isostearamide propyl-betaine, myristylamide propyl-/palmitamide propyl-/isostearamide propyl-dimethylamine, sodium methyl cocoyl, sodium methyl oleyl taurate, polyethylene glycol, polypropylene glycol, copolymer of ethylene and propylene glycol, and the like. The preferred surfactant is polysorbate 80 or polysorbate 20, and the more preferred one is polysorbate 80.

The term "viscosity" may be "kinematic viscosity" or "absolute viscosity". "Kinematic viscosity" is a measure of the resistance of a fluid to flow under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the kinematic viscosity of the second fluid is twice that of the first one. "Absolute viscosity", sometimes called dynamic or simple viscosity, is the product of kinematic viscosity and fluid density (Absolute Viscosity=Kinematic Viscosity×Density). Kinematic viscosity is expressed in $L^2/T$, where L is the length and T is the time. Usually kinematic viscosity is expressed in centistokes (cSt). The SI unit of kinematic viscosity is $mm^2/s$, which is 1 cSt. Absolute viscosity is expressed in centipoise (cP). The SI unit of absolute viscosity is the milliPascal-second (mPa-s), where 1 cP=1 mPa-s.

The terms "about" and "approximately" as used herein mean that a numerical value is within an acceptable error range for the particular value determined by one of ordinary skill in the art, and the numerical value depends in part on how the value is measured or determined (i.e., the limits of the measurement system). For example, "about" can mean within 1 or more than 1 standard deviation per the practice in the art. Alternatively, "about" or "comprising essentially" can mean a range of ±20%, ±15%, ±10% or ±5% of the specific numerical values indicated thereafter. Furthermore, particularly for biological systems or processes, the term can mean up to an order of magnitude or up to 5-fold of a numerical value. When a particular value is provided in the present application and claims, unless otherwise stated, the meaning of "about" or "comprising essentially" should be assumed to be within an acceptable error range for that particular value.

The pharmaceutical composition described herein can achieve a stable effect: the antibody therein substantially retains its physical stability, and/or chemical stability and/or biological activity after storage. Preferably, the pharmaceutical composition substantially retains its physical and chemical stability and its biological activity after storage. The storage period is generally selected based on a predetermined shelf life of the pharmaceutical composition. There are a variety of analytical techniques currently available for measuring protein stability, and the stability after storage for a selected period of time at a selected temperature can be measured.

A stable pharmaceutical antibody formulation is one in which no significant change is observed under the following conditions: stored at refrigeration temperature (2-8° C.) for at least 3 months, preferably 6 months, more preferably 1 year, and even more preferably up to 2 years. In addition, stable liquid formulations include liquid formulations that exhibit desirable features after storage at temperatures including 25° C. for periods including 1 month, 3 months and 6 months. Typical acceptable criteria for stability are as follows: typically, no more than about 10%, preferably no more than about 5%, of antibody monomer is degraded as measured by SEC-HPLC. The pharmaceutical antibody formulation is a pale yellow, nearly colorless and transparent liquid, or colorless, or transparent to slightly opalescent, by visual analysis. The concentration, pH and osmolality of the formulation have no more than ±10% change. Typically, no more than about 10%, preferably no more than about 5%, of decrease is observed. Typically, no more than about 10%, preferably no more than about 5%, of aggregation is formed.

An antibody "retains its physical stability" in a pharmaceutical formulation if it shows no significant increase in aggregation, precipitation and/or denaturation upon visual examination of color and/or clarity, or as measured by UV light scattering, size exclusion chromatography (SEC) and dynamic light scattering (DLS). Changes of protein conformation can be evaluated by fluorescence spectroscopy (which determines the protein tertiary structure) and by FTIR spectroscopy (which determines the protein secondary structure).

An antibody "retains its chemical stability" in a pharmaceutical formulation if it shows no significant chemical change. Chemical stability can be assessed by detecting and quantifying chemically changed forms of the protein. Degradation processes that often change the chemical structure of proteins include hydrolysis or clipping (evaluated by methods such as size exclusion chromatography and SDS-PAGE), oxidation (evaluated by methods such as peptide mapping in conjunction with mass spectroscopy or MALDI/TOF/MS), deamidation (evaluated by methods such as ion-exchange chromatography, capillary isoelectric focusing, peptide mapping, and isoaspartic acid measurement), and isomerization (evaluated by measuring the isoaspartic acid content, peptide mapping, etc.).

An antibody "retains its biological activity" in a pharmaceutical formulation if the biological activity of the antibody at a given time is within a predetermined range of the biological activity exhibited at the time the pharmaceutical formulation was prepared. The biological activity of an antibody can be determined, for example, by an antigen-binding assay.

"Human IL-4R" (hIL-4R) refers to a human cytokine receptor that specifically binds to interleukin-4 (IL-4) or IL-4Rα.

The three-letter and single-letter codes for amino acids used herein are described as in *J. Biol. Chem,* 243, p 3558 (1968).

The term "antibody (Ab)" includes any antigen-binding molecule or molecular complex comprising at least one complementarity determining region (CDR) that specifically binds to or interacts with a particular antigen (or epitope thereof, e.g., IL-4R antigen or epitope thereof). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region (CH). The heavy chain constant region comprises three regions (domains), CH1, CH2 and CH3. Each light chain comprises a light chain variable region (abbreviated herein as LCVR or VL) and a light chain constant region (CL). The light chain constant region comprises one region (domain, CL). The VH and VL regions can be further subdivided into hypervariable regions, which are called complementarity determining regions (CDRs) and are interspersed with regions that are more conserved, which are called framework regions (FRs). Each VH and VL is composed of three CDRs and four FRs arranged from amino-terminus to carboxy-terminus in the following order: FR1, CDR1, FR2, CDR2, FR3, CDR3, FR4.

The FRs of the anti-IL-4R antibody (or the antigen-binding fragment thereof) may be identical to the human germline sequences, or may be naturally or artificially modified. The antibodies may be of different subclasses, for example, an IgG (e.g., IgG1, IgG2, IgG3, or IgG4 subclass), IgA1, IgA2, IgD, IgE or IgM antibody.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (such as monovalent nanobodies and bivalent nanobodies), small modular immunopharmaceuticals (SMIPs), and shark variable IgNAR regions, are also encompassed within the expression "antigen-binding fragment" as used herein.

An antigen-binding fragment of an antibody will typically comprise at least one variable region. The variable region may be a region of any size or amino acid composition and will generally comprise a CDR that is adjacent to or in the frame of one or more framework sequences. In antigen-binding fragments having a VH region and a VL region, the VH and VL regions may be situated relative to one another in any suitable arrangement. For example, the variable region may be dimeric and contain VH-VL or VL-VH dimers.

In certain embodiments, in any configuration of variable and constant regions of an antigen-binding fragment, the variable and constant regions may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant regions in a single polypeptide molecule. Moreover, an antigen-binding fragment of the present disclosure may comprise a homo-dimer or hetero-dimer (or other multimers) having a variable region and a constant region that are noncovalently linked to each other and/or linked to one or more monomer VH or VL regions (e.g., by a disulfide bond).

The "murine antibody" used herein is a mouse- or rat-derived monoclonal antibody prepared according to the knowledge and skills in the art. During the preparation, a test subject is injected with an antigen, and then hybridomas expressing antibodies with desired sequences or functional properties are isolated. When the test subject of injection is a mouse, the antibody produced is a mouse-derived antibody, and when the test subject of injection is a rat, the antibody produced is a rat-derived antibody.

The "chimeric antibody" is an antibody formed by fusing the variable region of an antibody of a first species (such as a mouse) with the constant region of an antibody of a second species (such as a human). A chimeric antibody is established by firstly establishing hybridoma secreting a monoclonal antibody of a first species, then cloning a variable region gene from the hybridoma cells, cloning a constant region gene of the antibody of a second species as required, connecting the variable region gene of the first species and the constant region gene of the second species to form a chimeric gene, inserting the chimeric gene into an expression vector, and finally expressing chimeric antibody molecules in a eukaryotic system or prokaryotic system. In a preferred embodiment of the present disclosure, the light chain of the chimeric antibody further comprises a light chain constant region of human κ and λ chains or variants thereof. The antibody heavy chain of the chimeric antibody further comprises a heavy chain constant region of human IgG1, IgG2, IgG3 or IgG4 or a variant thereof, preferably a heavy chain constant region of human IgG1, IgG2 or IgG4, or an IgG1, IgG2 or IgG4 heavy chain constant region variant using an amino acid mutation (e.g., a YTE mutation, a back mutation, an L234A and/or an L235A mutation, or an S228P mutation).

The term "humanized antibody", including CDR-grafted antibodies, refers to an antibody produced by grafting CDR sequences of an antibody derived from animals (e.g., a murine antibody) into a framework region of a human antibody variable region. The humanized antibody can overcome the heterogeneous reaction induced by the chimeric antibody because of carrying a large amount of heterogeneous protein ingredients. Such framework sequences can be obtained from public DNA databases or published references that include germline antibody gene sequences. For example, germline DNA sequences of genes of the human heavy and light chain variable regions can be found in the "VBase" human germline sequence database (available from http://www.vbase2.org/), as well as in Kabat, E. A. et al., 1991 *Sequences of Proteins of Immunological Interest,* 5th ed. In order to avoid the decrease in activity caused by the decrease in immunogenicity, the FR sequence in human antibody variable region can be subjected to a small amount of back mutation to maintain activity. The humanized antibodies of the present disclosure also include humanized antibodies which were further subjected to CDR affinity maturation by phage display.

Because of the contact residues of the antigen, grafting of CDRs can result in reduced affinity of the resulting antibody or antigen-binding fragment thereof for an antigen due to framework residues in contact with the antigen. Such interactions may be the result of hypermutation of somatic cells. Thus, it may still be necessary to graft such donor framework amino acids to the framework of the humanized antibody. Amino acid residues from a non-human antibody or an antigen-binding fragment thereof that are involved in antigen binding can be identified by examining the sequence and structure of variable regions of animal monoclonal antibodies. Residues in the CDR donor framework that differ from the germline can be considered related. If the closest germline cannot be determined, the sequence can be compared to a consensus sequence of a subclass or a consensus sequence of animal antibody sequences with a high percentage of similarity. Rare framework residues are thought to be the result of somatic hypermutation and thus play an important role in binding.

In an embodiment of the present disclosure, the antibody or the antigen-binding fragment thereof may further comprise a light chain constant region of a human or murine κ and λ chains or a variant thereof, or further comprises a heavy chain constant region of human or murine IgG1, IgG2, IgG3 or IgG4 or a variant thereof.

The "conventional variant" of the human antibody heavy chain constant region and the human antibody light chain constant region refers to the variant of heavy chain constant region or light chain constant region derived from humans that has been disclosed in the prior art and does not change the structure and function of the antibody variable region. Exemplary variants include IgG1, IgG2, IgG3 or IgG4 heavy chain constant region variants with site-directed modifications and amino acid substitutions in the heavy chain constant region. Specific substitutions are, for example, a YTE mutation, an L234A and/or L235A mutation, or an S228P mutation, or mutations to obtain a knob-into-hole structure (so that the antibody heavy chain has a combination of knob-Fc and hole-Fc) known in the art. These mutations have been confirmed to make the antibody have new properties, but do not change the function of the antibody variable region.

The "human antibody" and "human-derived antibody" can be used interchangeably and can be either an antibody derived from humans or an antibody obtained from a transgenic organism that is "engineered" to produce specific human antibodies in response to antigenic stimulation and can be produced by any method known in the art. In certain techniques, elements of the human heavy and light chain gene loci are introduced into cell strains in which endogenous heavy and light chain gene loci are subjected to targeted disruption. The transgenic organism can synthesize human antibodies specific to antigens, and the organism can be used to produce human antibody-secreting hybridomas. A human antibody can also be an antibody in which the heavy and light chains are encoded by nucleotide sequences derived from one or more human DNA sources. Fully human antibodies can also be constructed by gene or chromosome transfection methods and phage display techniques, or by in-vitro activated B cells, all of which are known in the art.

"Monoclonal antibody" refers to an antibody obtained from a population of substantially homogeneous antibodies, i.e., the individual antibodies that constitute the population recognize the same and/or bind to the same epitope, except for possible variant antibodies (e.g., containing naturally occurring mutations or mutations arising during production of a monoclonal antibody formulation, such variants generally being present in minor amounts). Each monoclonal antibody of the monoclonal antibody preparation (formulation) is directed against a single determinant on the antigen.

Thus, the modifier "monoclonal" indicates the characteristic of the antibody as obtained from the population of substantially homogeneous antibodies, and is not to be construed as requiring production of the antibody by any particular method. For example, the monoclonal antibodies used in accordance with the present disclosure may be prepared by a variety of techniques, including but not limited to the hybridoma methods, recombinant DNA methods, phage-display methods, and methods utilizing transgenic animals containing all or part of the human immunoglobulin gene loci, and such methods and other exemplary methods for preparing monoclonal antibodies are described herein.

Furthermore, although the two domains of the Fv fragment, VL and VH, are encoded by separate genes, they can be linked by a synthetic linker using a recombinant method, such that it is capable of generating a single protein chain in which the VL and VH regions are paired to form monovalent molecules (referred to as single chain Fv (scFv); see, e.g., Bird et al., (1988) *Science,* 242: 423-426; and Huston et al., (1988) *Proc.Natl.Acad.Sci* USA 85: 5879-5883). Such single-chain antibodies are also intended to be included in the term "antigen-binding fragment" of an antibody. Such antibody fragments are obtained using conventional techniques known to those skilled in the art, and screened for utility in the same manner as for intact antibodies. Antigen-binding moieties may be produced by recombinant DNA techniques or by enzymatic or chemical cleavage of intact immunoglobulins.

The antigen-binding fragment may also be incorporated into a single chain molecule comprising a pair of tandem Fv fragments (VH-CH1-VH—CH1) that, together with the complementary light chain polypeptide, form a pair of antigen-binding regions (Zapata et al., 1995 *Protein Eng.* 8(10): 1057-1062; and U.S. Pat. No. 5,641,870).

Fab is an antibody fragment that has a molecular weight of about 50,000 Da, has antigen-binding activity, and is obtained by treating an IgG antibody with a protease papain (which cleaves the amino acid residue at position 224 of the H chain), in which about half of the N-terminal side of the H chain and the entire L chain are joined together by disulfide bonds.

F(ab')$_2$ is an antibody fragment having a molecular weight of about 100,000 Da, having antigen-binding activity and comprising two Fab regions linked at the hinge position, and it is obtained by digesting a portion below two disulfide bonds in the IgG hinge region with the pepsase.

Fab' is an antibody fragment having a molecular weight of about 50,000 Da and having antigen-binding activity, and it is obtained by cleaving the disulfide bond in the hinge region of the F(ab')$_2$ described above. Fab' can be produced by treating F(ab')$_2$ that specifically recognizes and binds to an antigen with a reducing agent such as dithiothreitol.

In addition, the Fab' can be expressed by inserting DNA encoding the Fab' fragment of the antibody into a prokaryotic expression vector or a eukaryotic expression vector and introducing the vector into a prokaryote or a eukaryote.

The term "single chain antibody", "single chain Fv" or "scFv" refers to a molecule comprising an antibody heavy chain variable domain (or region; VH) and an antibody light chain variable domain (or region; VL) linked by a linker. Such scFv molecules may have a general formula: NH$_2$-VL-linker-VH—COOH or NH$_2$—VH-linker-VL-COOH. Suitable linkers in the prior art consist of repeated GGGGS amino acid sequences or variants thereof, for example, 1-4 (including 1, 2, 3 or 4) repeated variants (Holliger et al. (1993), *Proc. Natl. Acad. Sci. USA* 90:6444-6448). Other linkers that can be used in the present disclosure are described in: Alfthan et al. (1995), *Protein Eng.* 8:725-731; Choi et al. (2001), *Eur. J. Immuno.* 31:94-106; Hu et al. (1996), *Cancer Res.* 56:3055-3061; Kipriyanov et al. (1999), *J. Mol. Biol.* 293:41-56; and Roovers et al. (2001), *Cancer Immunother.* 50:51-59.

A diabody is an antibody fragment in which scFv is dimerized, and is an antibody fragment with bivalent antigen-binding activity. In the bivalent antigen-binding activity, the two antigens can be identical or different.

dsFv is obtained by linking polypeptides in which one amino acid residue in each VH and VL is substituted with a cysteine residue via disulfide bonds between the cysteine residues. The amino acid residues substituted with cysteine residues can be selected according to known methods (*Protein Engineering,* 7:697 (1994)) based on prediction of the three-dimensional structure of the antibody.

In some embodiments of the present disclosure, an antigen-binding fragment can be produced by the following steps: obtaining cDNA encoding VH and/or VL of the monoclonal antibody of the present disclosure which specifically recognizes and binds to an antigen and cDNA encoding other desired domains, constructing DNA encoding the antigen-binding fragment, inserting the DNA into a prokaryotic expression vector or a eukaryotic expression vector, and then introducing the expression vector into a prokaryote or a eukaryote to express the antigen-binding fragment.

"Fc region" can be a native sequence Fc region or a variant Fc region. Although the boundaries of the Fc region of an immunoglobulin heavy chain may vary, the human IgG heavy chain Fc region is usually defined to stretch from an amino acid residue at position Cys226, or from Pro230, to the carboxyl-terminus thereof. The numbering of residues in the Fc region is that of the EU index as in Kabat. Kabat et al., Sequences of Proteins of Immunological Interest, 5th ed., Public Health Service, National Institutes of Health, Bethesda, Md., 1991. The Fc region of an immunoglobulin typically has two constant region domains CH2 and CH3.

The term "amino acid difference" or "amino acid mutation" refers to the presence of amino acid changes or mutations in the variant protein or polypeptide compared with the original protein or polypeptide, including occurrence of 1 or more amino acid insertions, deletions or substitutions on the basis of the original protein or polypeptide.

The "variable region" of an antibody refers to the variable region of an antibody light chain (VL) or the variable region of an antibody heavy chain (VH), alone or in combination. As is known in the art, the variable regions of the heavy and light chains each consist of 4 framework regions (FRs) connected by 3 complementarity determining regions (CDRs), also known as hypervariable regions. The CDRs in each chain are held tightly together by the FRs and, together with the CDRs from the other chain, contribute to the formation of the antigen-binding site of the antibody. There are at least two techniques for determining CDRs: (1) an approach based on cross-species sequence variability (i.e., Kabat et al., Sequences of Proteins of Immunological Interest, (5th ed., 1991, National Institutes of Health, Bethesda MD)); and (2) an approach based on crystallographic studies of antigen-antibody complexes (Al-Lazikani et al., *J. Molec. Biol.* 273:927-948 (1997)). As used herein, a CDR may refer to CDRs defined by either approach or by a combination of both approaches.

The term "antibody framework" or "FR" refers to a portion of a variable domain VL or VH, which serves as a framework for the antigen-binding loops (CDRs) of the variable domain. It is essentially a variable domain without CDRs.

The term "complementarity determining region" or "CDR" refers to one of the six hypervariable regions within the variable domain of an antibody which primarily contribute to antigen binding. In general, there are three CDRs (HCDR1, HCDR2 and HCDR3) in each heavy chain variable region and three CDRs (LCDR1, LCDR2 and LCDR3) in each light chain variable region. The amino acid sequence boundaries of the CDRs can be determined using any of a variety of well-known schemes, including "Kabat" numbering scheme (see Kabat et al. (1991), "Sequences of Proteins of Immunological Interest", 5th ed., Public Health Service, National Institutes of Health, Bethesda, MD), "Chothia" numbering scheme (Martin, A C R. Protein Sequence and Structure Analysis of Antibody Variable Domains[J]. 2001) and ImMunoGenTics (IMGT) numbering scheme (see Lefranc, M. P. et al., *Dev. Comp. Immunol.,* 27, 55-77 (2003)), and the like. For example, for the classical format, according to the Kabat scheme, the CDR amino acid residues in the heavy chain variable domain (VH) are numbered as 31-35(HCDR1), 50-65(HCDR2) and 95-102(HCDR3); the CDR amino acid residues in the light chain variable domain (VL) are numbered as 24-34(LCDR1), 50-56 (LCDR2) and 89-97(LCDR3). According to the Chothia scheme, the CDR amino acids in VH are numbered as 26-32(HCDR1), 52-56(HCDR2) and 95-102(HCDR3); and amino acid residues in VL are numbered as 24-34(LCDR1), 50-56(LCDR2) and 89-97(LCDR3). According to the CDR definitions by combining both the Kabat scheme and the Chothia scheme, the CDR is composed of amino acid residues 26-35(HCDR1), 50-65(HCDR2) and 95-102 (HCDR3) in the human VH and amino acid residues 24-34 (LCDR1), 50-56(LCDR2) and 89-97(LCDR3) in the human VL. According to the IMGT scheme, the CDR amino acid residues in VH are roughly numbered as 27-38(CDR1), 56-65(CDR2) and 105-117(CDR3), and the CDR amino acid residues in VL are roughly numbered as 27-38(CDR1), 56-65(CDR2) and 105-117(CDR3). According to the IMGT scheme, the CDRs of the antibody can be determined using the program IMGT/DomainGap Align.

"Antibody constant region domain" refers to domains derived from the constant regions of the light and heavy chains of an antibody, including CL and the CH1, CH2, CH3 and CH4 domains derived from different classes of antibodies.

"Epitope" or "antigenic determinant" refers to a site on an antigen to which an immunoglobulin or antibody specifically binds. Epitopes typically comprise at least 3, 4, 5, 6, 7, 8, 9, 10, 11, 12, 13, 14 or 15 contiguous or non-contiguous amino acids in a unique spatial conformation. See, e.g., Epitope Mapping Protocols in Methods in Molecular Biology, volume 66, G. E. Morris, Ed. (1996).

The terms "specific binding", "selective binding", "selectively bind to" and "specifically bind to" refer to the binding of an antibody to an epitope on a predetermined antigen.

The term "affinity" refers to the strength of the interaction between an antibody and an antigen at a single epitope. Within each antigenic site, the variable region of the antibody "arm" interacts with the antigen at numerous amino acid sites through weak non-covalent forces; the more the interaction, the stronger the affinity. As used herein, the term "high affinity" for an antibody or an antigen-binding fragment thereof (e.g., a Fab fragment) refers to an antibody or an antigen-binding fragment having a $K_D$ of $1E^{-9}M$ or less (e.g., a $K_D$ of $1E^{-10}M$ or less, a $K_D$ of $1E^{-11}M$ or less, a $K_D$ of $1E^{-12}M$ or less, a $K_D$ of $1E^{-13}M$ or less or a $K_D$ of $1E^{-14}M$ or less).

The term "KD" or "$K_D$" refers to the dissociation equilibrium constant for specific antibody-antigen interaction. Typically, the antibody binds to the antigen with a dissociation equilibrium constant (KD) of less than about $1E^{-8}M$ (e.g., less than about $1E^{-9}M$, $1E^{-10}M$ or $1E^{-11}M$ or less), for example, as determined in a BIACORE instrument using surface plasmon resonance (SPR) technique. The smaller the KD value, the greater the affinity.

The term "nucleic acid molecule" refers to a DNA molecule and an RNA molecule. The nucleic acid molecule may be a single-stranded or double-stranded DNA molecule or RNA molecule, for example, a double-stranded DNA or mRNA. A nucleic acid is "operably linked" when it is placed into a functional relationship with another nucleic acid sequence. For example, a promoter or enhancer is operably linked to a coding sequence if it affects the transcription of the coding sequence.

The term "vector" means a construct capable of delivering one or more genes or sequences of interest and preferably expressing the same in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Methods of producing and purifying antibodies and antigen-binding fragments are well known in the art, for example, those described in chapters 5-8 and 15 of *Antibodies: A Laboratory Manual*, Cold Spring Harbor Press. For example, mice can be immunized with an antigen or a fragment thereof, and the obtained antibody can be renatured and purified, and amino acid sequencing can be performed by using conventional methods. Antigen-binding fragments can likewise be prepared using conventional methods. The antibody or antigen-binding fragment described herein is genetically engineered to contain one or more additional human FRs in the non-human CDRs. Human FR germline sequences can be obtained by aligning the IMGT human antibody variable region germline gene database with MOE software, or obtained from Immunoglobulin Journal, 20011SBN012441351.

The term "host cell" refers to a cell into which an expression vector has been introduced. Host cells may include bacterial, microbial, plant or animal cells. Bacteria susceptible to transformation include members of the Enterobacteriaceae family, such as strains of *Escherichia coli* or *Salmonella*; members of the Bacillaceae family, such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line), HEK293 cells (non-limiting examples include HEK293E cells) and NS0 cells.

The engineered antibody or antigen-binding fragment can be prepared and purified using conventional methods. For example, cDNA sequences encoding the heavy and light chains can be cloned and recombined into a GS expression vector. Recombinant immunoglobulin expression vectors can be stably transfected into CHO cells. As an optional prior art, mammalian expression systems may result in glycosylation of antibodies, particularly at the highly conserved N-terminus site of the Fc region. Stable clones are obtained by expression of antibodies specifically binding to the antigen. Positive clones are expanded in a serum-free medium of a bioreactor to produce antibodies. The culture with the secreted antibody can be purified using conventional techniques. for example, using an protein A or protein G Sepharose FF column containing an adjusted buffer. Non-specifically bound fractions are washed away. The bound antibody is eluted using pH gradient method, and the antibody fragments are detected using SDS-PAGE and collected. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

"Administer" "administration", "giving" and "treating", when applied to animals, humans, experimental subjects, cells, tissues, organs or biological fluid, refer to the contact that provides an exogenous drug, a therapeutic agent, a diagnostic agent, composition or manual operation (e.g., "euthanasia" in the examples) to the animals, humans, subjects, cells, tissues, organs or biological fluid. "Giving" and "treating" can refer to, for example, therapeutic, pharmacokinetic, diagnostic, research and experimental methods. The treatment of the cells comprises contacting the reagent with the cells and contacting the reagent with fluid, where the fluid is in contact with the cells. "Giving" and "treating" also refer to treating, e.g., cells by reagents, diagnosis, binding compositions or by another cell in vitro and ex vivo. "Treating", when applied to humans, veterinary or research subjects, refers to therapeutic treatment, preventive or prophylactic measures, and research and diagnostic applications.

"Treating" or "treatment" refers to administering a therapeutic agent, such as a composition comprising any one of the compounds of the examples of the present disclosure, either internally or externally to a patient (or a subject) having (or suspected to have or susceptible to) one or more symptoms of a disease on which the therapeutic agent is known to have a therapeutic effect. Typically, the therapeutic agent is administered in an amount effective to alleviate one or more symptoms of the disease in the treated patient (or the subject) or population to induce regression of such symptoms or to inhibit the progression of such symptoms to any clinically measurable degree. The amount of therapeutic agent effective to alleviate any particular symptom of the disease (also referred to as the "therapeutically effective amount") may vary depending on factors such as the disease state, age and weight of the patient (or the subject), and the ability of the drug to produce a desired therapeutic effect in the patient (or the subject). Whether a symptom of a disease has been alleviated can be evaluated by any clinical testing methods commonly used by doctors or other health care professionals to evaluate the severity or progression of the symptom. Although the embodiments of the present disclosure (for example, treatment methods or products) may not be effective in alleviating all the target symptoms of the disease, they shall reduce the target symptoms of the disease in a statistically significant number of patients (or subjects), as determined according to any statistical testing methods known in the art, such as Student t-test, chi-square test, Mann and Whitney's U test, Kruskal-Wallis test (H test), Jonckheere-Terpstra test and Wilcoxon test.

"Amino acid conservative modification" or "amino acid conservative substitution" means that the amino acids in a protein or polypeptide are substituted by other amino acids having similar characteristics (such as charge, side chain size, hydrophobicity/hydrophilicity, backbone conformation and rigidity), such that the changes can frequently be performed without altering the biological activity or other required characteristics (such as affinity and/or specificity to an antigen) of the protein or polypeptide. Those skilled in the art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity.

"Bind to IL-4R" refers to the ability to interact with human IL-4R. The term "antigen-binding site" herein refers to a three-dimensional spatial site recognized by an antibody or an antigen-binding fragment described herein.

"Cross-react" refers to the ability of an antibody described herein to bind to IL-4R from a different species. For example, an antibody described herein that binds to human IL-4R may also bind to IL-4R of another species. Cross-reactivity is measured by detecting specific reactivity with purified antigen in binding assays (e.g., SPR and ELISA) or binding or functional interactions with cells physiologically expressing IL-4R. Methods for determining cross-reactivity include standard binding assays as described herein, for example, surface plasmon resonance (SPR) analysis or flow cytometry.

"Neutralizing" or "blocking" antibody refers to an antibody whose binding to hIL-4R results in inhibition of biological activity of hIL-4 and/or hIL-13. Such inhibition of biological activity of hIL-4 and/or IL-13 can be assessed by measuring one or more indexes of biological activity of hIL-4 and/or hIL-13 well known in the art, such as hIL-4 and/or hIL-13-induced cell activation and binding of hIL-4 to hIL-4R (see, e.g., CN103739711A). "Inhibition of growth" (e.g., involving cells) is intended to include any measurable reduction in cell growth.

The terms "inducing immune response" and "enhancing immune response" can be used interchangeably and refer to the stimulation (i.e., passive or adaptive) of an immune response to a particular antigen. The term "induce" specific for inducing CDC or ADCC refers to stimulating specific direct cell killing mechanism.

"Antibody-dependent cell-mediated cytotoxicity (ADCC)" means that the Fc receptor-expressing cells directly kill antibody-coated target cells by recognition of the Fc segment of the antibody. The ADCC effector function of the antibody may be reduced or eliminated by modification of the Fc segment of the IgG. The modification refers to a mutation in the heavy chain constant region of the antibody, such as a mutation selected from the group consisting of N297A, L234A and L235A of IgG1; IgG2/4 chimera, F235E of IgG4, and L234A/E235A mutation.

The engineered antibody or antigen-binding fragment can be prepared and purified using conventional methods. For example, cDNA sequences encoding the heavy and light chains can be cloned and recombined into a GS expression vector. Recombinant immunoglobulin expression vectors can be stably transfected into CHO cells. The sequence of the humanized antibody described herein was inserted into a corresponding expression vector by using a molecular cloning technique, and the corresponding humanized antibody could be obtained by using an HEK293 cell expression system for expression and production. As a more recommended prior art, mammalian expression systems may result in glycosylation of antibodies, particularly at the highly conserved N-terminus of the FC region. Stable clones are obtained by expression of antibodies specifically binding to the human-derived antigen. Positive clones are expanded in a serum-free medium of a bioreactor to produce antibodies. The culture with the secreted antibody can be purified and collected using conventional techniques. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

"Effective amount" or "effective dosage" refers to the amount of a drug, a compound or a pharmaceutical composition necessary to obtain any one or more beneficial or desired therapeutic results. For preventive use, the beneficial or desired results include elimination or reduction of risk, reduction of severity or delay of the onset of a disorder, including the biochemistry, histology and/or behavioral symptoms of the disorder, complications thereof and inter- mediate pathological phenotypes that appear during the progression of the disorder. For therapeutic applications, the beneficial or desired results include clinical results, such as reducing the incidence of various disorders related to the target antigen of the present disclosure or alleviating one or more symptoms of the disorder, reducing the dosage of other agents required to treat the disorder, enhancing the thera- peutic effect of another agent, and/or delaying the progres- sion of disorders of the patient (or the subject) related to the target antigen of the present disclosure.

"Exogenous" refers to substances produced outside organisms, cells or human bodies according to circum- stances.

"Endogenous" refers to substances produced inside cells, organisms or human bodies according to circumstances.

"Isolated" refers to a purified state, and in this case means that the designated molecule is substantially free of other biomolecules, such as nucleic acids, proteins, lipids, carbo- hydrates, or other materials (such as cell debris and growth medium). Generally, the term "isolated" does not mean the complete absence of such substances or the absence of water, buffers or salts, unless they are present in amounts that will significantly interfere with the experimental or therapeutic use of the compounds described herein.

"Homology" or "identity" refers to sequence similarity between two polynucleotide sequences or between two polypeptides. When positions in both compared sequences are occupied by the same base or amino acid monomer subunit, e.g., if each position of two DNA molecules is occupied by adenine, then the molecules are homologous at that position. The homology percentage between two sequences is a function of the number of matching or homologous positions shared by the two sequences divided by the number of positions compared×100%. For example, if 6 out of 10 positions are matched or homologous when two sequences are optimally aligned, the two sequences are 60% homologous. Generally, when two sequences are aligned, comparison is performed to obtain the maximum homology percentage. The "at least 85% sequence identity" described herein means that when the variant and the parent sequence are aligned, the two sequences are at least 85% homologous; in some embodiments, they are at least 86%, 87%, 88%, 89%, 90%, 91%, 92%, 93%, 94%, 95%, 96%, 97%, 98% or 99% homologous; in some specific embodi- ments, they are 90%, 95% or 99% or more homologous; in other specific embodiments, they are at least 95% homolo- gous. The amino acid sequence having at least 85% sequence identity is obtained by one or more amino acid deletion, insertion or substitution mutations made in the parent sequence.

As used herein, the expressions "cell", "cell line" and "cell culture" can be used interchangeably, and all such designations include their progenies. Therefore, the terms "transformant" and "transformed cell" include primary test cells and cultures derived therefrom, regardless of the num- ber of transfers. It should also be understood that all prog- enies may not be precisely identical in DNA content due to deliberate or unintentional mutations. Mutant progeny with the same function or biological activity as screened in the original transformed cells is included.

The term "optional" or "optionally" means that the event or circumstance subsequently described may, but not nec- essarily, occur, and that the description includes instances where the event or circumstance occurs or does not occur. For example, "optionally comprising 1-3 antibody heavy chain variable regions" means that the antibody heavy chain variable region of a particular sequence may, but not nec- essarily, be present.

Exemplary preparation process for the pharmaceutical composition (formulation) of antibody:

Step 1: a certain amount of purified anti-IL-4R antibody solution was subjected to solvent exchange (preferably ultrafiltration) with a buffer free of antibody; at least 6-fold of volume was exchanged by ultrafiltration membrane, and the antibody was concentrated to a certain concentration. A certain volume of mother liquor of other auxiliary materials was added, and the mixture was diluted with a buffer to allow the antibody and each auxiliary material to reach the required concentration and be well mixed. The stock solu- tion was filtered and then subjected to central-control sam- pling and tested for sterility. The stock solution passed through a 0.22 μm PVDF filter and the filtrate was collected.

Step 2: The filling amount was adjusted to 2.15 mL, the filtrate was filled into 2 mL vials, and stoppers were applied, and central-control samplings were performed at the begin- ning, in the middle and at the end of filling to detect the difference of filling volume.

Step 3: The capping machine was started to apply alumi- num caps and to perform capping.

Step 4: Visual inspection was performed to confirm that products have no defects, such as inaccurate filling. Vial labels were printed and attached; carton labels were printed, cartons were folded, packing was performed, and carton labels were attached.

EXAMPLES

The following examples further illustrate the present disclosure, but the present disclosure is not limited thereto. The experimental methods in the examples in which specific conditions are not specified are generally performed under conventional conditions such as Antibodies: A Laboratory Manual and Molecular Cloning: A Laboratory Manual by Cold Spring Harbor Laboratory, or under conditions recom- mended by the manufacturer of the raw material or the goods. Reagents without specific origins indicated are com- mercially available conventional reagents.

Examples of Antibody Preparation

Example 1: Mouse Immunization and Detection

The his-tagged human IL-4R (h-IL-4R-his) recombinant protein, the his-tagged mouse IL-4R (m-IL-4R-his) recom- binant protein and the his-tagged rhesus IL-4R (rhesus-IL- 4R-his) recombinant protein were synthesized by Acrobio- systems, expressed by HEK293 and purified.

The humanized Fc-tagged human IL-4R recombinant protein (h-IL-4R-Fc) was self-designed, expressed and purified. The purified proteins were used in the experiments described in the following examples.

CDR amino acid residues of the VL and VH regions of the antibodies or antigen-binding fragments in this example correspond with known Kabat numbering scheme (LCDR 1-3, HCDR 2-3) and AbM scheme (HCDR1) in terms of number and positions.

TABLE 1

| Immunogen information | | |
| --- | --- | --- |
| Name | Start and end of amino acid sequence | Database No./ Catalog No. |
| h-IL-4R-his | Met26-His232 | NP_000409.1 |
| m-IL-4R-his | Ile26-Arg233 | NP_001008700 |
| rhesus-IL-4R-his | Met26-Arg232 | G7Q0S7 |
| h-IL-4R-Fc | Met1-His232 | NP_000409.1 |

Anti-human IL-4R monoclonal antibodies were generated by immunizing mice. The mice were experimental C57BL/6 mice, female, 6-8 weeks old (Joinn Laboratories (Suzhou) New Drug Research Center Co., Ltd., animal production license number: 201503052).

Feeding environment: SPF grade. The purchased mice were fed in a laboratory environment for 1 week, in a 12/12 hour light/dark cycle, at a temperature of 20-25° C., with humidity at 40-60%. The mice that had adapted to the environment were divided into 3 cages with 5 mice in each cage. The immune antigen was Fc-tagged human IL-4R recombinant protein (h-IL4R-Fc at a concentration of 0.73 mg/mL). Freund's adjuvant (Sigma, Cat #: F5881) was used for emulsification, where Freund's complete adjuvant (CFA, Pierce, Cat #77140) was used for primary immunization, and nucleic acid adjuvant (CpG, Sangon Biotech (Shanghai)) and aluminum adjuvant (Alum, Thermo Cat #77161) for remaining boost immunizations.

On day 0, 70 µg of emulsified antigen was injected intraperitoneally (IP) in each mouse. On days 14, 28, 42, 56 and 77, dorsal and intraperitoneal injections of antigen (0.1 mL each) were performed based on dorsal lump and abdominal swelling. Blood was collected on days 21, 35, 49, 63 and 84 for blood tests, and mouse serum was tested by the ELISA method of Example 2 to determine the antibody titer in the mouse serum. After the fourth immunization, spleen cell fusion was performed in mice in which the antibody titer was high and tended to be stable in serum. Boost immunization was performed 3 days prior to fusion, and 10 µg of antigen solution formulated with phosphate buffer was injected intraperitoneally (IP) in each mouse. Spleen lymphocytes and myeloma cells, Sp2/0 cells (ATCC® CRL-8287™) were fused by following an optimized PEG-mediated fusion procedure to obtain hybridoma cells.

Example 2: ELISA Test and Screening of Antibodies

1. ELISA Binding Experiment:

ELISA experiment was used to detect binding properties of anti-IL-4R antibodies. A microplate was coated with his-tagged IL-4R recombinant protein. After the antibody was added to each well, the activity of the binding of the antibody to the antigen was detected by adding a secondary antibody (HRP-conjugated anti-primary antibody Fc antibody) and HRP substrate TMB.

Human or rhesus IL-4R-his protein was coated on a 96-well microplate, 100 µL per well at a concentration of 0.5 µg/mL, and incubated overnight at 4° C. The plate was washed three times with washing buffer at 250 µL per well. A blocking solution was added at 200 µL per well and the plate was incubated at room temperature for 2 h. The plate was washed three times with washing buffer at 250 µL per well. Anti-IL-4R antibody to be tested diluted in diluent was added at 100 µL per well. The plate was incubated at room temperature for 1 h. The plate was washed three times with washing buffer at 250 µL per well. HRP-labeled goat anti-human IgG secondary antibody diluted at 1:20000 with diluent was added at 100 µL per well. The plate was incubated at room temperature for 1 h. The plate was washed three times with washing buffer at 250 µL per well. TMB was added at 100 µL per well, and the mixture was reacted for 15 min in the dark. 0.16 M/L sulfuric acid was added at 50 µL per well. The OD value was read at 450 nm by a Thermo MultiSkanFc microplate reader and the binding $EC_{50}$ value of the anti-IL-4R antibody to IL-4R was calculated.

2. ELISA Blocking Experiment:

In this experiment, by in vitro blocking experiment, the blocking of the binding of human IL-4R to human IL-4 by the selected anti-human IL-4R antibodies was detected. Specifically, the Fc-tagged IL-4R recombinant protein was coated on a 96-well microplate, the antibody that bound to human IL-4R was then added to fully bind to and occupy epitope, and then IL-4 (Biolegend, Cat #574004) was added. Biotin-conjugated anti-IL-4 antibody and Neutravidin-HRP (Pierce, Cat #31001) were used to detect whether IL-4 could still bind to IL-4R, and $IC_{50}$ value of the blocking of the IL-4/IL-4R binding by the IL-4R antibody was calculated.

Human IL-4R-Fc protein was coated on a 96-well microplate, 100 µL per well at a concentration of 0.5 µg/mL, and incubated overnight at 4° C. The plate was washed three times with washing buffer at 250 µL per well. A blocking solution was added at 200 µL per well and the plate was incubated at room temperature for 2 h. The plate was washed three times with washing buffer at 250 µL per well. Anti-IL-4R antibody to be tested diluted in diluent was added at 100 µL per well, and the plate was incubated at room temperature for 1 h. The plate was washed three times with washing buffer at 250 µL per well. Diluted IL-4 was added at 100 µL per well, and the plate was incubated at room temperature for 1 h and then washed three times. Diluted biotin-conjugated anti-IL-4 antibody was added at 100 µL per well, and the plate was incubated at room temperature for 1 h and then washed three times. HRP-labeled Neutravidin diluted in a diluent at 1:5000 was added, and the plate was incubated at room temperature for 1 h. The plate was washed three times with washing buffer at 250 µL per well. TMB was added at 100 µL per well, and the mixture was reacted for 15 min in the dark. 0.16 M/L sulfuric acid was added at 50 µL per well. The OD value was read at 450 nm by a Thermo MultiSkanFc microplate reader and the $IC_{50}$ value of the blocking of the binding of IL-4R to IL-4 by the IL-4R antibody was calculated.

Example 3: Reporter Gene Cell Activity Experiment of Antibodies Binding to Human IL-4R HEK-Blue IL-4 cells were purchased from Invivogen (Cat #hkb-stat6), and the cells were stably transfected with the human IL-4R gene and STAT6-mediated SEAP genome. Therefore, the activation level of the IL-4R signaling pathway could be characterized by detecting the secreted SEAP in the supernatant by QUANTI-Blue, the substrate of SEAP.

In this experiment, the in vitro cell activity of the IL-4R antibody was evaluated according to $IC_{50}$ by detecting the activation of HEK-Blue IL-4 cells.

HEK-Blue IL-4 cells were cultured in DMEM medium containing 10% FBS, 100 μg/mL Zeocin (Invivogen, Cat #ant-zn-05) and 10 μg/mL Blasticidin (Invivogen, Cat #ant-bl-05), and passaged 2-3 times a week in a passage ratio of 1:5 or 1:10. During passaging, the medium was removed by pipetting, and the cell layer was rinsed with 5 mL of 0.25% trypsin. Then the trypsin was removed by pipetting, the cells were digested in an incubator for 3-5 min, and then a fresh medium was added to resuspend cells. 100 μL of cell suspension was added to a 96-well cell culture plate at a density of $5 \times 10^5$ cells/mL, and the medium was DMEM containing 10% FBS, 100 μg/mL Zeocin and 30 μg/mL Blasticidin. Only 100 μL of sterile water was added to the periphery of the 96-well plate. The plate was incubated in an incubator for 24 h (37° C., 5% $CO_2$). After the cells adhered to the wall, the serially diluted antibody to be tested was added at 100 μL per well. The plate was incubated in an incubator for 20-24 h (37° C., 5% $CO_2$). Then 20 μL of cell supernatant was taken from each well into a new 96-well flat bottom plate, 180 μL of QUANTI-Blue substrate solution was added, and the plate was incubated in an incubator for 1-3 h in the dark. The absorbance at 620 nm was measured with a microplate reader (Thermo MultiSkanFc).

Example 4: Inhibition of Proliferation of TF-1 Cells by Antibodies Binding to Human IL-4R TF-1 cells (ATCC CRL-2003) are lymphoma cells which express IL-4R and are sensitive to cytokines such as IL-4/IL-13. IL-4 can stimulate TF-1 cells to proliferate in the absence of GM-CSF. In this experiment, neutralizing activities of different anti-IL-4R antibodies were compared by adding neutralizing antibodies to block the action pathway of IL-4 and inhibit proliferation of TF-1 cells.

TF-1 cells were cultured in RPMI1640 medium containing 10% FBS and 2 ng/mL GM-CSF (R&D, Cat #215-GM- After the culturing was completed, cell proliferation was detected by using a CTG kit (Promega, Cat #G7572).

Example 5: In Vitro Binding Affinity and Kinetics Experiment

The affinity of the humanized antibody against IL-4R to be tested for human IL-4R was determined using Biacore, GE instrument.

Human antibody capture antibody was covalently coupled to a biosensor chip CM5 of Biacore instrument (Biacore X100, GE) according to the method described in the instruction of human antibody capture kit (Cat #BR-1008-39, GE), and thus a certain amount of antibodies to be tested were captured based on affinity. Then a series of concentration gradients of IL-4R antigens (the IL-4R antigens all purchased from Acrobiosystems, Cat #ILR-H5221) flowed through the surface of chip, and the Biacore instrument (Biacore X100, GE) was used to detect the reaction signals in real time to obtain the binding and dissociation curves. After each cycle of dissociation was completed, the biochip was washed and regenerated with a regeneration solution prepared in the human antibody capture kit. The amino coupling kit used in the experiment was purchased from GE corporation (Cat #BR-1000-50, GE), and the buffer was HBS-EP+ 10× buffer solution (Cat #BR-1006-69, GE) diluted to 1× (pH 7.4) with D.I. Water.

The data obtained from the experiment were fitted with BiacoreX100 evaluation software 2.0 GE software with a (1:1) binding model to obtain affinity values.

Example 6: Sequences and Preparation of Antibodies

Based on the ELISA binding experiment (ELISA binding of human IL-4R-his) and ELISA blocking experiment (ELISA blocking of human IL-4/IL-4R) as described above in Example 2, the experiment of inhibiting activation of HEK293-Blue IL-4 cells under IL-4 stimulation in Example 3 and the experiment of inhibiting proliferation of TF-1 cells under IL-4 stimulation in Example 4, two monoclonal hybridoma cell strains showing the best in vitro activity were selected. The results of activity test are shown in Table 2.

TABLE 2

| Results of activity test of hybridoma cell strains | | | | | | |
|---|---|---|---|---|---|---|
| | | ELISA (EC$_{50}$) (ng/mL) | | | ELISA IC$_{50}$ for blocking binding of human | IC$_{50}$ for blocking binding of HEK293-Blue | IC$_{50}$ for inhibiting IL-4-related proliferation |
| Hybridoma | Human IL-4R-his | Monkey IL-4R-his | Murine IL-4R-his | IL-4/IL-4R (ng/mL) | IL-4 cells (to IL-4) (ng/mL) | of TF-1 cells (ng/mL) |
| 25G7 | 3.319 | No binding | No binding | 8.132 | 0.9749 | 51.26 |
| 7B10 | 45.78 | No binding | No binding | 29.86 | 79.76 | 418.1 |
| Dupilumab | 27.62 | No binding | No binding | 52.08 | 5.069 | 102.2 |

010), and passaged 2-3 times a week in a passage ratio of 1:10. 100 μL of cell suspension was added to a 96-well cell culture plate at a density of $2 \times 10^5$ cells/mL, and the medium was RPMI1640 medium containing 10% FBS. Only 100 μL of sterile water was added to the periphery of the 96-well plate. 50 μL of serially diluted antibody to be tested and 50 μL of IL-4 (R&D, Cat #204-IL-050) at a final concentration of 0.7 ng/mL were added to each well, and the culture plate was incubated in an incubator for 72 h (37° C., 5% $CO_2$).

Monoclonal hybridoma cell strains 25G7 and 7B10 were selected, and the antibody sequences were cloned therefrom. The cloning of a sequence from hybridoma is as follows.

Hybridoma cells at logarithmic growth phase were collected, and the RNA was extracted using Trizol (Invitrogen, 15596-018) (following the procedures in the kit instructions) and reverse transcribed (PrimeScript™ Reverse Transcriptase, Takara, cat #2680A). The cDNA obtained by reverse transcription was amplified by PCR using mouse Ig-Primer Set (Novagen, TB326 Rev.B 0503) and then sent for sequencing by a sequencing company, and the resulting antibody sequences were analyzed.

The heavy chain and light chain variable region sequences of murine monoclonal antibody 25G7 are as follows:

```
25 G7 HCVR
                                        (SEQ ID NO: 1)
EVQLVESGGGLVKPGGSLKLSCAASGFTFSDYGMHWVRQAPEKGLEWVAF

ISSGSSIIYYADIVKGRSTISRDNAKNTLFLQMTSLRSEDTAMYYCTRGN

KRGFFDYWGQGTILTVSS

25 G7 LCVR
                                        (SEQ ID NO: 2)
QIVLTQSPALMSASPGEKVTMTCNASSSVSYMYWYQRKPRSSPKPWIYLT

SNLASGVPVRFSGSGSGTSYSLTISSMEAEDAATYYCQQWRSNPPMLTFG

SGTKLEVK
```

The CDR sequences contained in this antibody are shown in Table 3.

TABLE 3

| CDR sequences of monoclonal antibody 25G7 | | |
|---|---|---|
| Name | Sequence | No. |
| HCDR1 | GFTFSDYGMH | SEQ ID NO: 3 |
| HCDR2 | FISSGSSIIYYADIVKG | SEQ ID NO: 4 |
| HCDR3 | GNKRGFFDY | SEQ ID NO: 5 |
| LCDR1 | NASSSVSYMY | SEQ ID NO: 6 |
| LCDR2 | LTSNLAS | SEQ ID NO: 7 |
| LCDR3 | QQWRSNPPMLT | SEQ ID NO: 8 |

The heavy chain and light chain variable region sequences of murine monoclonal antibody 7B10 are as follows:

```
7B10 HCVR
                                        (SEQ ID NO: 9)
QVQLQQPGTELLKPGASVSLSCKASGYTFTSYWMHWVKQRPGQGLEWIGL
```

```
-continued
IHPNSDTTKFSENFKTRATLTIDKSSSTAYMKLSSLTSEDSAVYYCAKSK

IITTIVARHWYFDVWGTGTTVTVSS

7B10 LCVR
                                       (SEQ ID NO: 10)
DIVLTQSPPSLAVSLGQRATISCKASQSVDYGGDSYMNWYQQKLGQPPKV

LIYAASNLESGIPARFSGSGSGTDFTLNIHPVEEEDVATYYCQHSNENPP

TFGGGTKLEIK
```

The CDR sequences contained in this antibody are shown in Table 4.

TABLE 4

| CDR sequences of monoclonal antibody 7B10 | | |
|---|---|---|
| Name | Sequence | No. |
| HCDR1 | GYTFTSYWMH | SEQ ID NO: 11 |
| HCDR2 | LIHPNSDTTKFSENFKT | SEQ ID NO: 12 |
| HCDR3 | SKIITTIVARHWYFDV | SEQ ID NO: 13 |
| LCDR1 | KASQSVDYGGDSYMN | SEQ ID NO: 14 |
| LCDR2 | AASNLES | SEQ ID NO: 15 |
| LCDR3 | QHSNENPPT | SEQ ID NO: 16 |

The obtained variable region sequences were linked to the human constant region sequence to obtain a human-murine chimeric antibody sequence. The sequence of the chimeric antibody was inserted into a corresponding expression vector using molecular cloning techniques. Human-murine chimeric antibodies 25G7-C and 7B10-C were obtained using HEK293 cell expression system.

The purified chimeric antibodies were tested for their activity in vitro by the methods described in Examples 2-5 above, and the data are shown in Table 5. The results show that the 25G7-C antibody is significantly better than the reference antibody dupilumab (synthesized with reference to WHO Drug Information, Vol. 26, No. 4, 2012) both in blocking the IL-4 binding and in inhibiting cell proliferation.

TABLE 5

| | In vitro activity assay | | | | | |
|---|---|---|---|---|---|---|
| Antibodies | Human IL-4R-his ELISA binding (EC$_{50}$) (ng/mL) | Monkey IL-4R-his ELISA binding (EC$_{50}$) (ng/mL) | Human IL-4/IL-4R ELISA blocking (IC$_{50}$) (ng/mL) | Blocking binding of HEK293-Blue IL-4 cells (to IL-4) (IC$_{50}$) (ng/mL) | Inhibiting IL-4-related proliferation of TF-1 cells (IC$_{50}$) (ng/mL) | K$_D$ (nM) (Biacore) |
| 25G7-C | 9.094 | No binding | 39.69 | 2.025 | 20.27 | 0.725 |
| 7B10-C | 11.83 | No binding | 162.3 | 9.034 | 46.43 | 0.278 |
| Dupilumab | 55.84 | No binding | 209.4 | 3.235 | 207.2 | 0.126 |

Example 7: Mouse Antibody Humanization Experiment

The resulting murine antibodies 25G7 and 7B10 were humanized. On the basis of the typical structure of the murine antibody VH/VLCDR obtained, the heavy chain and light chain variable region sequences were compared with a human antibody Germine database to obtain a human germline template with high homology. The human germline light chain framework region was derived from human κ light chain genes, preferably human germline light chain templates IGKV3-11*01 (SEQ ID NO: 22, for antibody 25G7) and IGKV2D-29*01 (SEQ ID NO: 24, for antibody 7B10). The human germline heavy chain framework region was derived from human heavy chain, preferably human germline heavy chain templates IGHV3-48*01 (SEQ ID NO: 21, for antibody 25G7) and IGHV1-2*02 (SEQ ID NO: 23, for antibody 7B10).

Sequences of human germline templates are shown below.

```
Human germline heavy chain template
IGHV3-48*01:
                                  (SEQ ID NO: 21)
EVQLVESGGGLVQPGGSLRLSCAASGFTFSSYSMNWVRQAPGKGLEWVSY

ISSSSSTIYYADSVKGRFTISRDNAKNSLYLQMNSLRAEDTAVYYCAR

Human germline light chain template
IGKV3-11 *01:
                                  (SEQ ID NO: 22)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWP

Human germline heavy chain template
IGHV1-2*02:
                                  (SEQ ID NO: 23)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCAR

Human germline light chain template
IGKV2D-29*01:
                                  (SEQ ID NO: 24)
DIVMTQTPLSLSVTPGQPASISCKSSQSLLHSDGKTYLYWYLQKPGQPPQ

LLIYEVSNRFSGVPDRFSGSGSGTDFTLKISRVEAEDVGVYYCMQSIQLP
```

The CDR regions of the murine antibody were grafted onto a selected humanized template and then recombined with IgG constant regions, and then back mutation was performed to obtain a series of humanized molecules.

hu7B10-VH-a, hu7B10-VH-b and hu7B10-VH-c were modified for druggability, and the first position of the heavy chain human germline template was changed from Q to E. The sequences of the humanized heavy chain variable regions of the two antibodies are set forth in SEQ ID NOs: 25-27 and SEQ ID NOs: 31-33, respectively; the sequences of the light chain variable regions are set forth in SEQ ID NOs: 28-30 and SEQ ID NOs: 34-36, respectively.

```
hu25G7-VH-a:
                                  (SEQ ID NO: 25)
EVQLVESGGGLVQPGGSLRLSCAASGFTFSDYGMHWVRQAPGKGLEWVAF

ISSGSSIIYYADIVKGRFTISRDNAKNSLYLQMNSLRAEDTAVYYCARGN

KRGFFDYWGQGTLVTVSS
```

```
hu25G7-VH-b:
                                  (SEQ ID NO: 26)
EVQLVESGGGLVQPGGSLRLSCAASGFTFSDYGMHWVRQAPGKGLEWVAF

ISSGSSIIYYADIVKGRFTISRDNAKNSLYLQMNSLRAEDTAVYYCTRGN

KRGFFDYWGQGTLVTVSS hu25G7-VH-c:
                                  (SEQ ID NO: 27)
EVQLVESGGGLVQPGGSLRLSCAASGFTFSDYGMHWVRQAPGKGLEWVAF

ISSGSSIIYYADIVKGRSTISRDNAKNSLYLQMNSLRAEDTAVYYCTRGN

KRGFFDYWGQGTLVTVSS hu25G7-VL-a:
                                  (SEQ ID NO: 28)
EIVLTQSPATLSLSPGERATLSCNASSSVSYMYWYQQKPGQAPRLLIYLT

SNLASGIPARFSGSGSGTDFTLTISSLEPEDFAVYYCQQWRSNPPMLTFG

GGTKVEIK hu25G7-VL-b:
                                  (SEQ ID NO: 29)
EIVLTQSPATLSLSPGERATLSCNASSSVSYMYWYQQKPGQAPRLLIYLT

SNLASGIPARFSGSGSGTDYTLTISSLEPEDFAVYYCQQWRSNPPMLTFG

GGTKVEIK hu25G7-VL-c:
                                  (SEQ ID NO: 30)
EIVLTQSPATLSLSPGERATLSCNASSSVSYMYWYQQKPGQAPRPWIYLT

SNLASGIPARFSGSGSGTDYTLTISSLEPEDFAVYYCQQWRSNPPMLTFG

GGTKVEIK hu7B10-VH-a:
                                  (SEQ ID NO: 31)
EVQLVQSGAEVKKPGASVKVSCKASGYTFTSYWMHWVRQAPGQGLEWMGL

IHPNSDTTKFSENFKTRVTMTRDTSISTAYMELSRLRSDDTAVYYCARSK

IITTIVARHWYFDVWGQGTTVTVSS hu7B10-VH-b:
                                  (SEQ ID NO: 32)
EVQLVQSGAEVKKPGASVKVSCKASGYTFTSYWMHWVRQAPGQGLEWMGL

IHPNSDTTKFSENFKTRVTMTIDTSISTAYMELSRLRSDDTAVYYCAKSK

IITTIVARHWYFDVWGQGTTVTVSS hu7B10-VH-c:
                                  (SEQ ID NO: 33)
EVQLVQSGAEVKKPGASVKVSCKASGYTFTSYWMHWVRQAPGQGLEWMGL

IHPNSDTTKFSENFKTRVTLTIDKSISTAYMELSRLRSDDTAVYYCAKSK

IITTIVARHWYFDVWGQGTTVTVSS hu7B10-VL-a:
                                  (SEQ ID NO: 34)
DIVMTQTPLSLSVTPGQPASISCKASQSVDYGGDSYMNWYLQKPGQPPQL

LIYAASNLESGVPDRFSGSGSGTDFTLKISRVEAEDVGVYYCQHSNENPP

TFGGGTKVEIK hu7B10-VL-b:
                                  (SEQ ID NO: 35)
DIVLTQTPLSLSVTPGQPASISCKASQSVDYGGDSYMNWYLQKPGQPPQL

LIYAASNLESGVPDRFSGSGSGTDFTLKISRVEAEDVGVYYCQHSNENPP

TFGGGTKVEIK
```

-continued hu7B10-VL-c:

(SEQ ID NO: 36)

DIVMTQTPLSLSVTPGQPASISCKASQSVDYGGDSYMNWYLQKPGQPPQL

LIYAASNLESGIPDRFSGSGSGTDFTLKISRVEAEDVGVYYCQHSNENPP

TFGGGTKVEIK

The back mutation design of hybridoma clone 25G7 is shown in Table 6.

TABLE 6

| Template selection and back mutation design | | | |
|---|---|---|---|
| 25G7-VL | | 25G7-VH | |
| hu25G7-VL-a | Grafted | hu25G7-VH-a | S49A |
| hu25G7-VL-b | F71Y | hu25G7-VH-b | S49A, A93T |
| hu25G7-VL-c | L46P, L47W, F71Y | hu25G7-VH-c | S49A, F67S, A93T |

Note:
amino acid positions for back mutation were determined using Kabat numbering scheme.

The back mutation design of hybridoma clone 7B10 is shown in Table 7 below.

TABLE 7

| Template selection and back mutation design | | | |
|---|---|---|---|
| 7B10-VL | | 7B10-VH | |
| hu7B10-VL-a | Grafted | hu7B10-VH-a | Grafted |
| hu7B10-VL-b | M4L | hu7B10-VH-b | R71I, R94K |
| hu7B10-VL-c | V58I | hu7B10-VH-c | M69L, R71I, T73K, R94K |

Note:
amino acid positions for back mutation were determined using Kabat numbering scheme.

The respective complete light chain and heavy chain sequences of exemplary humanized antibody hu25G7 (using VH-c heavy chain and VL-a light chain) and hu7B10 antibody molecule (using VH-b heavy chain and VL-b light chain) are set forth in SEQ ID NOs: 17-20.

hu25G7 HC (SEQ ID NO: 17)

EVQLVESGGGLVQPGGSLRLSCAASGFTFSDYGMHWVRQAPGKGLEWVAF

ISSGSSIIYYADIVKGRSTISRDNAKNSLYLQMNSLRAEDTAVYYCTRGN

KRGFFDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK hu25G7 LC (SEQ ID NO: 18)

EIVLTQSPATLSLSPGERATLSCNASSSVSYMYWYQQKPGQAPRLLIYLT

SNLASGIPARFSGSGSGTDFTLTISSLEPEDFAVYYCQQWRSNPPMLTFG

GGTKVEIKRTVAAPSVFIFPPSDEQLKSGTASVVCLLNNFYPREAKVQWK

-continued

VDNALQSGNSQESVTEQDSKDSTYSLSSTLTLSKADYEKHKVYACEVTHQ

GLSSPVTKSFNRGEC hu7B10 HC (SEQ ID NO: 19)

EVQLVQSGAEVKKPGASVKVSCKASGYTFTSYWMHWVRQAPGQGLEWMGL

IHPNSDTTKFSENFKTRVTMTIDTSISTAYMELSRLRSDDTAVYYCAKSK

IITTIVARHWYFDVWGQGTTVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSLS

LSPGK hu7B10 LC (SEQ ID NO: 20)

DIVLTQTPLSLSVTPGQPASISCKASQSVDYGGDSYMNWYLQKPGQPPQL

LIYAASNLESGVPDRFSGSGSGTDFTLKISRVEAEDVGVYYCQHSNENPP

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The sequence of the humanized antibody was inserted into a corresponding expression vector by using a molecular cloning technique, and the corresponding humanized antibody could be obtained by using an HEK293 cell expression system for expression and production.

Example 8: Activity Data of Humanized Antibodies

Humanized antibodies hu25G7 and hu7B10 were subjected to the in vitro activity assays described in Examples 2-5, and the results are shown in Table 8.

The results showed that both hu25G7 and hu7B10 bound only to human IL-4R and not to rhesus IL-4R, indicating that both antibodies bound to a human epitope that was not homologous to rhesus and specifically bound to human IL-4R. Both antibodies were able to block IL-4/IL-4R binding and intracellular signaling pathways, resulting in neutralization of IL-4 activation and inhibition of proliferation of TF-1 cells, where the blocking and inhibitory activity of hu25G7 is still significantly better than those of the reference antibody dupilumab.

TABLE 8

| | | | Blocking binding of HEK293-Blue IL-4 cells (to IL-4) (IC$_{50}$) (ng/mL) | | | |
|---|---|---|---|---|---|---|
| Antibodies | Human IL-4R-his ELISA binding (EC$_{50}$) (ng/mL) | Monkey IL-4R-his ELISA binding (EC$_{50}$) (ng/mL) | Human IL-4/IL-4R ELISA blocking (IC$_{50}$) (ng/mL) | | Inhibiting IL-4-related proliferation of TF-1 cells (IC$_{50}$) (ng/mL) | K$_D$ (nM) (Biacore) |

In vitro activity assay

| Antibodies | Human IL-4R-his ELISA binding (EC$_{50}$) (ng/mL) | Monkey IL-4R-his ELISA binding (EC$_{50}$) (ng/mL) | Human IL-4/IL-4R ELISA blocking (IC$_{50}$) (ng/mL) | Blocking binding of HEK293-Blue IL-4 cells (to IL-4) (IC$_{50}$) (ng/mL) | Inhibiting IL-4-related proliferation of TF-1 cells (IC$_{50}$) (ng/mL) | K$_D$ (nM) (Biacore) |
|---|---|---|---|---|---|---|
| hu25G7 | 3.413 | No binding | 23.6 | 0.9431 | 29.56 | 1.07 |
| hu7B10 | 12.010 | No binding | 75.3 | 6.8700 | 112.4 | 0.284 |
| Dupilumab | 42.560 | No binding | 178.7 | 0.6668 | 491.2 | 0.126 |

Example 9: Affinity Maturation Assay for Humanized Antibody hu25G7

The hu25G7 antibody was subjected to affinity maturation through yeast display platform technology, an affinity maturation yeast library targeting 6 CDRs was designed and prepared based on the hu25G7 antibody, degenerate primers were designed, and the designed mutant amino acids were introduced into the hu25G7-scFv antibody library by PCR and homologous recombination. The size of each library was about 10$^9$, and the constructed yeast library was verified for its diversity by second-generation sequencing (GENEWIZ) method.

Biotin-labeled human IL-4R was used to select high-affinity antibodies from the hu25G7-scFv yeast library. After two rounds of MACS screening (streptomycin magnetic beads, Invitrogen) and two rounds of FACS screening (BD FACSAria™ FUSION), yeast single clone was selected for cultivation and expression induction. FACS (BD FACSCanto II) was used to detect the binding of the yeast single clone to human IL-4R, and yeast single clone with higher affinity than that of wild-type 25G7 antibody was selected for sequencing verification. After alignment and analysis of sequencing clones, the redundant sequence was removed, and the non-redundant sequence was converted into a full-length human antibody molecule for expression in mammalian cells. Affinity determination of the full-length antibody after affinity purification was carried out by using BIAcore X-100 (GE Life Sciences), and candidate antibody molecules with higher affinity for human IL-4R were selected. The affinity of the antibody molecules for human IL-4R was higher than that of the wild-type hu25G7 antibody, where the affinity of the hu25G7-A antibody molecule was equivalent to that of the dupilumab, and the affinity of the hu25G7-B molecule was significantly better than that of the dupilumab.

The light chain variable region sequence of the antibody hu25G7-A resulting from affinity maturation is as follows:

```
hu25G7-A LCVR
                            (SEQ ID NO: 37)
EIVLTQSPATLSLSPGERATLSCRASSSVPYMYWYQQKPGQAPRLLIYLT

SNLASGIPARFSGSGSGTDFTLTISSLEPEDFAVYYCQQWRAYPPMLTFG

GGTKVEIK
```

The CDR sequences contained in this antibody are shown in Table 9.

TABLE 9

LCDR sequences of hu25G7-A

| Name | Sequence | No. |
|---|---|---|
| LCDR1 | RASSSVPYMY | SEQ ID NO: 38 |
| LCDR2 | LTSNLAS | SEQ ID NO: 7 |
| LCDR3 | QQWRAYPPMLT | SEQ ID NO: 40 |

The light chain variable region sequence of antibody hu25G7-B is as follows:

```
hu25G7-B LCVR
                            (SEQ ID NO 41)
EIVLTQSPATLSLSPGERATLSCRASPGVPPLAWYQQKPGQAPRLLIYLA

SSRPSGIPARFSGSGSGTDFTLTISSLEPEDFAVYYCQQWRSNPPMLTFG

GGTKVEIK
```

The CDR sequences contained in this antibody are shown in Table 10.

TABLE 10

CDR sequences

| Name | Sequence | No. |
|---|---|---|
| LCDR1 | RASPGVPPLA | SEQ ID NO: 42 |
| LCDR2 | LASSRPS | SEQ ID NO: 39 |
| LCDR3 | QQWRSNPPMLT | SEQ ID NO: 8 |

The light chain variable region hu25G7-A LCVR described above was recombined with the hu25G7 light chain constant region to obtain the hu25G7-A antibody light chain; the light chain variable region hu25G7-B LCVR described above was recombined with the hu25G7 light chain constant region to obtain the hu25G7-B antibody light chain.

Amino acid residues of hu25G7-VH-c were optimized to obtain the heavy chain variable regions hu25G7-A/B VH and hu25G7-C VH.

```
hu25G7-A/B VH:
                            (SEQ ID NO: 43)
EVQLVESGGGLVQPGGSLRLSCAASGFTFSDYGMHWVRQAPGKGLEWVAF

ISSGSSIIYYADIVKGRSTISRDNAKNTLYLQMNSLRAEDTAVYYCTRGN

KRGFFDYWGQGTLVTVSS
```

-continued hu25G7-C VH:

(SEQ ID NO: 47)

EVQLVESGGGLVQPGGSLRLSCAASGFTFSDYGMHWVRQAPGKGLEWVAF

ISSGSSIIYYADIVKGRSTISRDNAKNTLYLQMSSLRAEDTAVYYCTRGN

KRGFFDYWGQGTLVTVSS

The heavy chain variable regions described above could be recombined with the hu25G7 heavy chain constant region to obtain hu25G7-A/hu25G7-B and hu25G7-C antibody heavy chains.

The complete heavy chain sequences of hu25G7-A and hu25G7-B are set forth in SEQ ID NO: 44.

hu25G7 HC (i.e., hu25G7-A/hu25G7-B antibody heavy chain)

(SEQ ID NO: 44)

EVQLVESGGGLVQPGGSLRLSCAASGFTFSDYGMHWVRQAPGKGLEWVAF

ISSGSSIIYYADIVKGRSTISRDNAKNTLYLQMNSLRAEDTAVYYCTRGN

KRGFFDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK hu25G7-C antibody heavy chain:

(SEQ ID NO: 48)

EVQLVESGGGLVQPGGSLRLSCAASGFTFSDYGMHWVRQAPGKGLEWVAF

ISSGSSIIYYADIVKGRSTISRDNAKNTLYLQMSSLRAEDTAVYYCTRGN hu25G7-A LC (SEQ ID NO: 45)

EIVLTQSPATLSLSPGERATLSCRASSSVPYMYWYQQKPGQAPRLLIYLT

SNLASGIPARFSGSGSGTDFTLTISSLEPEDFAVYYCQQWRAYPPMLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC hu25G7-B/hu25G7-C LC (SEQ ID NO: 46)

EIVLTQSPATLSLSPGERATLSCRASPGVPPLAWYQQKPGQAPRLLIYLA

SSRPSGIPARFSGSGSGTDFTLTISSLEPEDFAVYYCQQWRSNPPMLTFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Example 10: Affinity Maturation Activity Data of Humanized Antibodies

The antibodies hu25G7-A and hu25G7-B were detected according to Example 3 and Example 4; both antibodies hu25G7-A and hu25G7-B were able to block IL-4/IL-4R binding and intracellular signaling pathways, resulting in the neutralization of IL-4 and IL-13 activation and inhibition of proliferation of TF-1 cells. The activity data are shown in Table 11.

TABLE 11

| | Comparison of activity data | | | | |
|---|---|---|---|---|---|
| Antibodies | Human IL-4/IL-4R ELISA blocking (IC$_{50}$) (ng/mL) | Blocking binding of HEK293-Blue cells (to IL-4) (IC$_{50}$) (ng/mL) | Blocking binding of HEK293-Blue cells (to IL-13) (IC$_{50}$) (ng/mL) | Inhibiting IL-4-related proliferation of TF-1 cells (IC$_{50}$) (ng/mL) | Inhibiting IL-13-related proliferation of TF-1 cells (IC$_{50}$) (ng/mL) |
| hu25G7-A | 144.2 | 6.49 | 10.02 | 83.72 | 13.24 |
| hu25G7-B | 108.4 | 6.598 | 8.38 | 50.95 | 13.71 |
| Dupilumab | 156.3 | 12.48 | 14.75 | 100.9 | 18.10 |

-continued

KRGFFDYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

The respective complete light chain sequences are set forth in SEQ ID NOs: 45-46.

In the experiment of inhibiting proliferation of TF-1 cells caused by IL-13 stimulation, hu25G7-A and hu25G7-B both exhibited beneficial effects. Compared with dupilumab, hu25G7-A and hu25G7-B have a significantly improved effect in blocking the binding of IL-4 and IL-13 to IL-4R and cell proliferation caused by the binding.

Example 11: Study on Effect of Humanized Antibody on Mouse Dermatitis

Establishment of mouse dermatitis models: IL-4/IL-4Ra transgenic mice (purchased from Cyagen Bioscience Biological Research Center (Taicang) Co., Ltd.) were used, 100 µL of 1.5% OXZ acetone olive oil solution (acetone:olive oil=4:1) was evenly applied to the abdomen (an area of 3 cm×3 cm) of each mouse for sensitization, and the day of sensitization was D0 (day 0). On day 7, 20 μL of 1% OXZ acetone olive oil solution was evenly applied to both ears (both sides) of each mouse for challenging, and the challenging was performed every 72 h.

In the experiment, 5 groups were set up, namely a normal control group (only acetone olive oil solution was applied for sensitization and excitation), a model control group, an hu25G7-A group, an hu25G7-B group and a dupilumab group, with 3-5 mice in each group. The administration dose of the administration groups was 50 mg/kg, the route of administration was subcutaneous administration, and the administration was performed twice a week (see Table 12 for specific information). The ear thickness was measured with a vernier caliper on day 27, and the results are shown in FIG. 1.

TABLE 12

Administration regimen for each group

| Groups | Number of animals | Route of admin-istration | Dosage of admin-istration | Frequency of admin-istration |
|---|---|---|---|---|
| Normal control group | 3 (Male) | S.C. | — | Twice a week |
| Model control group | 5 (3 female + 2 male) | S.C. | — | Twice a week |
| hu25G7-A | 5 (3 female + 2 male) | S.C. | 50 mg/kg | Twice a week |
| hu25G7-B | 3 (2 female + 1 male) | S.C. | 50 mg/kg | Twice a week |
| Dupilumab | 4 (2 female + 2 male) | S.C. | 50 mg/kg | Twice a week |

The result showed that the ears of the mice in the model control group had obvious pathological damage, and the thickness of the ears was significantly greater than that in the normal control group. The ear thickness of mice in the hu25G7-A, hu25G7-B and dupilumab groups was significantly smaller than that in the model control group at day 27. That is, hu25G7-A, hu25G7-B and dupilumab can be used for treating dermatitis, and hu25G7-B has better effect than dupilumab.

Examples of Formulation Preparation

The equipment used in the preparation and the methods for calculating results are as follows:

SEC Molecular Exclusion Chromatography:

This is a method for analyzing the separation of a solute by the relative relationship between the pore size of the gel pores and the size of the polymer sample molecule coil.

SEC monomer content percentage=A monomer/A total×100% (A monomer is the peak area of the main peak monomer in the sample, and A total is the sum of all peak areas).

Instrument for SEC measurement: Agilent 1260; column: waters, XBrige BEH200 Å SEC (300×7.8 mm 3.5 μm).

CE Capillary Gel Electrophoresis:

This is a method of moving the gel into a capillary as a supporting medium for electrophoresis and separating according to the molecular weight of the sample under a certain voltage.

Non-reduced CE purity percentage=A main peak/A total×100% (A main peak is the peak area of the main peak in the sample, and A total is the sum of all peak areas). Instrument for CE measurement: Beckman model plus 800 iCIEF Imaged Capillary Isoelectric Focusing Electrophoresis:

This is a technique for separating according to the difference of isoelectric points pI of proteins.

iCIEF neutral peak content percentage=neutral peak area/total area×100% (total area is the sum of area of acidic, neutral and basic peaks).

Manufacturer of instrument for the iCIEF determination: simple protein, model: muarice.

Viscosity measurement: the viscosity is measured using a rheometer (manufacturer: Anton Paar, model: MCR xx2) at a measurement temperature of 25° C., and the samples are directly placed on the measurement plate for test.

Osmotic pressure: the freezing point method is used for measuring the osmotic pressure. The freezing point of a solution is measured by using a high-sensitivity temperature-sensing element on the basis of the proportional relation between the freezing point depression value and the molar concentration of the solution, and then converted into the osmotic pressure through electric quantity. Manufacturer of instrument: Loser, model: OM815.

Example 1: Screening of Buffer Systems

Formulations containing 100 mg/mL hu25G7-A antibody and 0.1 mg/mL polysorbate 80 (PS80) were prepared in different buffer systems with a pH of 4.5-6.5, and stability of the antibody in the different buffer systems was examined. The specific design of formulas is shown in the table below.

TABLE 13

Ingredients of formulation samples

| Sample No. | Buffer system |
|---|---|
| 1 | 20 mM histidine-acetic acid (His-AA) pH 4.5 |
| 2 | 20 mM His-AA pH 5.0 |
| 3 | 20 mM acetic acid-sodium acetate (AA) pH 5.5 |
| 4 | 20 mM succinic acid-sodium succinate (SA) pH 5.5 |
| 5 | 20 mM citric acid-sodium citrate (CA) pH 5.5 |
| 6 | 20 mM His-AA pH 5.5 |
| 7 | 20 mM His-AA pH 6.0 |
| 8 | 20 mM His-AA pH 6.5 |

The samples were each subjected to sterile filtration, filled into vials, and then examined for the appearance and SEC under the high-temperature condition of 40° C. The data are shown in the table below.

TABLE 14

Stability results of formulation samples

| Sample | Conditions | Appearance | SEC Monomer % | Relative change in SEC % |
|---|---|---|---|---|
| 1 | T0 | Transparent | 99.2 | |
| | 40° C. D 15 | Transparent | 96.6 | 2.5 |
| | 40° C. M 1 | Transparent | 94.5 | 4.7 |
| 2 | T0 | Transparent | 99.4 | |
| | 40° C. D 15 | Transparent | 96.9 | 2.5 |
| | 40° C. M 1 | Transparent | 94.9 | 4.5 |
| 3 | T0 | Transparent | 99.3 | |
| | 40° C. D 15 | Transparent and opalescent | 96.5 | 2.7 |
| | 40° C. M 1 | Opalescent, with a small number of haze-like particles | 94.2 | 5.0 |
| 4 | T0 | Transparent and opalescent | 99.4 | |
| | 40° C. D 15 | A large number of particles | 96.2 | 3.2 |

TABLE 14-continued

Stability results of formulation samples

| Sample | Conditions | Appearance | SEC Monomer % | Relative change in SEC % |
|---|---|---|---|---|
| | 40° C. M 1 | Opalescent, with a large number of haze-like particles | 93.9 | 5.4 |
| 5 | T0 | Transparent and opalescent | 99.3 | |
| | 40° C. D 15 | A large number of particles | 96.6 | 2.8 |
| | 40° C. M 1 | Opalescent, with a large number of haze-like particles | 94.9 | 4.4 |
| 6 | T0 | Transparent | 99.4 | |
| | 40° C. D 15 | Transparent | 96.3 | 3.1 |
| | 40° C. M 1 | Transparent | 94.5 | 4.9 |
| 7 | T0 | Transparent | 99.1 | |
| | 40° C. D 15 | Transparent | 96.8 | 2.3 |
| | 40° C. M 1 | Transparent and opalescent | 95.1 | 4.0 |
| 8 | T0 | N/A | 99.0 | |
| | 40° C. D 15 | N/A | 94.3 | 4.8 |
| | 40° C. M 1 | Turbid | N/A | N/A |

Note:

D 15 represents detection on day 15, M represents month, T0 represents immediate detection after sample preparation, and N/A represents no detection.

The results showed that the appearance of the SA/CA/AA buffers was relatively bad, and therefore His-AA was selected as the buffer system. In the His-AA system, the pH of 4.5-5.5 resulted in better appearance; except for His-AA of the formulation. Then the samples were each subjected to sterile filtration, filled into vials, and then examined for the appearance, SEC, non-reduced CE-SDS and iCIEF under the high-temperature condition of 40° C. to examine the influence of different antibody concentrations on the viscosity and stability of hu25G7-A formulations. The results are shown in the tables below:

TABLE 15

Measurement results of formulation viscosity

| Sample | Viscosity mPa · s |
|---|---|
| 1 | 13.7 |
| 2 | 25.5 |
| 3 | 90.0 |
| 4 | 140.5 |
| 5 | 34.6 |
| 6 | 26.5 |
| 7 | 21.8 |
| 8 | 93.2 |
| 9 | 52.6 |

TABLE 16

Measurement results of formulation stability

| Sample | Conditions | Appearance | SEC monomer % | Change % | iCIEF neutral peak % | Change % | Non-reduced CE-SDS % | Change % |
|---|---|---|---|---|---|---|---|---|
| 1 | T0 | Transparent | 99.4 | | 65.0 | | 96.12 | |
| | 40° C. D 15 | Transparent | 96.9 | 2.5 | 57.5 | 7.5 | 92.37 | 3.75 |
| 2 | T0 | Transparent | 99.4 | | 65.3 | | 95.93 | |
| | 40° C. D 15 | Transparent | 96.3 | 3.1 | 55.0 | 10.3 | 92.09 | 3.84 |
| 3 | T0 | Transparent | 99.3 | | 63.9 | | 96.10 | |
| | 40° C. D 15 | Transparent | 96.4 | 2.9 | 54.8 | 9.1 | 92.85 | 3.25 |
| 4 | T0 | Transparent | 99.4 | | 65.0 | | 96.22 | |
| | 40° C. D 15 | N/A[1] | 96.5 | 2.9 | 53.1 | 11.9 | 91.29 | 4.93 | pH 6.5, SEC of each buffer system had no significant difference, and pH 5.0 and 6.0 were slightly better. Therefore, the buffer system of the antibody was His-AA, pH 4.5-6.0.

Example 2: Screening of Antibody Concentrations

Formulations of hu25G7-A at different concentrations were prepared in 20 mM His-AA pH 5.0, 5.5 buffer systems, and the formulation ingredients are as follows:

1) 20 mM His-AA pH5.0, 100 mg/mL hu25G7-A
2) 20 mM His-AA pH5.5, 100 mg/mL hu25G7-A
3) 20 mM His-AA pH5.0, 150 mg/mL hu25G7-A
4) 20 mM His-AA pH5.5, 150 mg/mL hu25G7-A
5) 20 mM His-AA pH5.0, 139 mg/mL hu25G7-A
6) 20 mM His-AA pH5.0, 127 mg/mL hu25G7-A
7) 20 mM His-AA pH5.0, 120 mg/mL hu25G7-A
8) 20 mM His-AA pH5.5, 138 mg/mL hu25G7-A
9) 20 mM His-AA pH5.5, 122 mg/mL hu25G7-A

After each of the formulations was prepared, firstly a part of the formulation sample was taken to detect the viscosity The results showed that: the appearance, SEC, CE and iCIEF of different antibody concentrations had no significant difference; namely in His-AA buffers with pH 5.0 or 5.5, the antibody concentration had little influence on the stability of the formulation; however, the higher the antibody concentration, the higher the viscosity of the formulation, and in the buffer solution with pH 5.0, the viscosity was about 14 mPa·s, when the antibody concentration was 100 mg/mL, while the viscosity was about 22 mPa·s when the antibody concentration was 120 mg/mL.

Example 3: Screening of Viscosity Modifiers

The hu25G7-A formulations containing different viscosity modifiers at an antibody concentration of 120 mg/mL were prepared in 20 mM His-AA (pH 5.0) buffer. The influence of different viscosity modifiers on the viscosity of the formulation was examined with viscosity as the evaluation index. To meet the isotonic requirements of the subcutaneous formulations, each viscosity modifier was added to the formulation at a blank viscosity modifier osmotic pressure of 270 mosm/kg to examine its effect. Specific results are shown in the table below.

TABLE 17

Viscosity results

| Viscosity modifier | Concentration (mM) | Average viscosity mPa · s |
|---|---|---|
| Not added (blank) | N/A | 16 |
| NaCl | 122 | 8 |
| MgCl₂ | 85 | 5.3 |
| CaCl₂ | 148 | 5.6 |
| KCl | 124 | 7.7 |
| CH₃COONa | 86 | 8.8 |
| Na₂SO₄ | 96 | 9.5 |
| NaI | 113 | 8.3 |
| NaF | 74 | 6.3 |
| NaSCN | 112 | 6.6 |
| Arg-HCl | 120 | 7.2 |
| Lys | 118 | 8.7 |
| His | 93 | 6.6 |
| Pro | 207 | 12.9 |

The results showed that, NaCl, MgCl$_2$, CaCl$_2$, KCl, CH$_3$COONa, Na$_2$SO$_4$, NaI, NaF, NaSCN, Arg-Hcl, Lys (lysine) and His (histidine), except for proline, all had a significant effect in reducing the viscosity of the formulation at the corresponding maximum concentration. Among these modifiers, Arg-HCl, MgCl$_2$, CaCl$_2$, NaF, NaSCN and histidine had a better effect, and thus Arg-HCl, MgCl$_2$, CaCl$_2$ and histidine were preferred as viscosity modifiers.

Example 4: Effect of Viscosity Modifiers on Viscosity of High-Concentration Formulations To test the effect of the viscosity modifier, hu25G7-A formulations at an antibody concentration of 150 mg/mL hu25G7-A were prepared in 20 mM His-AA, pH5.0 buffer, and the specific ingredients are as follows:
1) Without a viscosity modifier (N/A)
2) 85 mM MgCl$_2$
3) 148 mM CaCl$_2$
4) 93 mM histidine
The influence of different auxiliary materials on the viscosity of the high-concentration formulation was examined with viscosity as the evaluation index.

TABLE 18

Viscosity results

| Sample | Viscosity mPa · s |
|---|---|
| 1 | 88.80 |
| 2 | 16.86 |
| 3 | 17.22 |
| 4 | 19.00 |

The result showed that when the concentration of the antibody was 150 mg/mL, the viscosity of the formulation could be reduced to be below 20 mPa·s by MgCl$_2$, CaCl$_2$ and histidine, and the viscosity reduction effect was relatively good.

Example 5: Influence of Viscosity Modifiers on Formulation Stability

In a 20 mM His-AA pH 5.0 buffer system, Hu25G7-A formulations, at an antibody concentration of 150 mg/mL and containing auxiliary materials at different concentrations, were prepared, and the influence of the auxiliary materials at different concentrations on the thermal stability (stored for 17 days at 40° C.) of the formulation was examined. The experimental design and results are shown in the table below.

TABLE 19

Formulation samples

| Sample | Viscosity modifier |
|---|---|
| 1 | Blank (not added) |
| 2 | 50 mM MgCl2 |
| 3 | 90 mM MgCl2 |
| 4 | 90 mM CaCl2 |
| 5 | 148 mM CaCl2 |
| 6 | 90 mM histidine |
| 7 | 122 mM NaCl |
| 8 | 120 mM Arg-HCl |

TABLE 20

Influence of amount of auxiliary materials on sample stability

| Sample | Conditions | SEC monomer % | Relative change in SEC % | Non-reduced CE-SDS % | Relative change in CE % |
|---|---|---|---|---|---|
| 1 | T0 | 99.0 | | 95.7 | |
| | 40° C. D 17 | 94.7 | 4.3 | 93.5 | 2.2 |
| 2 | T0 | 99.0 | | 95.6 | |
| | 40° C. D 17 | 94.3 | 4.7 | 91.9 | 3.7 |
| 3 | T0 | 99.0 | | 95.7 | |
| | 40° C. D 17 | 93.8 | 5.2 | 91.4 | 4.3 |
| 4 | T0 | 99.0 | | 95.1 | |
| | 40° C. D 17 | 93.4 | 5.6 | 88.9 | 6.2 |
| 5 | T0 | 98.8 | | 95.7 | |
| | 40° C. D 17 | 92.9 | 5.9 | 87.9 | 7.8 |
| 6 | T0 | 99.0 | | 95.3 | |
| | 40° C. D 17 | 95.7 | 3.3 | 90.8 | 4.5 |
| 7 | T0 | 99.0 | | 95.3 | |
| | 40° C. D 17 | 94.3 | 4.7 | 90.3 | 5 |
| 8 | T0 | 98.9 | | 95.2 | |
| | 40° C. D 17 | 94.8 | 4.1 | 91.0 | 4.2 |

The results showed that: MgCl$_2$, Arg-HCl, NaCl and histidine had a small influence on the stability of the formulation, where the stability of the formulations containing MgCl$_2$, Arg-HCl, NaCl and histidine was better than that of the formulation containing CaCl$_2$, the CE reduction of the CaCl$_2$ group under high-temperature conditions was greater than that of other formulation samples, and the stability of the formulations containing MgCl$_2$, Arg-HCl and histidine was better, and thus MgCl$_2$, Arg-HCl and histidine were preferred.

Example 6: Overall Evaluation of Influence of Viscosity Modifier on Formulation Stability In 20 mM His-AA pH 5.0 buffer, formulations containing 0.1 mg/mL PS80, 150 mg/mL Hu25G7-A and a viscosity modifier were prepared, where the concentration of PS80 in a sample shaken for 15 days was 1 mg/mL. The influence of different auxiliary materials on the viscosity and the stability of the Hu25G7-A preparation was examined. Experimental design is as follows.

1) N/A (without a viscosity modifier)
2) 90 mM $MgCl_2$
3) 120 mM Arg-HCl
4) 90 mM histidine After each of the formulations was prepared, firstly a part of the formulation sample was taken to detect the viscosity of the formulation. Then the samples were each subjected to sterile filtration, filled into vials, and then examined for the appearance, SEC, non-reduced CE under the conditions of high temperature of 40° C., repeated freezing and thawing (−35° C. to 4° C.) and shaking (300 rpm at 25° C.) to evaluate the influence of different auxiliary materials on the viscosity and stability of formulations. The results are shown in the tables below.

TABLE 21

Measurement results of viscosity

| Sample | Viscosity mPa · s |
|---|---|
| 1 | 82.2 |
| 2 | 12.1 |
| 3 | 15.8 |
| 4 | 17.7 |

TABLE 22

Stability results

| Sample | Conditions | Appearance | SEC Monomer % | Relative change in SEC % | Non-reduced CE | Relative change in CE % |
|---|---|---|---|---|---|---|
| 1 | T0 | Transparent | 99.2 | | 96.5 | |
| | 40° C. M 1 | Transparent | 93.9 | 5.3 | 90.3 | 6.2 |
| | Freezing and thawing 5 times | Transparent | 98.7 | 0.5 | 95.7 | 0.8 |
| | Shaking D 1 | Transparent | 98.8 | 0.4 | 95.9 | 0.6 |
| | Shaking D 15 | Transparent | 98.7 | 0.5 | 95.0 | 1.5 |
| 2 | T0 | Transparent and slightly opalescent | 99.4 | | 95.9 | |
| | 40° C. M 1 | Opalescent, with a large number of haze-like particles | 92.2 | 7.2 | 88.3 | 7.6 |
| | Freezing and thawing 5 times | Transparent and opalescent | 98.5 | 0.9 | 95.3 | 0.6 |
| | Shaking D 1 | Particles appeared | 98.5 | 0.9 | 95.5 | 0.4 |
| | Shaking D 15 | Transparent | 98.5 | 0.9 | 94.2 | 1.7 |
| 3 | T0 | Transparent and slightly opalescent | 99.3 | | 95.8 | |
| | 40° C. M 1 | Opalescent, with a large number of haze-like particles | 93.0 | 6.3 | 88.8 | 7 |
| | Freezing and thawing 5 times | Transparent and opalescent | 98.5 | 0.8 | 95.6 | 0.2 |
| | Shaking D 1 | Particles appeared | 98.4 | 0.9 | 95.7 | 0.1 |
| | Shaking D 15 | Transparent | 98.4 | 0.9 | 95.1 | 0.7 |
| 4 | T0 | Transparent and slightly opalescent | 99.5 | | 96.1 | |
| | 40° C. M 1 | Opalescent, with a large number of haze-like particles | 94.1 | 5.4 | 89.0 | 7.1 |
| | Freezing and thawing 5 times | Transparent and opalescent | 98.6 | 0.9 | 95.3 | 0.8 |
| | Shaking D 1 | Particles appeared | 98.3 | 1.2 | 95.8 | 0.3 |
| | Shaking D 15 | Transparent | 98.6 | 0.9 | 95.0 | 1.1 |

Note:
shaking D 1 represents detection after shaking for 1 day, and shaking D 15 represents detection after shaking for 15 days.

The results showed that:

after the auxiliary material viscosity modifier was added, the appearance showed opalescence, but no difference existed among the auxiliary materials; when the formulation contained 0.1 mg/mL PS80, the viscosity modifier-containing group was shaken for one day and particles appeared. However, when PS80 was 1 mg/mL, the appearance remained transparent after shaking for 15 days.

The SEC results at 40° C. showed that the SEC monomer content was slightly reduced after the viscosity modifier was added, but no significant difference existed among the samples of each group, where the Arg-HCl sample group and the histidine sample group were better, and the histidine sample was the best in stability. The CE results at 40° C. showed that the CE was slightly reduced after the viscosity modifier was added, but the difference among the auxiliary materials was small.

Example 7: Screening of Viscosity Modifier Concentrations

In a 20 mM His-AA pH 5.0 buffer system, formulations containing Hu25G7-A antibody different concentrations and viscosity modifier were prepared to examine the viscosity of formulations. The experimental design and results are shown in the table below.

TABLE 23

| | | | |
|---|---|---|---|
| Measurement results of viscosity | | | |
| Viscosity modifier | Viscosity modifier concentration (mM) | Protein concentration (mg/mL) | Viscosity mPa · s |
| MgCl$_2$ | 10 | 163.1 | 37.9 |
| | 50 | 163.8 | 18.6 |
| | 90 | 165.1 | 18.0 |
| | 90 | 190 | 31.2 |
| His | 10 | 162.6 | 49.1 |
| | 50 | 163.9 | 27.0 |
| | 90 | 164.2 | 19.1 |
| Arg-HCl | 10 | 160.7 | 54.4 |
| | 50 | 163.0 | 31.5 |
| | 90 | 163.4 | 21.6 |
| | 120 | 166.0 | 19.9 |
| | 150 | 152 | 18.9 |
| | 180 | 149 | 16.5 |
| | 200 | 147 | 14.8 |

The results showed that increasing the concentration of the viscosity modifiers His, MgCl$_2$ and Arg-HCl could significantly reduce the viscosity of the formulation.

of the formulation. Then the samples were each subjected to sterile filtration, filled into vials, and then examined for stability at 4° C. and 25° C. The appearance, osmotic pressure, pH, SEC, non-reduced CE and iCIEF of the samples were detected to evaluate the viscosity and stability of different formulation samples, and the results are shown in the table.

TABLE 24

| | | | | | |
|---|---|---|---|---|---|
| Viscosity, pH and osmotic pressure results | | | | | |
| Sample | | Osmotic pressure | Viscosity mPa · s | | |
| | pH | mosm/kg | Detection 1 | Detection 2 | Average |
| 1 | 5.03 | 284 | 13.33 | 12.26 | 12.8 |
| 2 | 4.91 | 306 | 16.28 | 14.84 | 15.5 |
| 3 | 5.01 | 310 | 14.99 | 16.16 | 15.6 |
| 4 | 5.09 | 292 | 14.02 | 16.63 | 15.3 |

TABLE 25

| Sample | Conditions | Appearance | SEC monomer % | Relative change in SEC % | iCIEF neutral peak % | Relative change in iCIEF % | Non-reduced CE-SDS % | Relative change in CE-SDS % |
|---|---|---|---|---|---|---|---|---|
| | | | | Stability results at 4° C. and 25° C. | | | | |
| 1 | T0 | Transparent | 98.7 | | 69.1 | | 95.3 | |
| | 25° C. M 1 | Transparent | 97.8 | 0.9 | 65.3 | 3.8 | 95.4 | −0.1 |
| | 25° C. M 3 | Transparent | 97.2 | 1.5 | 58.7 | 10.4 | 92.8 | 2.5 |
| | 4° C. M 3 | Transparent | 97.5 | 1.2 | 65.9 | 3.2 | 95.6 | −0.2 |
| | 4° C. M 11 | Transparent | 98.2 | 0.5 | 64.9 | 4.2 | 97.0 | −1.7 |
| 2 | T0 | Transparent | 98.5 | | 68.7 | | 94.8 | |
| | 25° C. M 1 | Transparent | 97.7 | 0.8 | 60.2 | 8.5 | 94.6 | 0.2 |
| | 4° C. M 11 | Transparent | 98.7 | −0.2 | 63.9 | 4.8 | 96.9 | −2.1 |
| 3 | T0 | Transparent | 98.5 | | 69.2 | | 95.0 | |
| | 25° C. M 1 | Transparent | 97.8 | 0.7 | 60.7 | 8.5 | 94.8 | 0.2 |
| | 4° C. M 11 | Transparent | 98.7 | −0.2 | 64.3 | 4.9 | 96.5 | −1.5 |
| 4 | T0 | Transparent | 98.6 | | 69.0 | | 95.0 | |
| | 25° C. M 1 | Transparent | 97.7 | 0.9 | 62.4 | 6.6 | 95.1 | −0.1 |
| | 4° C. M 11 | Transparent | 98.7 | −0.1 | 64.2 | 4.8 | 96.7 | −1.7 |

Example 8: Formulation Stability Test

To improve the appearance of the formulation, the amount of the basic amino acid (viscosity modifier) added to the formulation was considered to be reduced, and formulation samples were prepared as follows:

1. 20 mM His-AA pH 5.0, 30 mM histidine, 0.8 mg/mL PS80, 41.8 mg/mL sucrose, antibody Hu25G7-A 120 mg/mL, the final content of histidine in the sample being 50 mM;

2. 20 mM His-AA pH 4.8, 87 mM histidine, 0.8 mg/mL PS80, 150 mg/mL antibody Hu25G7-A;

3. 20 mM His-AA pH 5.0, 100 mM histidine, 0.8 mg/mL PS80, 150 mg/mL antibody Hu25G7-A;

4. 20 mM His-AA pH 5.0, 120 mM arginine hydrochloride, 0.8 mg/mL PS80, 150 mg/mL antibody Hu25G7-A;

After each of the formulations was prepared, firstly a part of the formulation sample was taken to detect the viscosity The results showed that: the pH changes of the Nos. 1-4 formulation samples were all within 0.1, and the buffer capacity was relatively good; the osmotic pressure was in an isotonic range, and the viscosity was all within 20 mPa·s; after the sample No. 1 was stored at 25° C. for 3 months, the CE/iCIEF slightly decreased, and after being stored for 3 months at 4° C., the appearance was still transparent, and the chemical stability was not significantly changed. The samples Nos. 1-4 were clear in appearance after being stored at 4° C. for 11 months, and the detection results of SEC, iCIEF and CE-SDS were stable, so that the Nos. 1-4 formulations described above were all relatively stable.

Example 9: Screening of Sugar Concentrations

To develop a subcutaneous formulation and reduce injection irritation, it was best to control the osmotic pressure to be isotonic, and thus sugar concentrations were screened to determine an isotonic sugar concentration. A formulation containing 50 mM His-AA pH 5.0, 58 mg/mL PS80 and 120 mg/mL hu25G7-A antibody was prepared, and the osmotic pressure was measured 3 times using the freezing point method.

TABLE 26

| Osmotic pressure of formulation (mosm/kg) | | | |
|---|---|---|---|
| Detection 1 | Detection 2 | Detection 3 | Average value |
| 290 | 298 | 304 | 297 |

The results showed that the osmotic pressure was about 297 mosm/kg, i.e., isotonic, at a sugar concentration of 58 mg/mL.

Example 10: Screening of Lyophilization Processes

A formulation containing 25 mM His-AA pH 4.9, 60 mg/mL hu25G7-A, 25 mg/mL sucrose and 0.2 mg/mL PS80 was prepared, subjected to sterile filtration, filled into vials at 3.4 mL/vial, and lyophilized according to the following procedure.

TABLE 27

| Lyophilization procedure | | | | |
|---|---|---|---|---|
| Process parameters | Set temperature (° C.) | Set time (min) | Retention time (h) | Degree of vacuum (Pa) |
| Feeding in | 5 | N/A | N/A | N/A |
| Pre-freezing | 5 | 10 | 1 | N/A |
| Pre-freezing | −45 | 50 | 2.5 | N/A |
| Primary drying | −5 | 60 | 30 | 20 |
| Secondary drying | 25 | 60 | 1 | 10 |
| Secondary drying | 25 | 1 | 7.5 | 1 |

After being lyophilized, the sample was taken out of the box, wherein the appearance of the sample was as follows: white pressed powder with full appearance and no collapse. Approximately 1.5 mL of water for injection was used for reconstitution, and the ingredients of the reconstituted sample were as follows: 50 mM His-AA, 120 mg/mL hu25G7-A, 50 mg/mL sucrose, 0.4 mg/mL PS80, pH 5.3. The reconstituted sample was subjected to various detections. The results showed that the indexes of the reconstituted solution after the dilute freezing and the concentrated dissolving were good.

TABLE 28

| Stability results before and after lyophilization | | | | |
|---|---|---|---|---|
| Time | Appearance | SEC Monomer % | iCIEF Neutral peak % | Non-reduced CE-SDS % |
| Before lyophilization | N/A | 99.1 | 62.1 | 96.4 |
| After lyophilization | Transparent and opalescent, slightly yellowish | 98.9 | 62.0 | 95.8 |

Example 11: Optimization of Formulation Formulas

DOE experimental design was performed with 50 mM His-AA buffer pH, Hu25G7-A antibody concentration and PS80 concentration as variables (the variables were: pH 4.5-5.5, PS80 0.4-1.2 mg/mL and Hu25G7-A antibody protein concentration 100-140 mg/mL), and JMP software was used to obtain a series of Hu25G7-A formulation formulas, where the formulas all contained 58 mg/mL sucrose, and the specific information is shown in Table 29. The stability of the formulations was tested by forced degradation, including 40° C. high temperature, shaking (300 rpm) and freeze-thaw experiments (−35° C. to 4° C.). The appearance, viscosity, SEC, non-reduced CE and iCIEF were used as evaluation indexes, and the results are shown in Table 30. The least square method was used for statistical analysis of the results.

TABLE 29

| Ingredients and viscosity of experimental formulations in DOE formula screening | | | | | |
|---|---|---|---|---|---|
| Sample | Antibody concentration (mg/mL) | pH | PS80 (mg/mL) | Actual antibody concentration (mg/mL) | Viscosity (mPa · s) |
| 01 | 132.6 | 5 | 0.4 | 132.9 | 21.9 |
| 02 | 100 | 5 | 0.8 | 97.2 | 9.8 |
| 03 | 140 | 5 | 1.2 | 143.6 | 32.7 |
| 04 | 100 | 4.5 | 0.4 | 104.4 | 6.5 |
| 05 | 140 | 4.5 | 0.8 | 143.0 | 14.9 |
| 06 | 120 | 4.5 | 1.2 | 123.7 | 8.9 |
| 07 | 100 | 5 | 1.2 | 97.3 | 9.2 |
| 08 | 100 | 5.5 | 0.4 | 97.1 | 13.7 |
| 09 | 120 | 5.5 | 1.2 | 122.2 | 25.1 |
| 10 | 120 | 5 | 0.8 | 121.6 | 16.3 |
| 11 | 120 | 5 | 0.8 | 122.4 | 14.4 |

TABLE 30

| Results of DOE formula screening experiment | | | | | |
|---|---|---|---|---|---|
| Sample | Conditions | Appearance | SEC monomer % | iCIEF neutral peak % | Non-reduced CE-SDS % |
| 01 | D 0 | Transparent | 99.7 | 66.5 | 97.3 |
| | 40° C.-M 1.6 | Transparent | 96.6 | 37.9 | 96.7 |
| | Shaking-D 14 | Transparent | 99.5 | N/A | N/A |
| 02 | D 0 | Transparent | 99.6 | 66 | 97.2 |
| | 40° C.-M 1.6 | Transparent | 96.7 | 37.5 | 96.2 |
| | Shaking-D 14 | Transparent | 99.6 | N/A | N/A |
| 03 | D 0 | Transparent | 99.8 | 66.5 | 97.5 |
| | 40° C.-M 1.6 | Transparent | 96.1 | 37.4 | 96.6 |
| | Shaking-D 14 | Transparent | 99.5 | N/A | N/A |
| 04 | D 0 | Transparent | 99.7 | 67.8 | 97.7 |
| | 40° C.-M 1.6 | Transparent | 96.1 | 33.4 | 95.4 |
| | Shaking-D 14 | Transparent | 99.5 | N/A | N/A |
| 05 | D 0 | Transparent | 99.7 | 66.8 | 97.9 |
| | 40° C.-M 1.6 | Transparent | 95.8 | 32.3 | 95.6 |
| | Shaking-D 14 | Transparent | 99.6 | N/A | N/A |
| 06 | D 0 | Transparent | 99.7 | 66.9 | 97.2 |
| | 40° C.-M 1.6 | Transparent | 95.6 | 33 | 92.6 |
| | Shaking-D 14 | Transparent | 99.5 | N/A | N/A |
| 07 | D 0 | Transparent | 99.9 | 66.4 | 98.1 |
| | 40° C.-M 1.6 | Transparent | 95.8 | 35.4 | 96.1 |
| | Shaking-D 14 | Transparent | 99.7 | N/A | N/A |
| 08 | D 0 | Transparent | 99.6 | 66.2 | 97.9 |
| | 40° C.-M 1.6 | Transparent | 96.4 | 38 | 95.6 |
| | Shaking-D 14 | Transparent | 99.7 | N/A | N/A |
| 09 | D 0 | Transparent | 99.4 | 67.6 | 96.7 |
| | 40° C.-M 1.6 | Transparent | 95.7 | 36.7 | 94.4 |
| | Shaking-D 14 | Transparent | 99.5 | N/A | N/A |
| 10 | D 0 | Transparent | 99.8 | 66.1 | 97.2 |
| | 40° C.-M 1.6 | Transparent | 96.2 | 38.2 | 95.1 |
| | Shaking-D 14 | Transparent | 99.7 | N/A | N/A |
| 11 | D 0 | Transparent | 99.6 | 67.4 | 97.1 |
| | 40° C.-M 1.6 | Transparent | 96.2 | 37.6 | 95.1 |
| | Shaking-D 14 | Transparent | 99.7 | N/A | N/A |

Note:
M 1.6 represents 1.6 months; D 14 represents day 14, and D 0 represents the start of the experiment.

The results showed that after 5 freeze-thaw cycles, each formulation remained clear in appearance.

Figure 2:
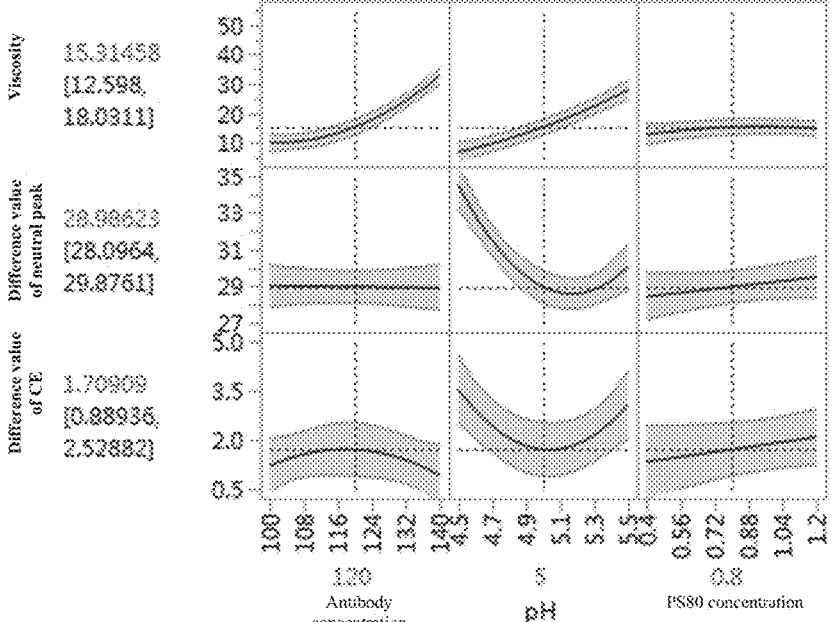
FIG. 2 shows the fitting results of formulation formulas.
Figure 3:
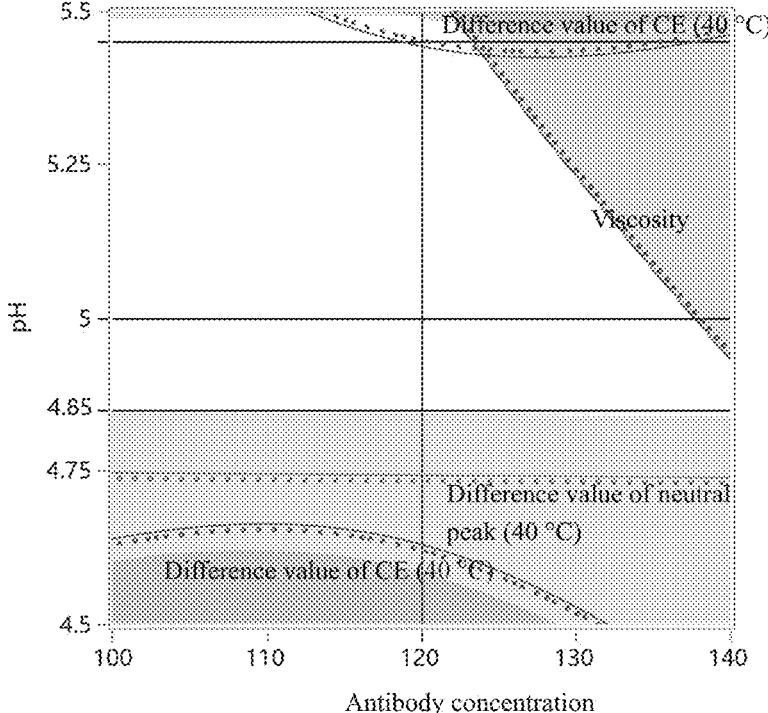
FIG. 3 shows a contour diagram of the change in formulation stability, with the gray areas indicating being beyond the limits and the white area indicating being within the limits.

The forced degradation data were fitted, and the degradation difference values of viscosity and 40° C. CE and iCIEF were well fitted, and the model was effective. The results are shown in FIG. 2. When the PS concentration was 0.8 mg/mL, a contour diagram was drawn by taking the antibody concentration and the pH as horizontal and vertical coordinates, respectively, and the viscosity and the 40° C. CE/iCIEF degradation difference value as indexes, and a contour diagram of the stability change of the formulations was drawn by taking the viscosity<30 cP, the CE reduction<3% and the iCIEF reduction<30% as limits, and the results are shown in FIG. 3.

The results showed that: the lower the protein concentration, the lower the pH, and the lower the viscosity of the formulation; the CE results were optimal when pH was 5.0, and the iCIEF neutral peak was optimal when pH was 5.1. With reference to the contour diagrams and viscosity results, the stable formulation is as follows: the antibody concentration is 100-140 mg/mL, PS80 is 0.4-1.2 mg/mL, and the pH is 4.5-5.5. Furthermore, the formulation is more stable when the antibody concentration is 110-130 mg/mL and the pH is 4.85-5.45.

Example 12: Formulation Stability Test

A formulation containing 50 mM His-AA pH 5.0, 120 mg/mL hu25G7-A antibody, 58 mg/mL sucrose and 0.8 mg/mL PS80 was prepared, subjected to sterile filtration and filled into vials. The 4° C. stability test was then carried out and the results are shown in Table 31.

TABLE 31

| | | | iCIEF | Non- |
|---|---|---|---|---|
| | | SEC | neutral | reduced |
| Time | Appearance | monomer % | peak % | CE-SDS % |
| T0 | Transparent | 99.1 | 61.5 | 97.2 |
| 4° C. M 4 | Transparent | 98.8 | 66.8 | 98.1 |

*Results of 4° C. stability test*

The results showed that: the formulation described above was still stable after being stored for 4 months at 4° C.

What is claimed:

1. A pharmaceutical composition, comprising an anti-IL-4R antibody or an antigen-binding fragment thereof, a buffer, a surfactant, and a viscosity modifier, wherein:

the buffer is a histidine-acetic acid buffer, and the buffer has a pH of 4.5 to 6.0, the histidine-acetic acid buffer has a concentration of 10 mM to 60 mM; the surfactant has a concentration of 0.1 mg/mL to 1.2 mg/mL, the viscosity modifier is selected from the group consisting of MgCl$_2$, histidine and arginine hydrochloride, and the viscosity modifier has a concentration of 5 mM to 220 mM;

the anti-IL-4R antibody or the antigen-binding fragment thereof has a concentration of 100 mg/mL to 200 mg/mL, and the anti-IL-4R antibody or the antigen-binding fragment thereof comprises:

(i) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 38, SEQ ID NO: 7 and SEQ ID NO: 40, respectively;

(ii) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 6, SEQ ID NO: 7 and SEQ ID NO: 8, respectively;

(iii) a heavy chain variable region comprising an HCDR1, an HCDR2 and an HCDR3 set forth in SEQ ID NO: 11, SEQ ID NO: 12 and SEQ ID NO: 13, respectively; and a light chain variable region comprising an LCDR1, an LCDR2 and an LCDR3 set forth in SEQ ID NO: 14, SEQ ID NO: 15 and SEQ ID NO: 16, respectively; or (iv) a heavy chain variable region comprising an HCDR1, an HCDR2 and an HCDR3 set forth in SEQ ID NO: 3, SEQ ID NO: 4 and SEQ ID NO: 5, respectively; and a light chain variable region comprising an LCDR1, an LCDR2 and an LCDR3 set forth in SEQ ID NO: 42, SEQ ID NO: 39 and SEQ ID NO: 8, respectively.

2. The pharmaceutical composition according to claim 1, wherein the histidine-acetic acid buffer has a concentration of 10 mM to 30 mM.

3. The pharmaceutical composition according to claim 1, wherein the anti-IL-4R antibody or the antigen-binding fragment thereof has a concentration of 100 mg/ml to 180 mg/mL.

4. The pharmaceutical composition according to claim 1, wherein the viscosity modifier has a concentration of 5 mM to 220 mM, or 5 mM to 148 mM.

5. The pharmaceutical composition according to claim 4, wherein the anti-IL-4R antibody or the antigen-binding fragment thereof has a concentration of 120 mg/ml to 150 mg/mL; and the viscosity modifier is selected from the group consisting of 50 mM to 90 mM $MgCl_2$, 50 mM to 100 mM histidine, and 10 mM to 200 mM.

6. The pharmaceutical composition according to claim 1, wherein the surfactant is polysorbate.

7. The pharmaceutical composition according to claim 6, wherein the surfactant has a concentration 0.4 mg/mL to 1.0 mg/mL.

8. The pharmaceutical composition according to claim 1, further comprising a stabilizer, the stabilizer has a concentration of 20 mg/mL to 70 mg/mL, or 40 mg/ml to 60 mg/mL.

9. The pharmaceutical composition according to claim 1, comprising:

(a) 100 mg/mL to 150 mg/mL anti-IL-4R antibody or antigen-binding fragment thereof; (b) 10 mM to 30 mM histidine-acetic acid buffer, pH 4.5-5.5; (c) 80 mM to 148 mM viscosity modifier; and (d) 0.4 mg/mL to 1.2 mg/mL polysorbate 80;

or, (a) 100 mg/mL to 120 mg/mL anti-IL-4R antibody or antigen-binding fragment thereof; (b) 10 mM to 20 mM histidine-acetic acid buffer, pH 4.5-5.5; (c) 5 mM to 50 mM histidine; (d) 0.4 mg/mL to 1.0 mg/mL polysorbate 80; and (e) 50 mg/mL to 60 mg/mL sucrose;

or, (a) 100 mg/mL to 140 mg/mL anti-IL-4R antibody or antigen-binding fragment thereof; (b) 10 mM to 30 mM histidine-acetic acid buffer, pH 4.5-5.5; (c) 10 mM to 40 mM viscosity modifier; (d) 0.4 mg/mL to 1.2 mg/mL polysorbate 80; and (e) 40 mg/mL to 70 mg/mL sucrose;

or, (a) 100 mg/mL to 200 mg/mL anti-IL-4R antibody or antigen-binding fragment thereof; (b) 10 mM to 30 mM histidine-acetic acid buffer, pH 4.5-5.5; (c) 40 mM to 220 mM viscosity modifier; and (d) 0.4 mg/mL to 1.2 mg/mL polysorbate 80; or, (a) 100 mg/mL to 140 mg/mL anti-IL-4R antibody or antigen-binding fragment thereof; (b) 10 mM to 30 mM histidine-acetic acid buffer, pH 4.5-5.5; (c) 10 mM to 40 mM viscosity modifier; (d) 0.4 mg/mL to 1.2 mg/mL polysorbate 80; and (e) 40 mg/mL to 70 mg/mL sucrose, wherein the viscosity modifier is histidine, arginine hydrochloride or $MgCl_2$;

or, (a) 100 mg/mL to 180 mg/mL anti-IL-4R antibody or antigen-binding fragment thereof; (b) 10 mM to 30 mM histidine-acetic acid buffer, pH 4.5-5.5; (c) 40 mM to 90 mM $MgCl_2$; and (d) 0.4 mg/ml to 1.2 mg/mL polysorbate 80;

or, (a) 100 mg/mL to 180 mg/mL anti-IL-4R antibody or antigen-binding fragment thereof; (b) 10 mM to 30 mM histidine-acetic acid buffer, pH 4.5-5.5; (c) 50 mM to 100 mM histidine; and (d) 0.4 mg/mL to 1.2 mg/mL polysorbate 80;

or, (a) 100 mg/mL to 180 mg/mL anti-IL-4R antibody or antigen-binding fragment thereof; (b) 10 mM to 30 mM histidine-acetic acid buffer, pH 4.5-5.5; (c) 50 mM to 200 mM arginine hydrochloride; and (d) 0.4 mg/mL to 1.2 mg/mL polysorbate 80;

or, (a) 100 mg/mL to 120 mg/mL anti-IL-4R antibody or antigen-binding fragment thereof; (b) 20 mM to 60 mM histidine-acetic acid buffer, pH 4.5-5.5; (c) 0.4 mg/mL to 1.2 mg/mL polysorbate 80; and (d) 40 mg/mL to 70 mg/mL sucrose;

or, (a) 120 mg/mL anti-IL-4R antibody or antigen-binding fragment thereof; (b) 50 mM histidine-acetic acid buffer, pH 5.0; (c) 0.8 mg/mL polysorbate 80; and (d) 58 mg/mL sucrose;

or, (a) about 150 mg/mL anti-IL-4R antibody or antigen-binding fragment thereof; (b) about 20 mM histidine-acetic acid buffer, pH about 5.0; (c) about 0.8 mg/mL polysorbate 80; and (d) about 120 mM arginine hydrochloride.

10. The pharmaceutical composition according to claim 1, wherein the anti-IL-4R antibody or the antigen-binding fragment thereof comprises a heavy chain variable region and a light chain variable region shown as any one of the following:

(v) the heavy chain variable region has a sequence set forth in SEQ ID NO: 1 or having at least 90% identity to SEQ ID NO: 1, and the light chain variable region has a sequence set forth in SEQ ID NO: 2 or having at least 90% identity to SEQ ID NO: 2;

(vi) the heavy chain variable region has a sequence set forth in SEQ ID NO: 9 or having at least 90% identity to SEQ ID NO: 9, and the light chain variable region has a sequence set forth in SEQ ID NO: 10 or having at least 90% identity to SEQ ID NO: 10;

(vii) the heavy chain variable region has a sequence set forth in SEQ ID NO: 25, 26, 27, 43 or 47 or having at least 90% identity to SEQ ID NO: 25, 26, 27, 43 or 47, and the light chain variable region has a sequence set forth in SEQ ID NO: 28, 29, 30, 37 or 41 or having at least 90% identity to SEQ ID NO: 28, 29, 30, 37 or 41; or (viii) the heavy chain variable region has a sequence set forth in SEQ ID NO: 31, 32 or 33 or having at least 90% identity to SEQ ID NO: 31, 32 or 33, and the light chain variable region has a sequence set forth in SEQ ID NO: 34, 35 or 36 or having at least 90% identity to SEQ ID NO: 34, 35 or 36.

11. The pharmaceutical composition according to claim 10, wherein the anti-IL-4R antibody or the antigen-binding fragment thereof comprises a heavy chain and a light chain shown below:

a heavy chain set forth in SEQ ID NO: 17 and a light chain set forth in SEQ ID NO: 18; or a heavy chain set forth in SEQ ID NO: 19 and a light chain set forth in SEQ ID NO: 20; or a heavy chain set forth in SEQ ID NO: 44 and a light chain set forth in SEQ ID NO: 45; or a heavy chain set forth in SEQ ID NO: 44 and a light chain set forth in SEQ ID NO: 46; or a heavy chain set forth in SEQ ID NO: 48 and a light chain set forth in SEQ ID NO: 46.

12. A method for preparing the pharmaceutical composition according to claim 11, comprising a step of buffer-exchanging a stock solution of the anti-IL-4R antibody or the antigen-binding fragment thereof.

13. A lyophilized formulation comprising an anti-IL-4R antibody or an antigen-binding fragment thereof, wherein the lyophilized formulation is obtained by lyophilizing the pharmaceutical composition according to claim 1.

14. A reconstituted solution comprising an anti-IL-4R antibody or an antigen-binding fragment thereof, wherein the reconstituted solution is obtained by reconstituting the lyophilized formulation according to claim 13.

15. An article of manufacture, comprising a container containing the pharmaceutical composition according to claim 1.

16. A method for treating an immune disease or disorder in a subject in need thereof, comprising administering to the subject a therapeutically effective amount of the pharmaceutical composition according to claim 1, wherein the immune disease or disorder is an IL-4R-mediated disease or disorder.

17. The pharmaceutical composition according to claim 4, wherein the viscosity modifier is:

i) 5 mM to 220 mM arginine hydrochloride;

ii) 5 mM to 100 mM histidine; or iii) 5 mM to 90 mM MgCl$_2$.

18. The pharmaceutical composition according to claim 5, wherein the viscosity modifier is 50 mM to 180 mM arginine hydrochloride.

19. The pharmaceutical composition according to claim 6, wherein the surfactant is polysorbate 80 or polysorbate 20.

20. The pharmaceutical composition according to claim 8, wherein the stabilizer is trehalose or sucrose.

21. The pharmaceutical composition according to claim 10, wherein the anti-IL-4R antibody or the antigen-binding fragment thereof comprises a heavy chain variable region and a light chain variable region shown as any one of the following:

(ix) the heavy chain variable region has a sequence set forth in SEQ ID NO: 43 or having at least 90% identity to SEQ ID NO: 43, and the light chain variable region has a sequence set forth in SEQ ID NO: 37 or having at least 90% identity to SEQ ID NO: 37;

(x) the heavy chain variable region has a sequence set forth in SEQ ID NO: 43 or having at least 90% identity to SEQ ID NO: 43, and the light chain variable region has a sequence set forth in SEQ ID NO: 41 or having at least 90% identity to SEQ ID NO: 41; or (xi) the heavy chain variable region has a sequence set forth in SEQ ID NO: 47 or having at least 90% identity to SEQ ID NO: 47, and the light chain variable region has a sequence set forth in SEQ ID NO: 41 or having at least 90% identity to SEQ ID NO: 41.

22. The method according to claim 16, wherein the immune disease or disorder is selected from the group consisting of: asthma, nasal polyps, chronic sinusitis, allergic skin disorder, eosinophilic esophagitis, chronic obstructive pulmonary disease, allergic rhinitis, arthritis, inflammatory diseases, allergic reaction, autoimmune lymphoproliferative syndrome, autoimmune hemolytic anemia, Barrett's esophagus, autoimmune uveitis, tuberculosis, and renal disease.

\* \* \* \* \*